(12) United States Patent
Schlaepfer et al.

(10) Patent No.: US 9,282,998 B2
(45) Date of Patent: Mar. 15, 2016

(54) BONE FIXATION ASSEMBLY

(75) Inventors: Fridolin J. Schlaepfer, Hoelstein (CH); Christian Ammann, Oberwil (CH); Stefan Saladin, Oltingen (CH)

(73) Assignee: DePuy Synthes Products, Inc., Raynham, MA (US)

( * ) Notice: Subject to any disclaimer, the term of this patent is extended or adjusted under 35 U.S.C. 154(b) by 697 days.

(21) Appl. No.: 13/061,773

(22) PCT Filed: Sep. 4, 2009

(86) PCT No.: PCT/US2009/056100
§ 371 (c)(1),
(2), (4) Date: Mar. 2, 2011

(87) PCT Pub. No.: WO2010/028287
PCT Pub. Date: Mar. 11, 2010

(65) Prior Publication Data
US 2011/0160779 A1    Jun. 30, 2011

Related U.S. Application Data

(60) Provisional application No. 61/094,622, filed on Sep. 5, 2008.

(51) Int. Cl.
*A61B 17/70* (2006.01)

(52) U.S. Cl.
CPC ......... *A61B 17/7032* (2013.01); *A61B 17/7035* (2013.01)

(58) Field of Classification Search
CPC ........... A61B 17/7034; A61B 17/7032; A61B 17/7035
USPC ......... 606/246, 264–273, 276–278, 305–308, 606/319, 324, 328
See application file for complete search history.

(56) References Cited

U.S. PATENT DOCUMENTS

| 4,863,383 A | 9/1989 | Grafelmann |
| 4,936,851 A | 6/1990 | Fox |

(Continued)

FOREIGN PATENT DOCUMENTS

| EP | 0 674 880 | 10/1995 |
| EP | 1248573 A1 | 10/2002 |

(Continued)

OTHER PUBLICATIONS

International Patent Application No. PCT/US2008/070670: International Search Report dated Feb. 17, 2009, 5 pages.

(Continued)

*Primary Examiner* — Jan Christopher Merene
*Assistant Examiner* — Atiya Mahmud
(74) *Attorney, Agent, or Firm* — Baker & Hostetler LLP

(57) ABSTRACT

The present invention is directed an anchor assembly for use in spinal fixation to interconnect a longitudinal spinal rod with a patient's vertebra. The anchor assembly preferably includes a bone anchor (10), a body (20) with a rod-receiving channel, an insert member (40) (preferably a bushing), and a locking cap with a saddle (70). The anchor assembly preferably enables in-situ assembly where the bone anchor may be secured to the patient's vertebra prior to being received within the body of the bone anchor assembly. Accordingly, the anchor assembly enables a surgeon to implant the bone anchor without the body to maximize visibility and access around the anchoring site. Once the bone anchor has been secured to the patient's vertebra, the body may be snapped onto the bone anchor and a spinal rod may be inserted into the rod-receiving channel.

13 Claims, 27 Drawing Sheets

(56) References Cited

U.S. PATENT DOCUMENTS

| | | | |
|---|---|---|---|
| 4,946,458 A | 8/1990 | Harms | |
| 5,116,337 A | 5/1992 | Johnson | |
| 5,207,678 A | 5/1993 | Harms | |
| 5,474,555 A | 12/1995 | Puno | |
| 5,501,684 A | 3/1996 | Schlaepfer | |
| 5,520,689 A | 5/1996 | Schlaepfer et al. | |
| 5,520,690 A | 5/1996 | Errico et al. | |
| 5,527,183 A | 6/1996 | O'Brien | |
| 5,531,746 A | 7/1996 | Errico et al. | |
| 5,534,001 A | 7/1996 | Schlaepfer | |
| 5,549,608 A | 8/1996 | Errico | |
| 5,549,677 A | 8/1996 | Durr | |
| 5,554,157 A | 9/1996 | Errico et al. | |
| 5,562,661 A | 10/1996 | Yoshimi | |
| 5,575,792 A | 11/1996 | Errico | |
| 5,578,033 A | 11/1996 | Errico | |
| 5,584,832 A | 12/1996 | Schlaepfer | |
| 5,584,834 A | 12/1996 | Errico | |
| 5,586,984 A | 12/1996 | Errico et al. | |
| 5,601,429 A | 2/1997 | Blacklock | |
| 5,605,458 A | 2/1997 | Bailey | |
| 5,607,426 A | 3/1997 | Ralph et al. | |
| 5,609,593 A | 3/1997 | Errico | |
| 5,609,594 A | 3/1997 | Errico | |
| 5,643,265 A | 7/1997 | Errico et al. | |
| 5,647,873 A | 7/1997 | Errico et al. | |
| 5,662,651 A | 9/1997 | Tornier et al. | |
| 5,669,911 A | 9/1997 | Errico | |
| 5,683,392 A | 11/1997 | Richelsoph | |
| 5,688,273 A | 11/1997 | Errico | |
| 5,690,630 A | 11/1997 | Errico | |
| 5,704,939 A | 1/1998 | Justin | |
| 5,725,588 A | 3/1998 | Errico et al. | |
| 5,728,098 A | 3/1998 | Sherman | |
| 5,733,285 A | 3/1998 | Errico | |
| 5,782,831 A | 7/1998 | Sherman | |
| 5,797,911 A | 8/1998 | Sherman | |
| 5,817,094 A | 10/1998 | Errico et al. | |
| 5,863,293 A | 1/1999 | Richelsoph | |
| 5,876,402 A | 3/1999 | Errico et al. | |
| 5,879,350 A | 3/1999 | Sherman | |
| 5,882,350 A | 3/1999 | Ralph et al. | |
| 5,885,286 A | 3/1999 | Sherman | |
| 5,888,204 A | 3/1999 | Ralph et al. | |
| 5,899,940 A | 5/1999 | Carchidi | |
| 5,951,287 A | 9/1999 | Hawkinson | |
| 5,961,329 A | 10/1999 | Stucki-McCormick | |
| 5,964,760 A | 10/1999 | Richelsoph | |
| 6,010,503 A | 1/2000 | Richelsoph | |
| 6,017,177 A | 1/2000 | Lanham | |
| 6,053,917 A | 4/2000 | Sherman | |
| 6,074,391 A | 6/2000 | Metz-Stavenhagen | |
| 6,077,262 A | 6/2000 | Schlaepfer et al. | |
| 6,090,110 A | 7/2000 | Metz-Stavenhagen | |
| 6,090,111 A * | 7/2000 | Nichols | 606/266 |
| 6,126,662 A | 10/2000 | Carmichael | |
| 6,132,432 A | 10/2000 | Richelsoph | |
| 6,217,331 B1 | 4/2001 | Rogers | |
| 6,248,105 B1 | 6/2001 | Schlapfer | |
| 6,261,287 B1 | 7/2001 | Metz-Stavenhagen | |
| 6,280,442 B1 | 8/2001 | Barker | |
| 6,355,040 B1 | 3/2002 | Richelsoph | |
| RE37,665 E | 4/2002 | Ralph et al. | |
| 6,368,321 B1 | 4/2002 | Jackson | |
| 6,402,752 B2 | 6/2002 | Schaffler-Wachter | |
| 6,454,772 B1 | 9/2002 | Jackson | |
| 6,485,491 B1 | 11/2002 | Farris | |
| 6,491,696 B1 | 12/2002 | Kunkel | |
| 6,537,070 B1 | 3/2003 | Stucki-McCormick | |
| 6,537,276 B2 | 3/2003 | Metz-Stavenhagen | |
| 6,558,387 B2 | 5/2003 | Errico et al. | |
| 6,565,565 B1 | 5/2003 | Yuan | |
| 6,585,740 B2 | 7/2003 | Schlapfer | |
| 6,660,004 B2 | 12/2003 | Barker | |
| 6,716,214 B1 | 4/2004 | Jackson | |
| 6,770,075 B2 | 8/2004 | Howland | |
| 6,780,186 B2 | 8/2004 | Errico et al. | |
| 6,783,527 B2 | 8/2004 | Drewry | |
| 6,835,196 B2 | 12/2004 | Biedermann et al. | |
| 6,843,791 B2 | 1/2005 | Serhan | |
| 6,869,433 B2 | 3/2005 | Glascott | |
| 6,887,275 B2 | 5/2005 | Carchidi | |
| 6,964,666 B2 | 11/2005 | Jackson | |
| 7,008,227 B2 | 3/2006 | Carmichael | |
| RE39,089 E | 5/2006 | Errico et al. | |
| 7,128,743 B2 | 10/2006 | Metz-Stavenhagen | |
| 7,163,539 B2 | 1/2007 | Abdelgany | |
| 7,186,255 B2 | 3/2007 | Baynham et al. | |
| 7,211,086 B2 | 5/2007 | Biedermann et al. | |
| 7,250,052 B2 | 7/2007 | Landry | |
| 7,316,684 B1 | 1/2008 | Baccelli et al. | |
| 7,967,849 B2 | 6/2011 | Carson et al. | |
| 8,038,701 B2 | 10/2011 | Rock et al. | |
| 8,192,468 B2 * | 6/2012 | Biedermann et al. | 606/257 |
| 8,197,517 B1 | 6/2012 | Lab et al. | |
| 8,241,333 B2 | 8/2012 | Jackson | |
| 8,328,850 B2 * | 12/2012 | Bernard et al. | 606/264 |
| 2001/0047173 A1 | 11/2001 | Schlaepfer et al. | |
| 2002/0045899 A1 | 4/2002 | Errico et al. | |
| 2002/0103487 A1 | 8/2002 | Errico et al. | |
| 2002/0120272 A1 | 8/2002 | Yuan | |
| 2003/0100896 A1 | 5/2003 | Biedermann et al. | |
| 2003/0125742 A1 | 7/2003 | Yuan | |
| 2004/0024464 A1 | 2/2004 | Errico et al. | |
| 2004/0143265 A1 | 7/2004 | Landry | |
| 2004/0172022 A1 | 9/2004 | Landry | |
| 2004/0193160 A1 | 9/2004 | Richelsoph | |
| 2004/0225292 A1 | 11/2004 | Sasso et al. | |
| 2004/0236330 A1 | 11/2004 | Purcell | |
| 2004/0260284 A1 * | 12/2004 | Parker | 606/61 |
| 2005/0049588 A1 | 3/2005 | Jackson | |
| 2005/0154391 A1 | 7/2005 | Doherty | |
| 2005/0203516 A1 | 9/2005 | Biedermann et al. | |
| 2005/0209592 A1 | 9/2005 | Schlapfer et al. | |
| 2005/0228385 A1 | 10/2005 | Iott | |
| 2005/0288671 A1 | 12/2005 | Yuan | |
| 2006/0004357 A1 | 1/2006 | Lee | |
| 2006/0084993 A1 | 4/2006 | Landry | |
| 2006/0084996 A1 | 4/2006 | Metz-Stavenhagen | |
| 2006/0089643 A1 | 4/2006 | Mujwid | |
| 2006/0129149 A1 | 6/2006 | Iott | |
| 2006/0142761 A1 | 6/2006 | Landry | |
| 2006/0149233 A1 | 7/2006 | Richelsoph | |
| 2006/0149241 A1 | 7/2006 | Richelsoph | |
| 2006/0155277 A1 | 7/2006 | Metz-Stavenhagen | |
| 2006/0173456 A1 | 8/2006 | Hawkes et al. | |
| 2006/0241595 A1 * | 10/2006 | Molz et al. | 606/61 |
| 2006/0247636 A1 | 11/2006 | Yuan | |
| 2006/0293659 A1 | 12/2006 | Alvarez | |
| 2006/0293664 A1 | 12/2006 | Schumacher | |
| 2007/0016200 A1 | 1/2007 | Jackson | |
| 2007/0043358 A1 * | 2/2007 | Molz et al. | 606/61 |
| 2007/0055244 A1 * | 3/2007 | Jackson | 606/61 |
| 2007/0088357 A1 | 4/2007 | Johnson | |
| 2007/0090238 A1 | 4/2007 | Justis | |
| 2007/0123870 A1 | 5/2007 | Jeon | |
| 2007/0135817 A1 | 6/2007 | Ensign | |
| 2007/0161999 A1 * | 7/2007 | Biedermann et al. | 606/61 |
| 2007/0167949 A1 | 7/2007 | Altarac et al. | |
| 2007/0225711 A1 * | 9/2007 | Ensign | 606/61 |
| 2007/0250064 A1 | 10/2007 | Darois | |
| 2007/0270880 A1 | 11/2007 | Lindemann | |
| 2007/0288004 A1 | 12/2007 | Alvarez | |
| 2008/0249570 A1 | 10/2008 | Carson et al. | |
| 2008/0294202 A1 * | 11/2008 | Peterson et al. | 606/305 |
| 2009/0149887 A1 | 6/2009 | Schlaepfer et al. | |
| 2009/0198289 A1 | 8/2009 | Spratt et al. | |
| 2009/0270916 A1 * | 10/2009 | Ramsay et al. | 606/246 |
| 2010/0145394 A1 | 6/2010 | Harvey et al. | |
| 2010/0152787 A1 * | 6/2010 | Walsh et al. | 606/308 |
| 2010/0198272 A1 | 8/2010 | Keyer et al. | |
| 2011/0213424 A1 | 9/2011 | Biedermann et al. | |
| 2011/0230917 A1 | 9/2011 | Carson et al. | |
| 2011/0270325 A1 | 11/2011 | Keyer et al. | |

(56) References Cited

U.S. PATENT DOCUMENTS

FOREIGN PATENT DOCUMENTS

| | | |
|---|---|---|
| EP | 1316295 A2 | 6/2003 |
| EP | 1323391 A2 | 7/2003 |
| JP | 2006-525102 | 11/2006 |
| WO | WO 97/02786 | 1/1997 |
| WO | WO 98/52482 A1 | 11/1998 |
| WO | WO 00/21455 | 4/2000 |
| WO | WO 02/076314 A1 | 10/2002 |
| WO | WO 2006/116437 A2 | 11/2006 |
| WO | WO 2007/038350 A | 4/2007 |
| WO | WO 2007/047711 A2 | 4/2007 |
| WO | WO 2007/146032 A2 | 12/2007 |
| WO | WO 2008/089096 A2 | 7/2008 |
| WO | WO 2009/015100 A3 | 1/2009 |
| WO | WO 2010/028287 A3 | 3/2010 |

OTHER PUBLICATIONS

International Patent Application No. PCT/US2008/070670: International Preliminary Report on Patentability, 11 pages.

Aebi et al., "AO ASIF Principles in Spine Surgery", Springer, © 1998, 7 pages.

* cited by examiner

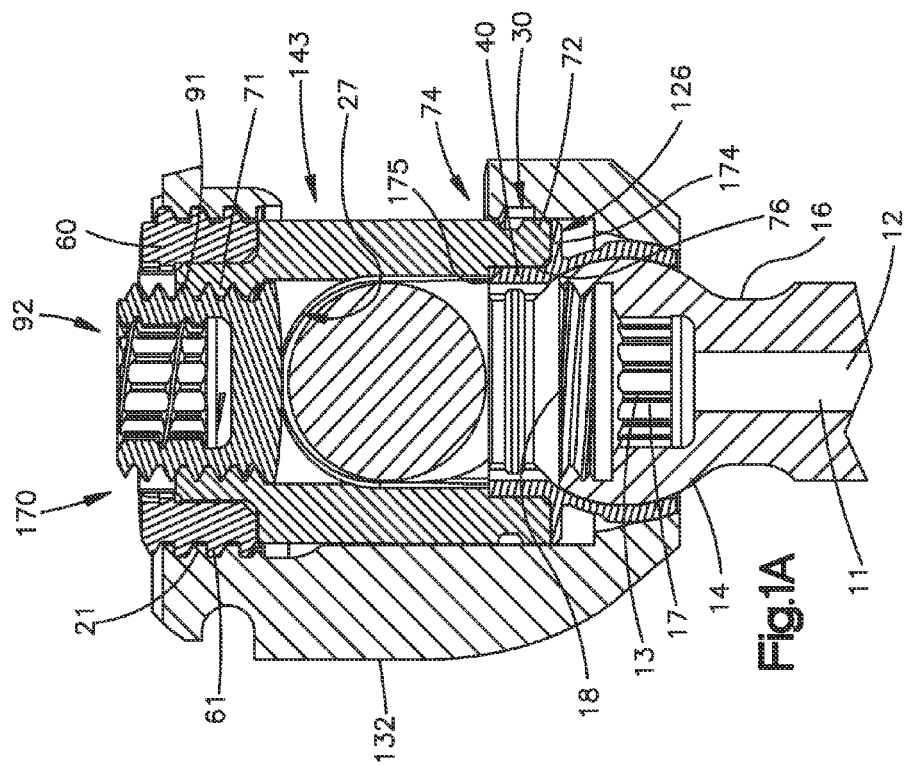
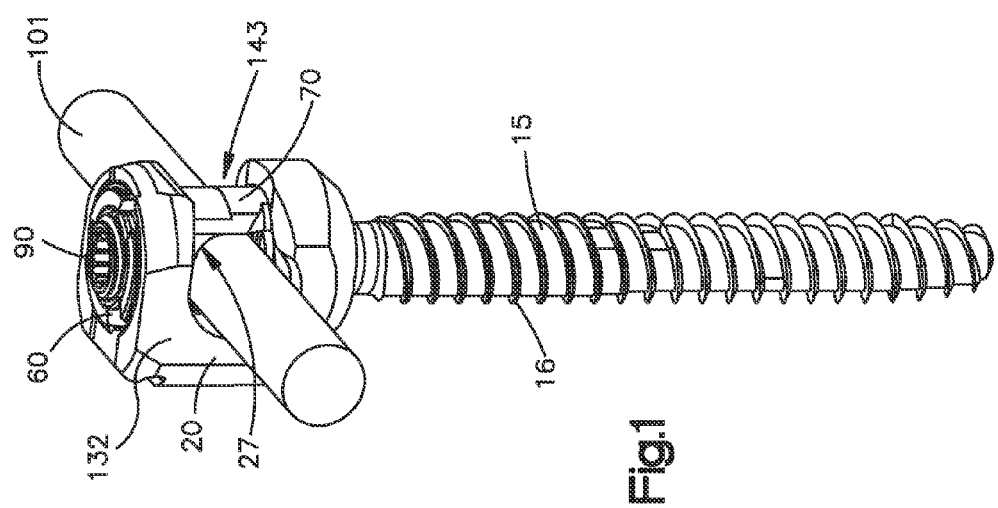

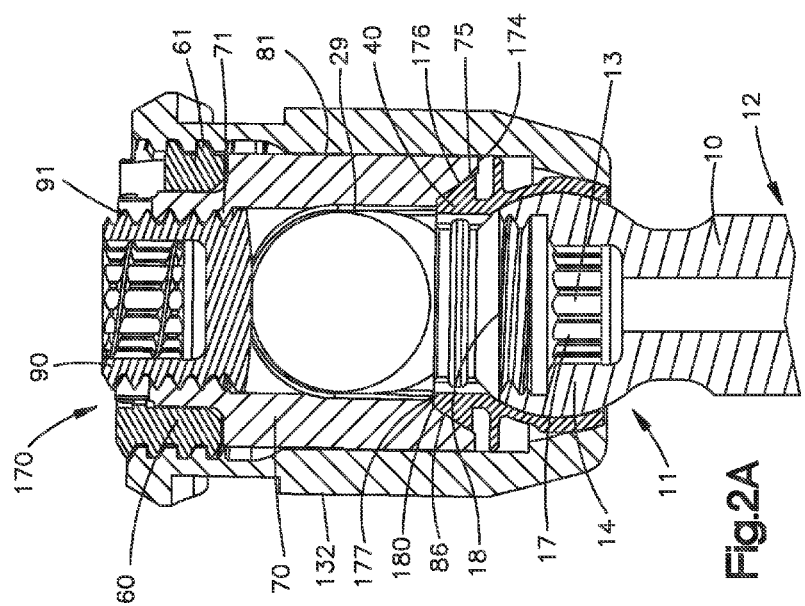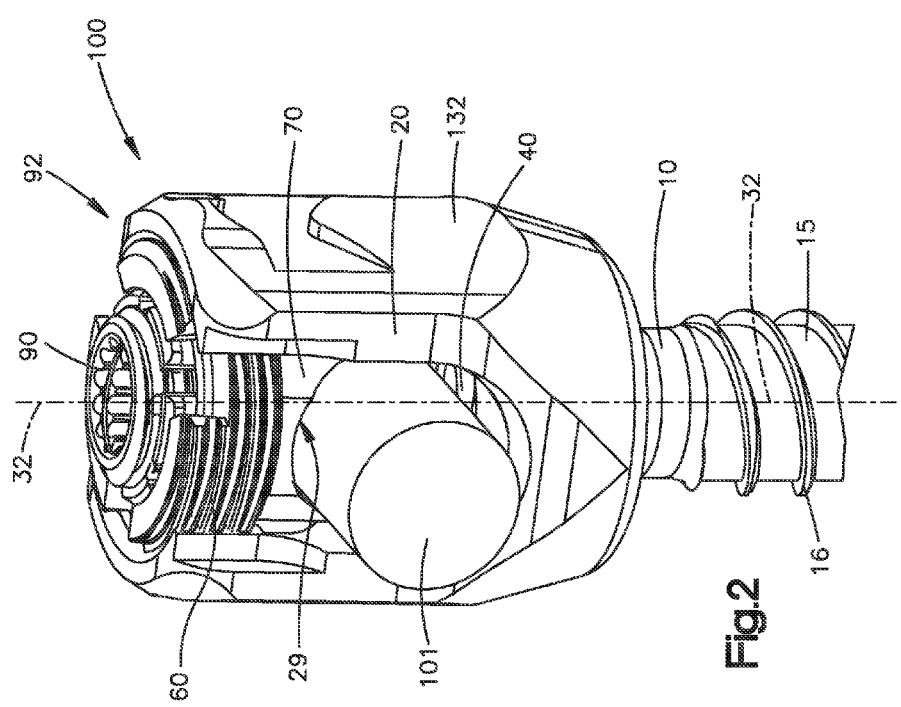

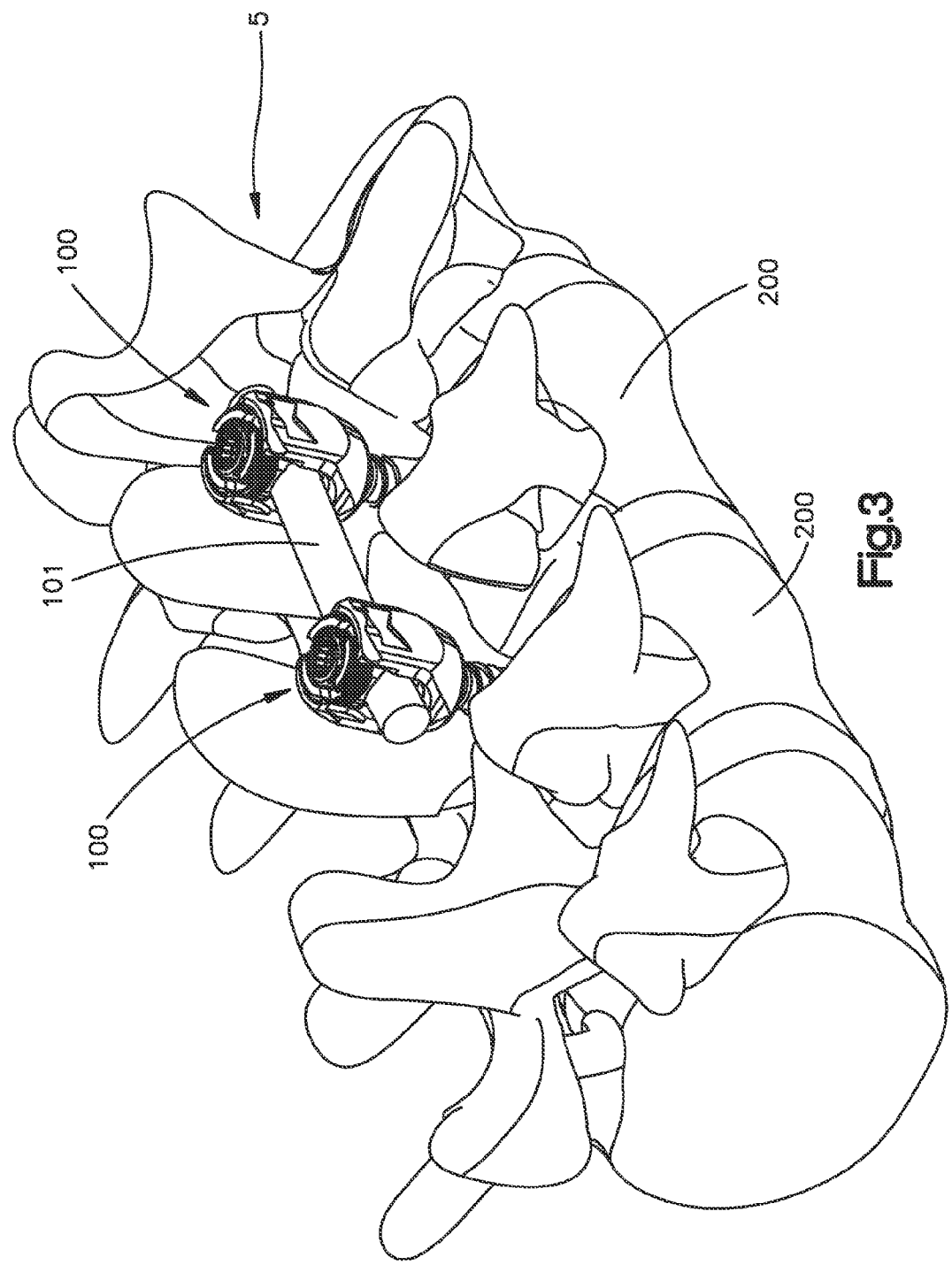

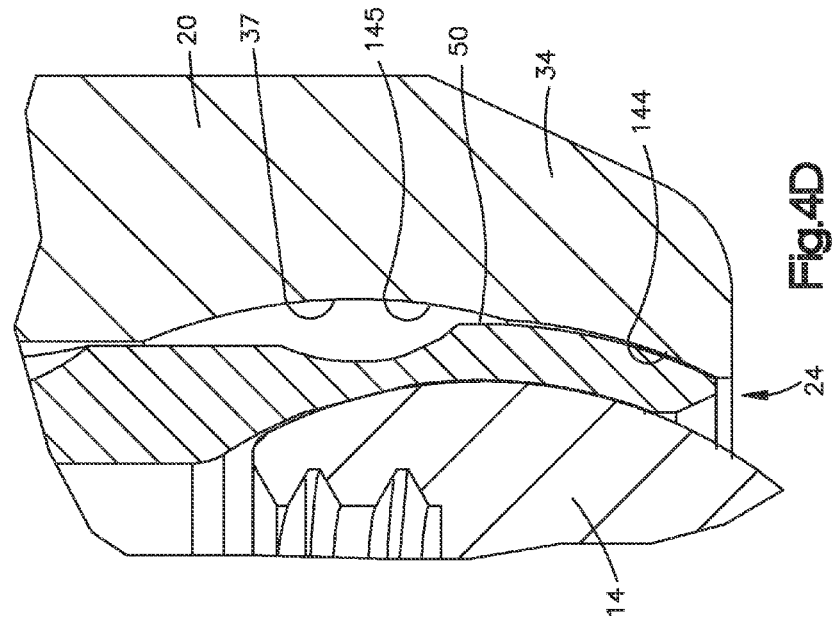
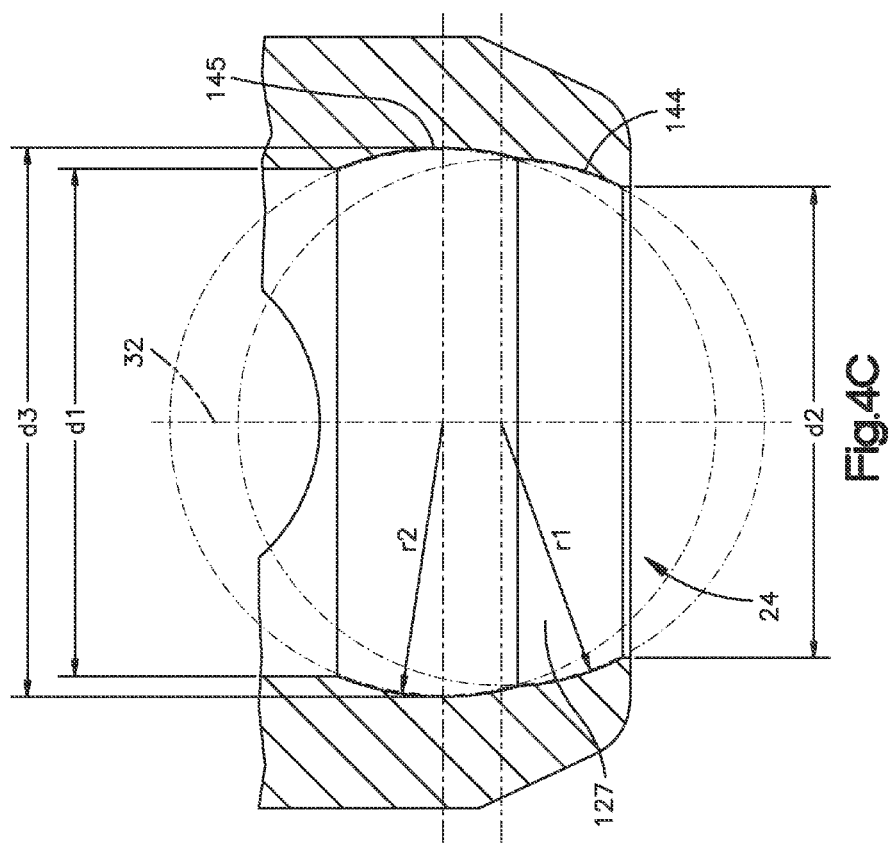

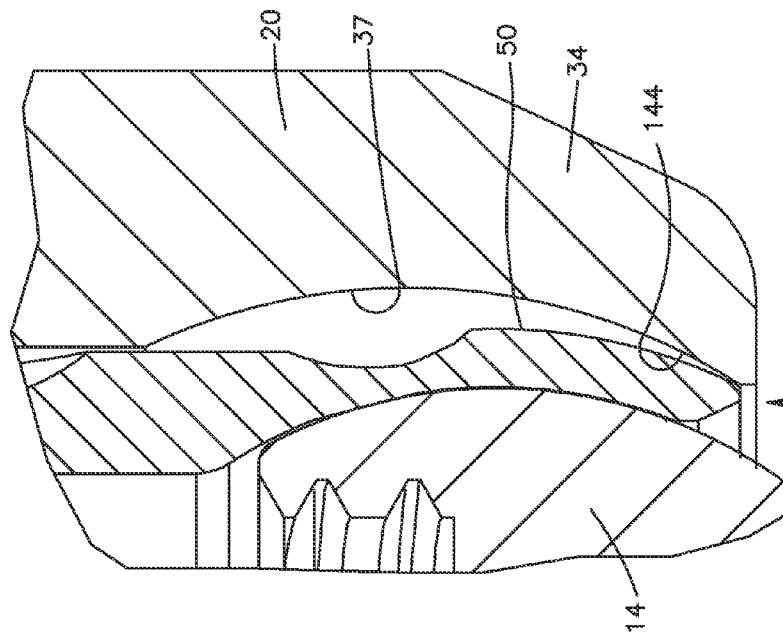
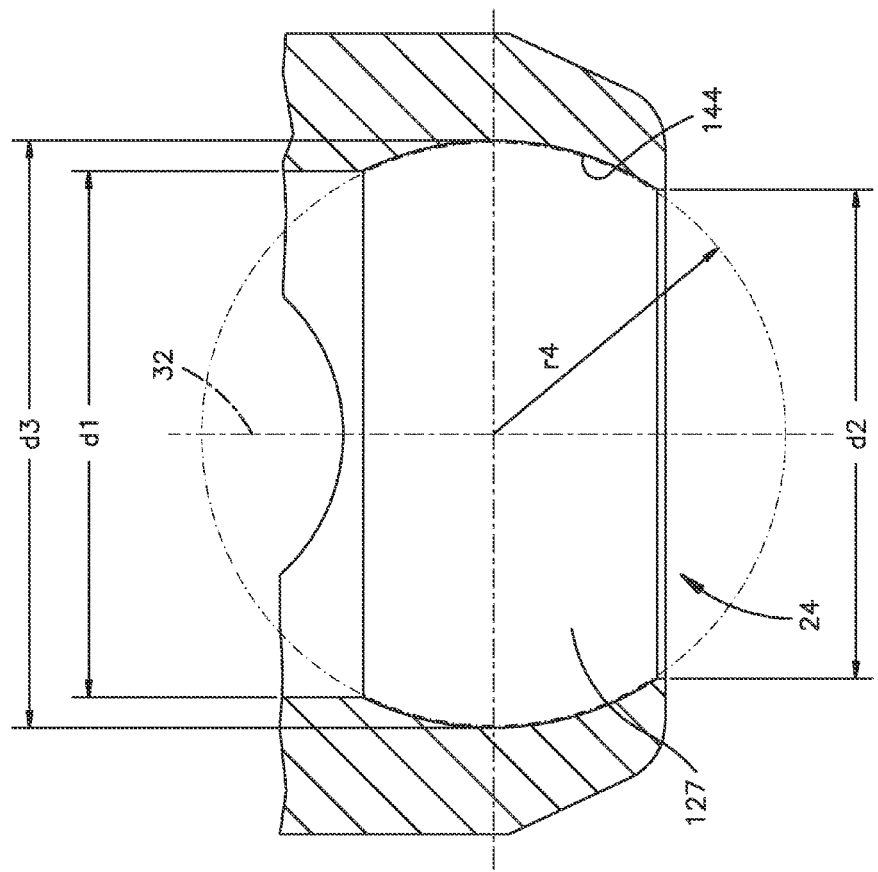

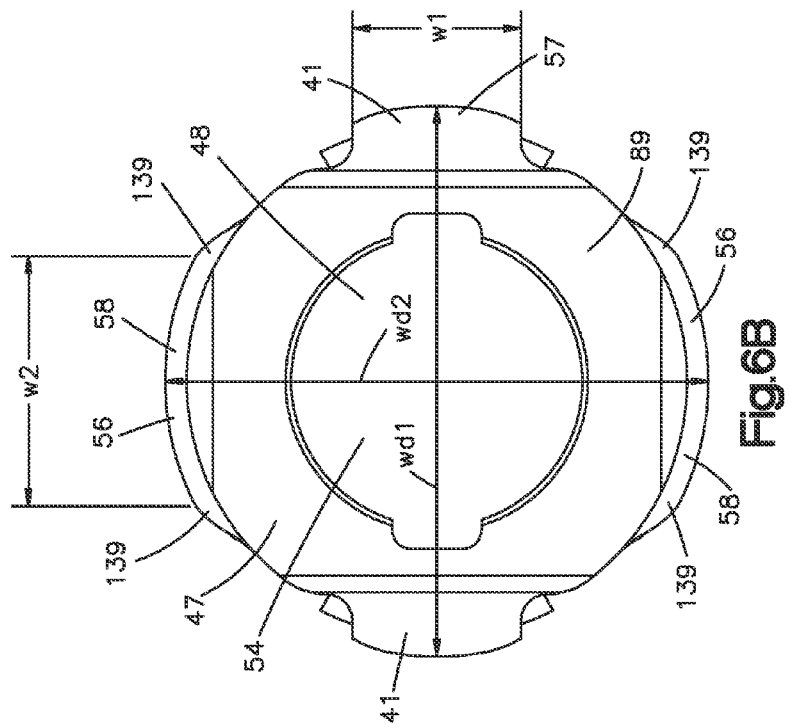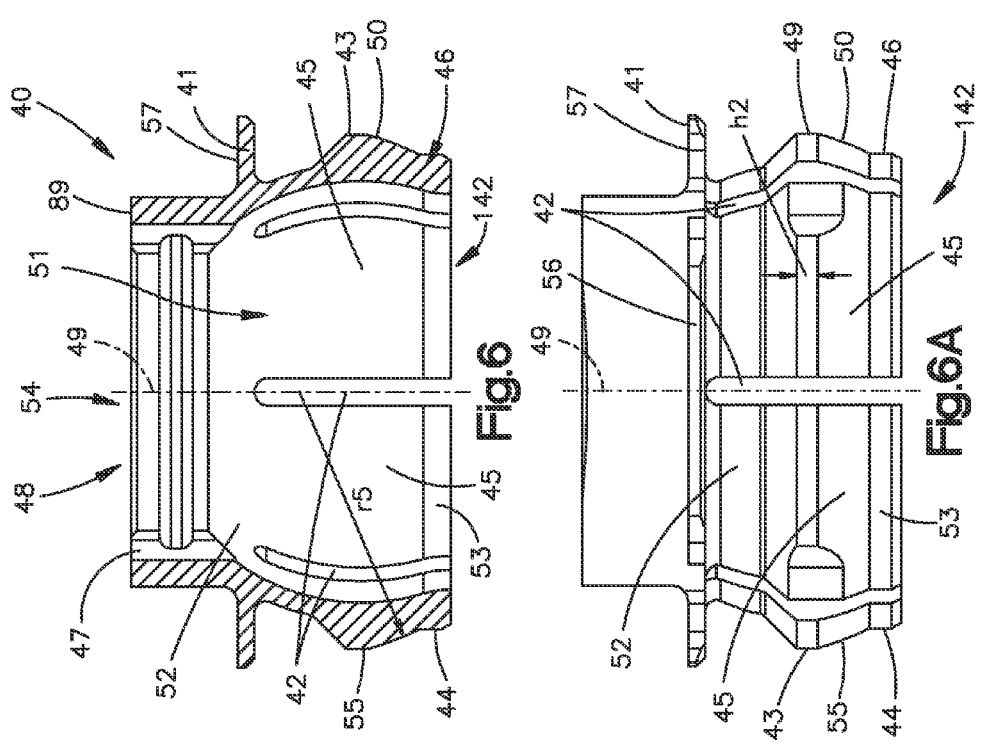

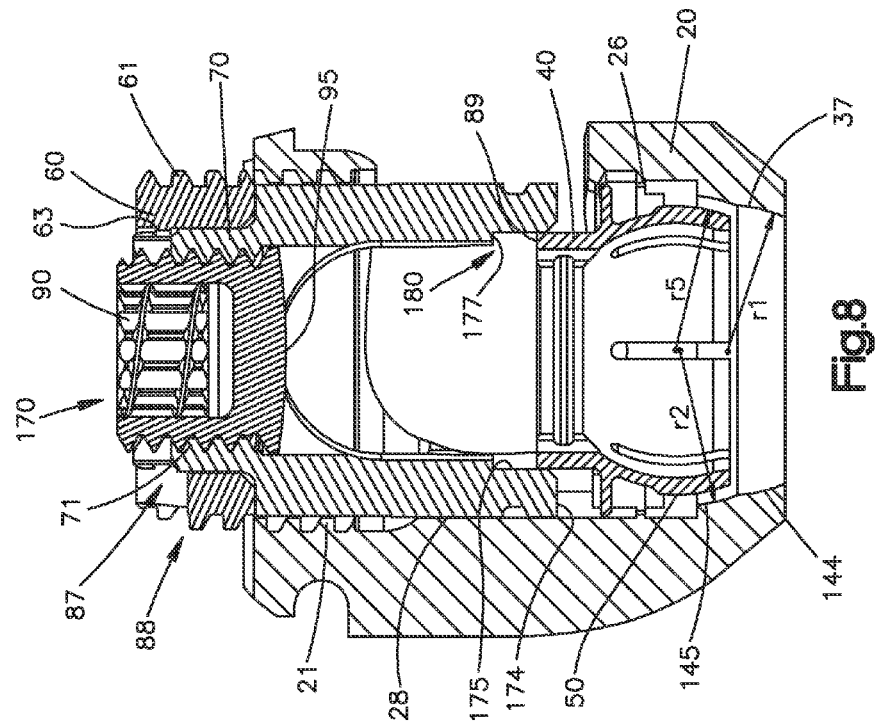
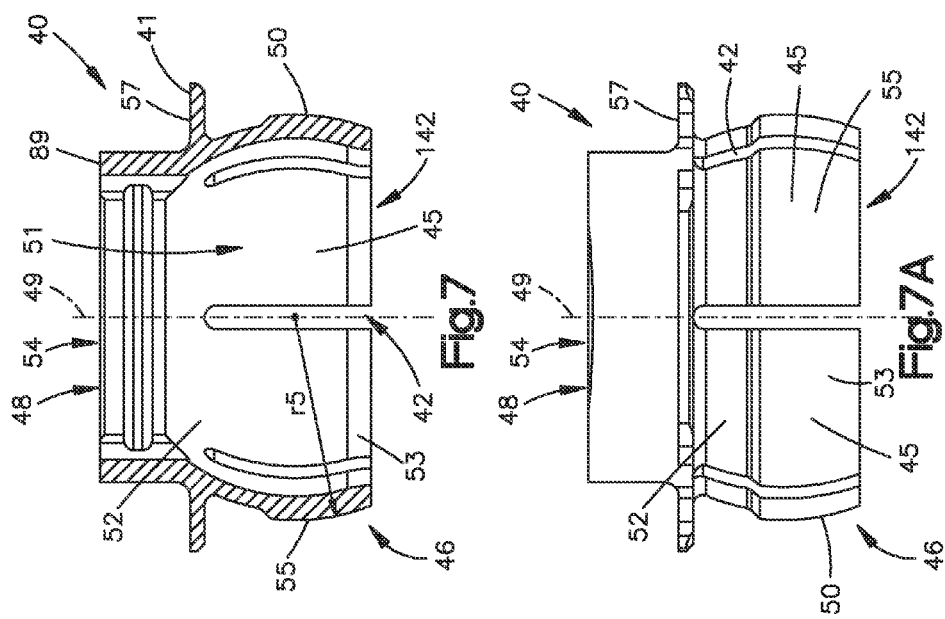

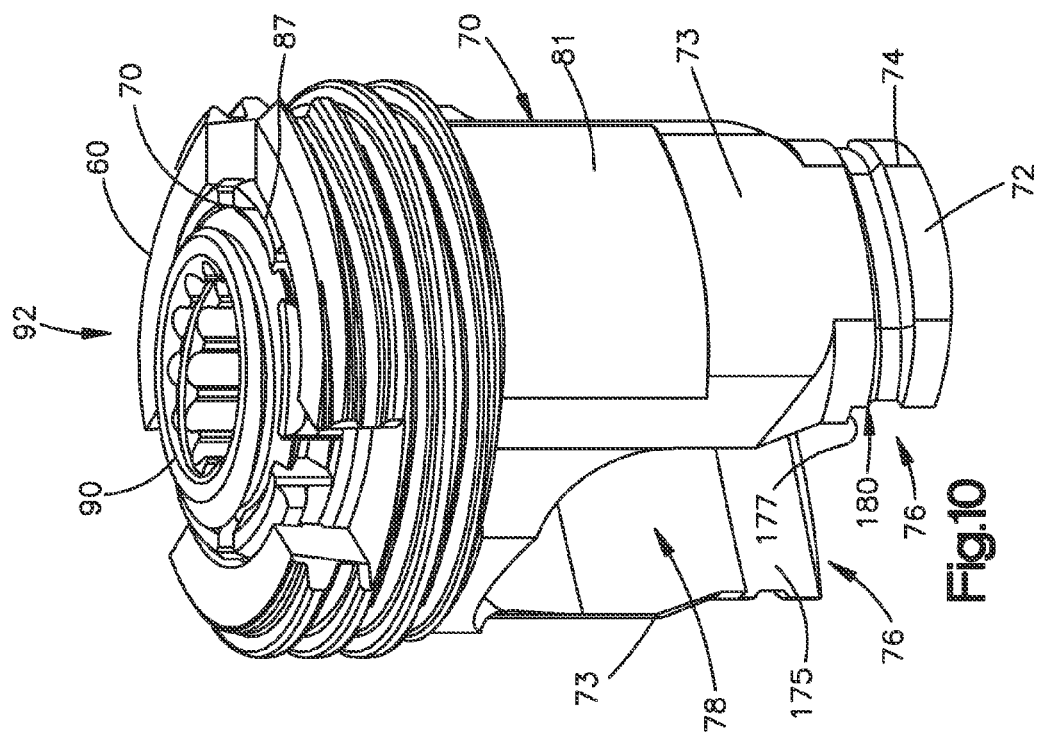
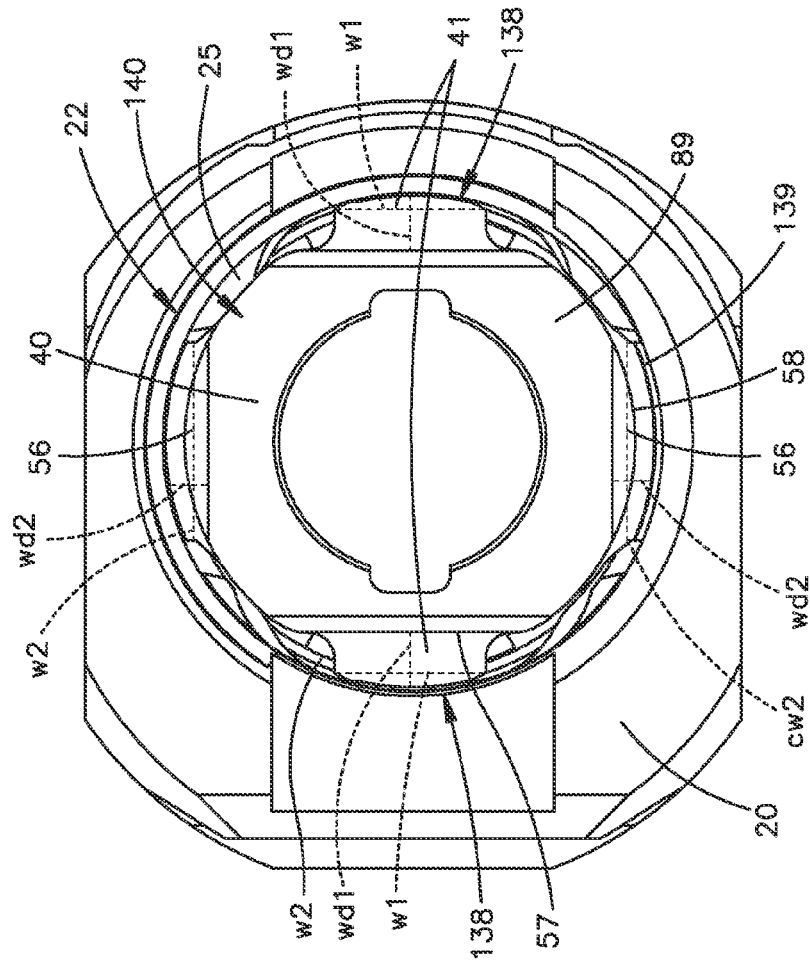

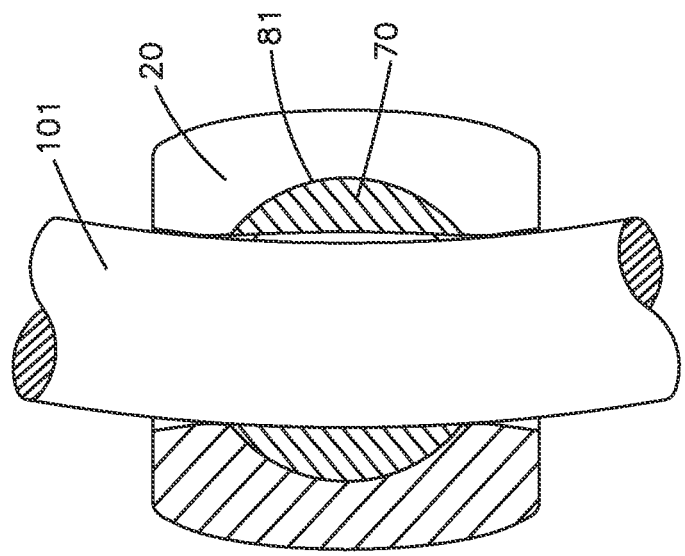
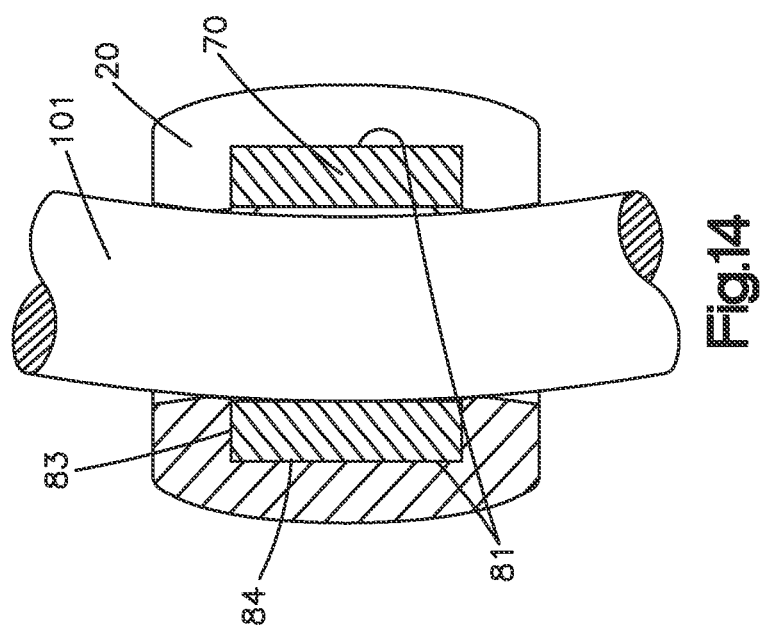

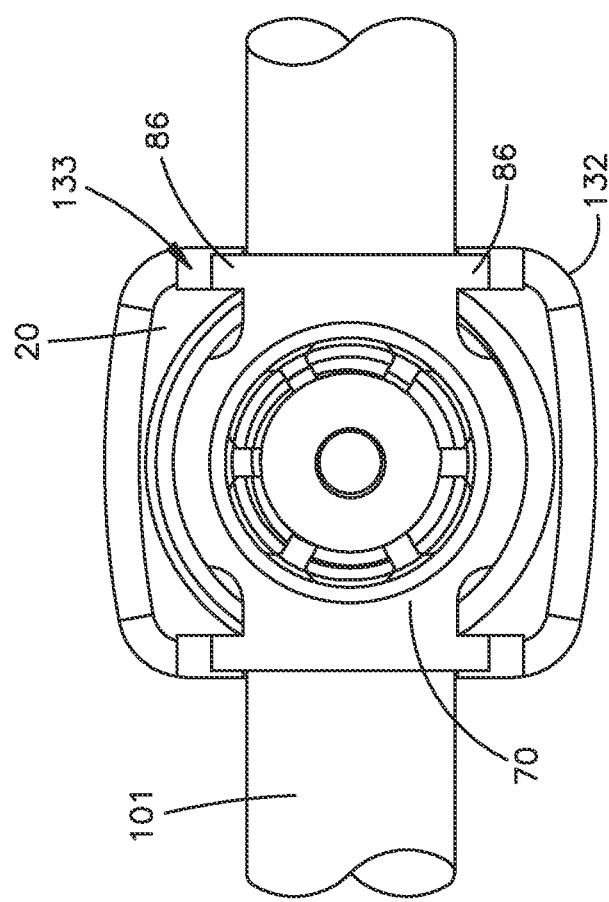

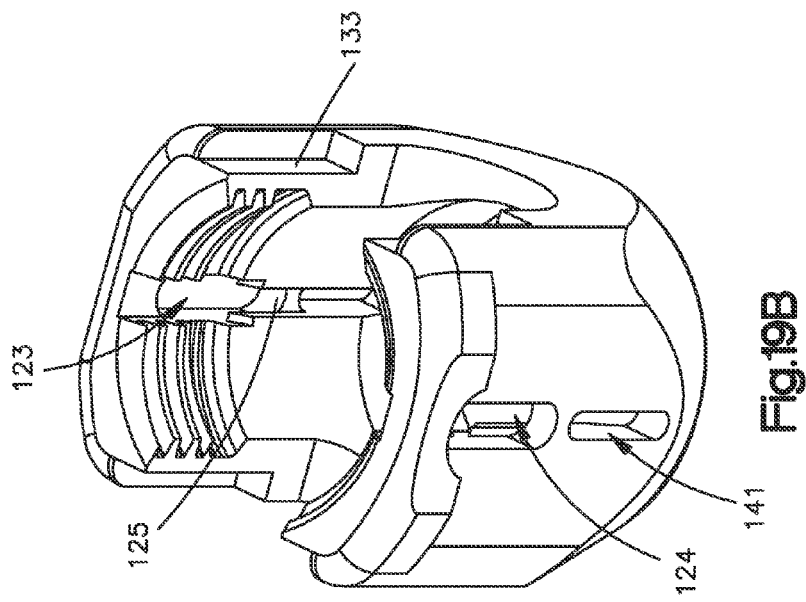
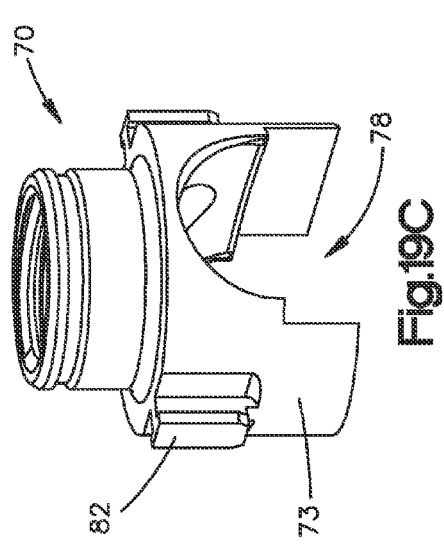
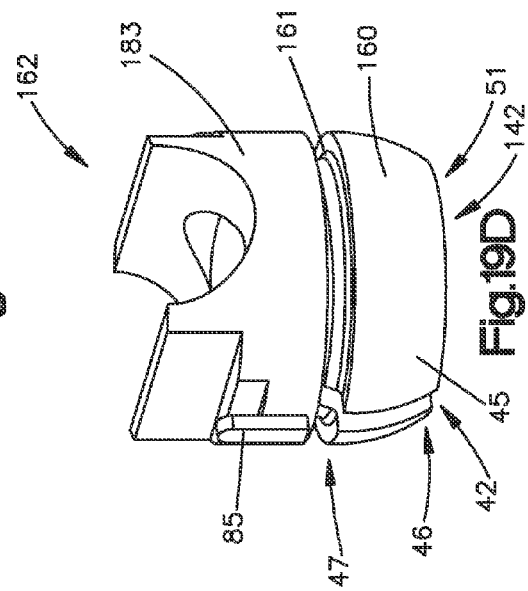

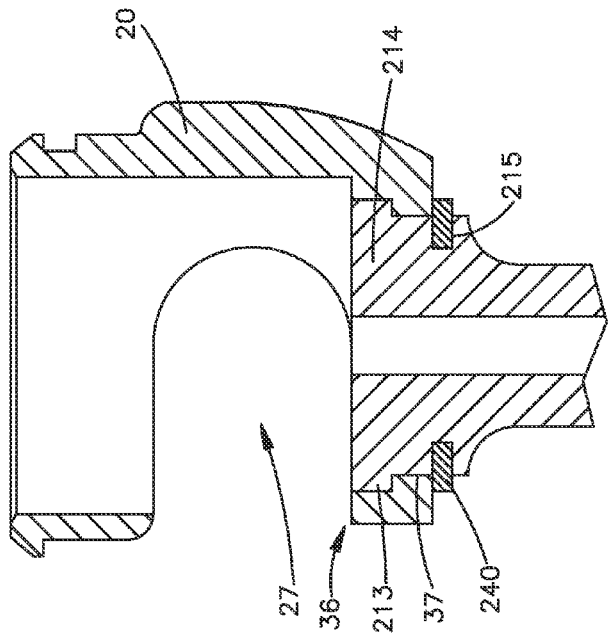
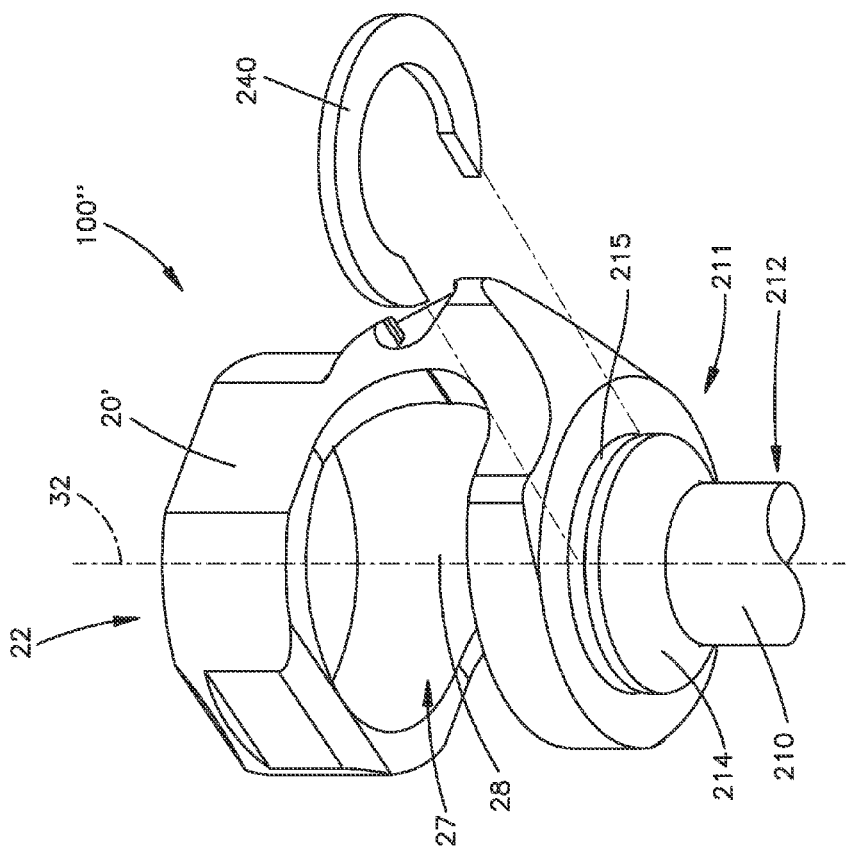
Fig.21A
Fig.21

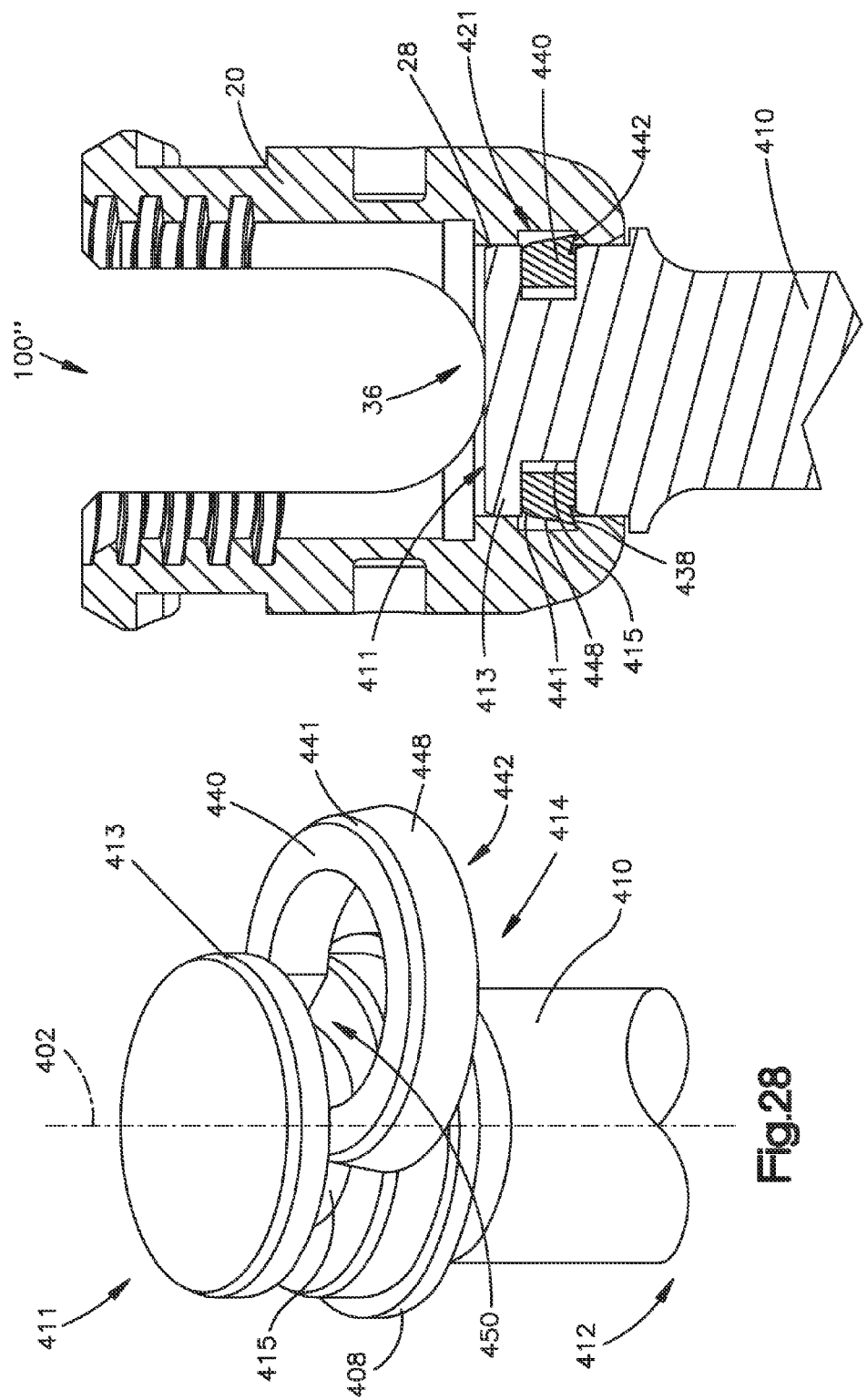

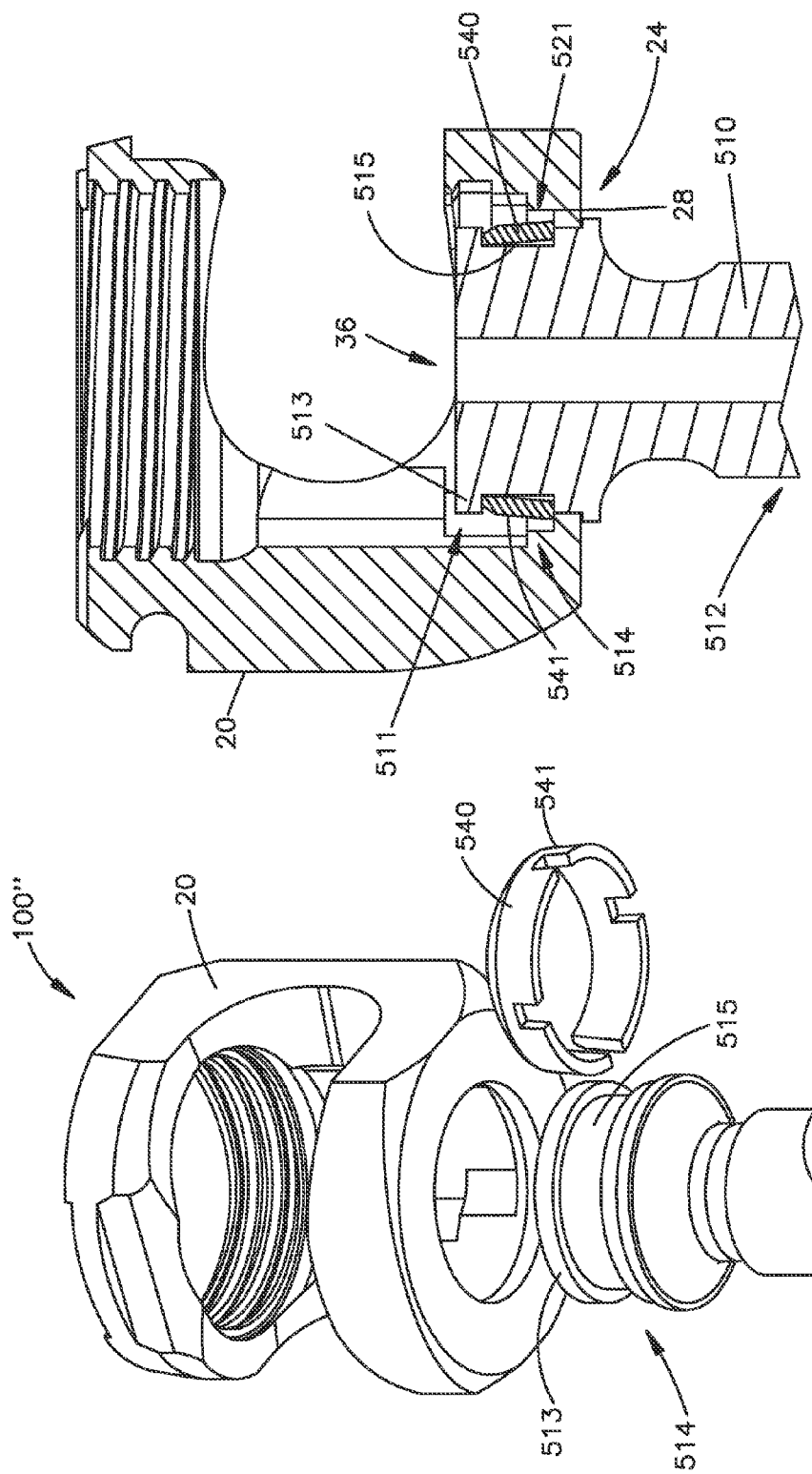

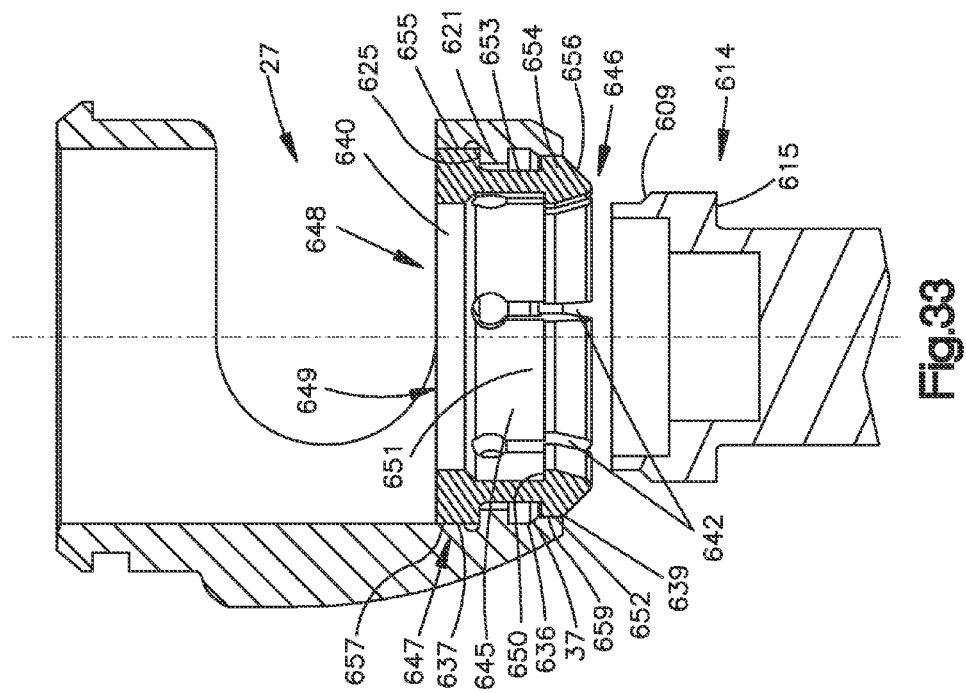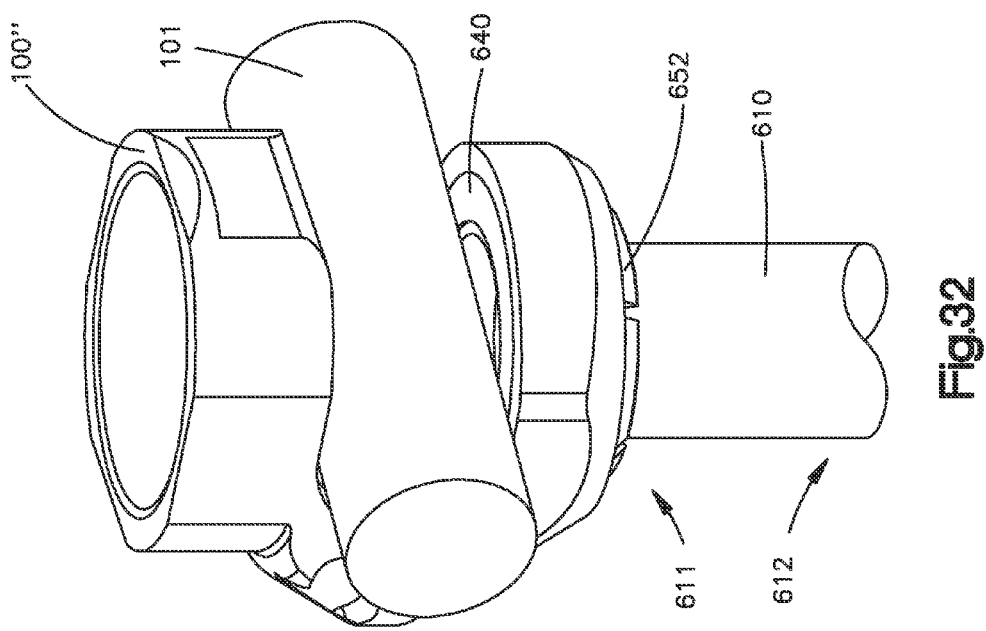

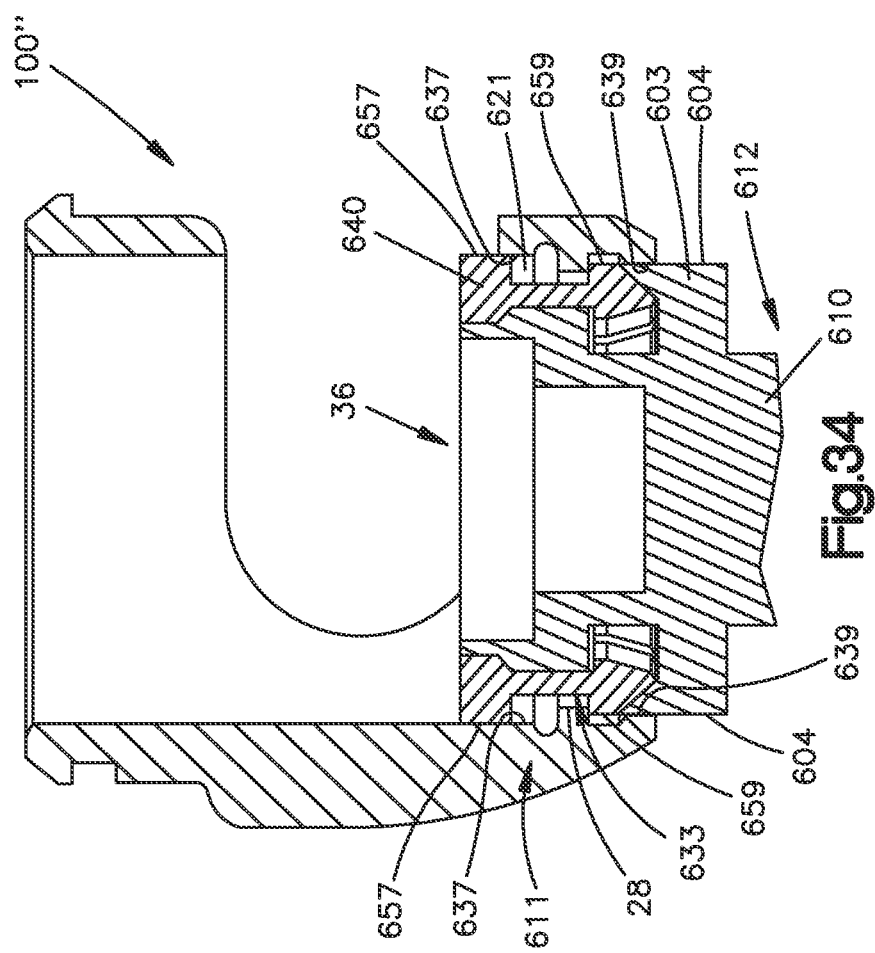

BONE FIXATION ASSEMBLY

CROSS-REFERENCE TO RELATED APPLICATIONS

This application is the National Stage of International Application No. PCT/US2009/056100, filed Sep. 4, 2009, which claims the benefit of U.S. Provisional Application No. 61/094,622, filed Sep. 5, 2008, the disclosures of which are incorporated herein by reference in their entireties for all purposes.

BACKGROUND OF THE INVENTION

It is often necessary due to various spinal disorders to surgically correct and stabilize spinal curvatures, or to facilitate spinal fusion. Numerous systems for treating spinal disorders have been developed.

One method involves a bone fixation system including a pair of elongated members, typically spinal rods, longitudinally placed on the posterior spine on either or both sides of the spinous processes of the vertebral column. Each rod is attached to various vertebrae along the length of the spine by way of bone fixation or bone anchor assemblies, e.g. pedicle screws. The body of the pedicle screw often has a rod-receiving channel and receives a locking cap to secure the spinal rod to the pedicle screw.

To facilitate insertion of the spinal rod into the rod-receiving channels of the pedicle screws, pedicle screws have been developed wherein the body is separate from and pivotable with respect to the bone anchor (commonly known as polyaxial pedicle screws).

It is desirable to develop a bone fixation system and assemblies that are simple for a surgeon to use.

SUMMARY OF THE INVENTION

The present invention relates generally to orthopedics. More specifically, the present invention relates to a bone fixation system (also referred to as a bone anchor system) including a bone fixation assembly (also referred to as a bone anchor assembly) having a spinal rod-receiving channel and an associated method for implanting the bone fixation system and bone fixation assembly.

The present invention is directed to a bone anchor assembly for use in a spinal fixation procedure that connects a support member (e.g., a spinal rod) to a vertebra. The anchor assembly preferably includes a bone anchor having an enlarged head portion (e.g., a bone screw), an insert member (e.g., a bushing), a body having a bore for receiving the insert member and a rod receiving channel, and a locking cap engagable with the body and preferably having a saddle for receiving the spinal rod. The bone anchor assembly preferably enables in-situ assembly. That is, the anchor assembly is preferably configured so that in use, the bone anchor may be secured to the patient's vertebra prior to being connected to the body. Accordingly, the anchor assembly preferably enables a surgeon to implant the bone anchor without the body and bushing to maximize visibility and access around the anchoring site. Once the bone anchor has been secured to the patient's vertebra, the body can "pop-on" to the bone anchor.

In one preferred embodiment, the anchor assembly includes bone anchor moveable with respect to a body subassembly prior to fixing the position of the spinal support member to the body subassembly. The body subassembly is preferably sized and configured to snap onto the head of the bone anchor and may include an insert member (e.g., a bushing), and receives a locking cap preferably with a saddle. The bone anchor preferably includes an enlarged head portion. The head portion preferably includes a first tool interface for engaging a first surgical instrument operatively associated with the bone anchor. The body preferably includes a longitudinal axis, an interior wall, an upper end with an upper opening, a lower end with a lower opening, a bore extending between the upper opening and the lower opening, and a rod-receiving channel. The rod-receiving channel is preferably configured and arranged to receive a spinal rod.

The bushing preferably includes an upper, rod-facing portion with an upper end, and a lower portion that captures and at least partially surrounds the head portion of the bone anchor. The lower portion of the bushing includes at least one, preferably a plurality of, slot(s) extending from the lower end, the slots preferably defining a plurality of flexible aims, wherein each of the flexible arms have an outer surface. In the case of a multi-piece bushing, the slots in the lower portion may extend either from the lower end with optionally one slot extending all the way to the upper end of said lower portion, or alternatively the slots extending from both the lower end and the upper end of the lower portion with optionally one slot extending all the way from the upper to the lower end. The bushing is preferably movably positionable within the bore of the body.

The locking cap preferably includes a saddle and a locking means or locking assembly. The saddle has a plurality of saddle arms defining a saddle rod-receiving channel, and configured and arranged to be received within the bore of the body to retain the spinal rod. The locking means or locking assembly may include either a locking element or assembly that simultaneously locks the bushing and the spinal rod, or a locking element or assembly to lock the bushing separately from the rod, where the element or assembly locking the bushing is operatively associated with the saddle. The locking element or assembly locking the bushing is preferably movably engagable with the body from an unlocked position to a locked position, wherein movement of the locking element or locking assembly from the unlocked position to the locked position urges the saddle, which in turn urges the bushing and the flexible bushing arms against the lower portion of the body to secure and fix the position of the bone anchor relative to the body. In the case of simultaneous locking of the bushing and rod, the locking element or assembly urges the saddle against the rod, which in turn urges the bushing into a locked position. In the case of separate locking of the bushing and the rod, the locking element or locking assembly which locks the bushing preferably urges the saddle against the upper end of the bushing, which in turn urges the bushing into the locking position. The locking element to separately lock the rod with respect to the body is preferably connected to and received in the element that connects to the body (e.g. threaded ring), or is connected to and received in the saddle. The locking element to separately lock the rod may include a one-piece set screw or a two-piece set screw with a saddle attached to the lower end of the set screw, or other configurations.

In another preferred embodiment the bone anchor assembly for use with a spinal rod for stabilizing bones or bone fragments is provided which includes a bone anchor, a body, an insert member receivable in the body, and a locking cap assembly. The bone anchor may have an enlarged, curvate head portion, and may connect to the bone or other substrate using threads, hooks, clamps, stakes, tacks, pins, spikes or other means.

The body preferably has a longitudinal axis, an exterior sidewall, an interior wall, an upper end with an upper opening, a lower end with a lower opening, a bore having an interior wall, and a rod-receiving channel. The bore of the body preferably extends substantially between the upper opening and the lower opening and the rod-receiving channel is preferably configured and arranged to receive the spinal rod. In one embodiment, often referred to as a side-loading bone anchor assembly, the rod-receiving channel extends into the bore of the body from the exterior side wall of the body, and in another embodiment, often referred to as a top-loading bone anchor assembly, the rod-receiving channel extends downward from the upper end in the direction of the longitudinal axis and communicates with the upper opening.

The insert member in one embodiment is preferably a bushing. The bushing preferably has a first end, a second end, a lower opening, an interior cavity and at least one slot extending from the second end, the slot permitting the bushing to be expandable and collapsible. The bushing further has an outer surface and is movably positionable within the bore of the body. The outer surface of the bushing preferably has at least a portion that is frusto-spherical in shape. The outer surface of the bushing may further have at least one cylindrical zone where the surface in the cylindrical zone has a substantially constant diameter in its undeflected state, and wherein the lower end of the body has a chamber having a substantially cylindrical surface where the diameter is substantially constant, wherein the bushing is positionable so that the at least one cylindrical zone is oppositely facing the cylindrical surface of the body to inhibit the bushing from angulating in the body.

The bushing may be a single piece element or a multi-piece element. In the multi-piece bushing embodiment, the bushing may have a lower insert member for receiving the head portion of the bone anchor, and an upper sleeve member. The lower insert member preferably has an outer surface at least a portion of which is frusto-spherical and further has at least one slot and is expandable and compressible. The sleeve member preferably is interconnected to the lower insert member, the sleeve member preferably having a rod-receiving channel.

The locking cap assembly preferably includes a saddle and a locking element, the saddle having at least one saddle arm defining a rod receiving channel, and configured and arranged to be received within the bore of the body to retain the spinal rod, wherein the saddle is operatively associated with the locking element and the bushing, the locking element being engagable with the body and movable from an unlocked position to a locked position. Movement of the locking element from the unlocked position to the locked position when the spinal rod is received in the rod-receiving channel applies pressure to the spinal rod to secure or lock the position of the spinal rod with respect to the body. The bone anchor preferably is poly-axially rotatable with respect to the body when the locking cap assembly is in the unlocked position.

The body and insert member may incorporate one or more features to assist in the operation and assembly of the bone anchor assembly. In one preferred embodiment, the insert member preferably may further include at least one wing extending from an outer surface of the insert member and the body may further include at least one wing projection extending longitudinally on the interior wall in the body bore and a first stop disposed in the bore above at least a portion of the at least one wing projection. The first stop preferably is configured and arranged to contact the at least one wing to restrict the upward movement of the insert member within the bore of the body, and the at least one wing projection preferably is configured and arranged to prevent the insert member from rotating in selected areas of the bore of the body. The bore of the body may further have a first zone and a second zone, the first zone including both the first stop and the at least one wing projection such that the insert member is not permitted to rotate within the first zone. The second zone may be located below the first zone and the insert member is permitted to expand and rotate in the second zone.

The bore of the body may further include an enlarged chamber which permits the arms of the insert member to expand in order to receive the head portion of the bone anchor when it is inserted through the lower end opening of the body. The first stop may be configured to prevent the insert member from extending up the body bore when the bone anchor is inserted into the body so that the arms of the insert member remain in the enlarged portion of the body bore, and wherein the at least one wing is located in the first zone during insertion of the head portion into the cavity of the insert member and the expandable portion of the insert member is located in the second zone. The body preferably may further include a second stop disposed in the first zone below the first stop, wherein the second stop is constructed and arranged to restrict the movement of the insert member within the body by interfering with the at least one wing.

In yet a further embodiment, the insert member may be a bushing that preferably includes a plurality of slots extending from the second end, the slots defining a plurality of flexible arms, wherein the arms have an outer surface at least a portion of which is frusto-spherical. The bushing may further include at least a first wing and at least a second wing on the outer surface of the bushing, the first wing having a wider width than the second wing and preferably extending outward from the outer surface of the bushing a smaller distance than the second wing. The body bore preferably has a chamber in the lower end including an interference zone and a rotational zone, the interference zone having at least two wing projections extending longitudinally and at least two first stops positioned above at least a portion of the wing projections and forming a first channel and a second channel, the first channel being of larger width than the second channel. The bushing first wings preferably can extend down the first channel without interference while the bushing second wings cannot extend move within the first channel without abutting at least one of the first stops.

The locking cap assembly may take several configurations. In some embodiments of the locking cap assembly the bone anchor and spinal rod may be separately locked where as in other embodiments the bone anchor and spinal rod may be simultaneously locked. In one embodiment which permits separate locking of the spinal rod and bone anchor, the locking cap assembly includes a locking ring element, a saddle and a setscrew element. The locking ring preferably is engagable with the body and operatively associated with the saddle. The locking ring element preferably is movable from a ring unlocked position to a ring locked position, wherein movement of the locking ring element from the ring unlocked position to the ring locked position causes the saddle to move downward within the body, which in turn moves the bushing downward in the body, causing the bushing to contact the interior wall of the bore of the body causing the bushing to collapse around and fix the position of the bone anchor with respect to the body. The set screw element may be engagable with the locking ring element and movable from a screw unlocked position to a screw locked position, wherein movement of the set screw element from the screw unlocked position to the screw locked position when the spinal rod is received in the rod receiving channel fixes the position of the spinal rod with respect to the body.

In a different embodiment which permits separate locking of the bone anchor and the spinal rod, the locking cap assembly may also include locking ring element engagable with the body and operatively associated with the saddle, and a set-screw element. The locking ring element preferably is movable from a ring unlocked position to a ring locked position, wherein movement of the locking ring element from the ring unlocked position to the ring locked position when the bone anchor is received within the body fixes the bone anchor with respect to the body. The set screw element preferably is engagable with the saddle and movable from a screw unlocked position to a screw locked position, wherein movement of the set screw element from the screw unlocked positioned to the screw locked position when the spinal rod is received in the rod receiving channel fixes the position of the spinal rod with respect to the body.

The bone anchor assembly may incorporate features in the saddle and body to assist in its operation and manufacture. In one embodiment, the body includes a lower body recess formed in the bore at the lower end, and at least one saddle arm is sized and dimensioned to extend past the spinal rod such that the distal end of the saddle arm is receivable in the lower body recess and contacts the bushing when the locking ring is engaged with the body. The saddle may also be configured and sized and the bore in the body may be configured and sized such that the at least one saddle arm is form-fitted within the body when placed into the bore of the body. The at least one saddle arm may have at least one side surface perpendicular to at least one back surface, and the bore of the body may have cooperating perpendicular surfaces, wherein the at least one saddle arm is close-fitted within the bore of the body such that any rotation or twisting deflection of the body is transferred to the saddle arm.

One of the saddle arms may also include an oblique bushing interface surface having an inclined surface at its distal end, and the bushing has an oblique saddle interface surface having an inclined surface, wherein the inclined surface of the bushing is configured and arranged to contact the inclined surface of the saddle when the locking element is in the locked position. One of the saddle arms may include a perpendicular bushing interface surface having a surface at its distal end that is perpendicular to its side surface, and the bushing may have a perpendicular saddle interface surface having a flat planar surface, and the perpendicular end surface of the bushing preferably is configured and arranged to contact the planar surface of the saddle when the locking element is in the locked position.

In one embodiment, the body may further include a recess formed on the interior wall in the bore and extending in the direction of the longitudinal axis from the upper end towards the lower end, and the saddle may further include a body engagement element, the body engagement element extending outward from the saddle and configured and arranged to engage the recess. The body may further include at least one external recess in the exterior side wall proximate the rod receiving channel and the saddle includes at least one wing extending outward from the saddle so that the at least one wing is configured and arranged to engage the external recess of the body.

In another preferred embodiment the anchor assembly includes a monorotational bone anchor, a body, a fastener element, and a locking cap. The bone anchor includes a bone anchor upper portion and a bone anchor lower portion. The bone anchor upper portion includes a head portion and at least one head engagement element, wherein the head portion may include a first tool interface for engaging a first surgical instrument. The body includes a longitudinal axis, an upper end with an upper opening, a lower end with a lower opening, a bore extending substantially between the upper opening and the lower opening, a rod receiving channel constructed and arranged to receive a spinal rod, and at least one body engagement element disposed in the bore proximate the lower end. The fastener element, which may be a "C-clip", spring clip, bushing, or any other retaining element constructed and arranged to be engagable with the at least one head engagement element to secure the bone anchor to the body, preferably as the body is attached to the bone anchor after insertion of the bone anchor into bone by inserting the head of the bone anchor up through lower opening in the body. The locking cap includes a saddle and a locking element. The saddle has a plurality of saddle arms defining a saddle rod-receiving channel and is constructed and arranged to be received within the bore of the body to retain the spinal rod within the body. The saddle is also operatively associated with the locking element, which is engagable with the body, wherein the locking element is movable from an unlocked position to a locked position. The movement of the locking element from the unlocked position to the locked position when the spinal rod is received in the rod-receiving channel secures the spinal rod with respect to the body.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. The preferred embodiments of a bone anchor system including a bone anchor assembly are shown in the drawings for the purposes of illustration. It should be understood, however, that the application is not limited to the precise arrangements, structures, features, embodiments, instrumentalities, and methods shown and described, and the arrangements, structures, features, embodiments, instrumentalities, and methods shown and described may be used singularly or in combination with other arrangements, structures, features, embodiments, instrumentalities, and methods. In the drawings:

FIG. 1 illustrates a side perspective view of a first embodiment of a bone anchor assembly configured with a side-loading, rod-receiving channel, in accordance with the present invention;

FIG. 1A illustrates a side cross-sectional view of the anchor assembly of FIG. 1;

FIG. 2 illustrates a side perspective view of a second embodiment of an anchor assembly configured with a top-loading, rod-receiving channel, in accordance with the present invention;

FIG. 2A illustrates a side cross-sectional view of the anchor assembly of FIG. 2;

FIG. 3 illustrates a perspective view of a bone anchor system having a first anchor assembly and a second anchor assembly implanted into first and second vertebra with a spinal rod spanning the two vertebra;

FIGS. 4C-D illustrate magnified, side cross-sectional views of the lower portion of the body element of the anchor assembly of FIG. 4 with features removed for simplification;

FIGS. 4E-F illustrate magnified, side cross-sectional views of an alternate embodiment of the lower portion of the body element of the anchor assembly of FIG. 4 with features removed for simplification;

FIG. 6 illustrates a side cross-sectional view of the bushing element of FIG. 5;

FIG. 6A illustrates a side view of the bushing element of FIG. 6;

FIG. 6B illustrates a top view of the bushing element of FIG. 6;

FIG. 7 illustrates a side cross-sectional view of the bushing element of FIG. 1A;

FIG. 7A illustrates a side view of the bushing element of FIG. 7;

FIG. 8 illustrates a side cross-sectional view of the bone anchor assembly of FIG. 1A with the bushing element in an unlocked or loading position;

FIG. 9 illustrates a top view of the body and bushing subassembly of FIG. 5;

FIG. 10 illustrates a perspective view of a three-piece locking cap shown in FIG. 1A;

FIG. 14 illustrates a top cross-sectional view of a saddle form-fitted in the body element in accordance with a preferred embodiment of the bone anchor assembly of the present invention;

FIG. 15 illustrates a top cross-sectional view of an alternative saddle form-fitted in the body element in accordance with a preferred embodiment of the bone anchor assembly of the present invention;

FIG. 18 illustrates a top view of the bone anchor assembly of FIG. 17;

FIG. 19B illustrates a perspective view of the body element of FIG. 19;

FIG. 19C illustrates a perspective view of the saddle element of FIG. 19;

FIG. 19D illustrates a perspective view of the sleeve and bushing element of FIG. 19A;

FIG. 21 illustrates a perspective view of a seventh embodiment of a bone anchor assembly in accordance with the present invention;

FIG. 21A illustrates a side cross-sectional view of the anchor assembly of FIG. 21;

FIG. 28 illustrates a perspective view of a screw and fastener element of a ninth embodiment of a bone anchor assembly in accordance with the present invention;

FIG. 29 illustrates a side cross-sectional view of the ninth bone anchor assembly of FIG. 28 including the screw and locking element in a locked position in the body element;

FIG. 30 illustrates a perspective view of a tenth embodiment of a bone anchor assembly in accordance with the present invention;

FIG. 31 illustrates a side cross-sectional view of the bone anchor assembly of FIG. 30;

FIG. 32 illustrates a side perspective view of an eleventh embodiment of a bone anchor assembly in accordance with the present invention;

FIG. 33 illustrates a side cross-sectional view of the bone anchor assembly of FIG. 32 prior to assembly of the screw; and FIG. 34 illustrates a twelfth embodiment of the bone anchor assembly in accordance with the present invention.

DETAILED DESCRIPTION OF THE INVENTION

Figure 4:
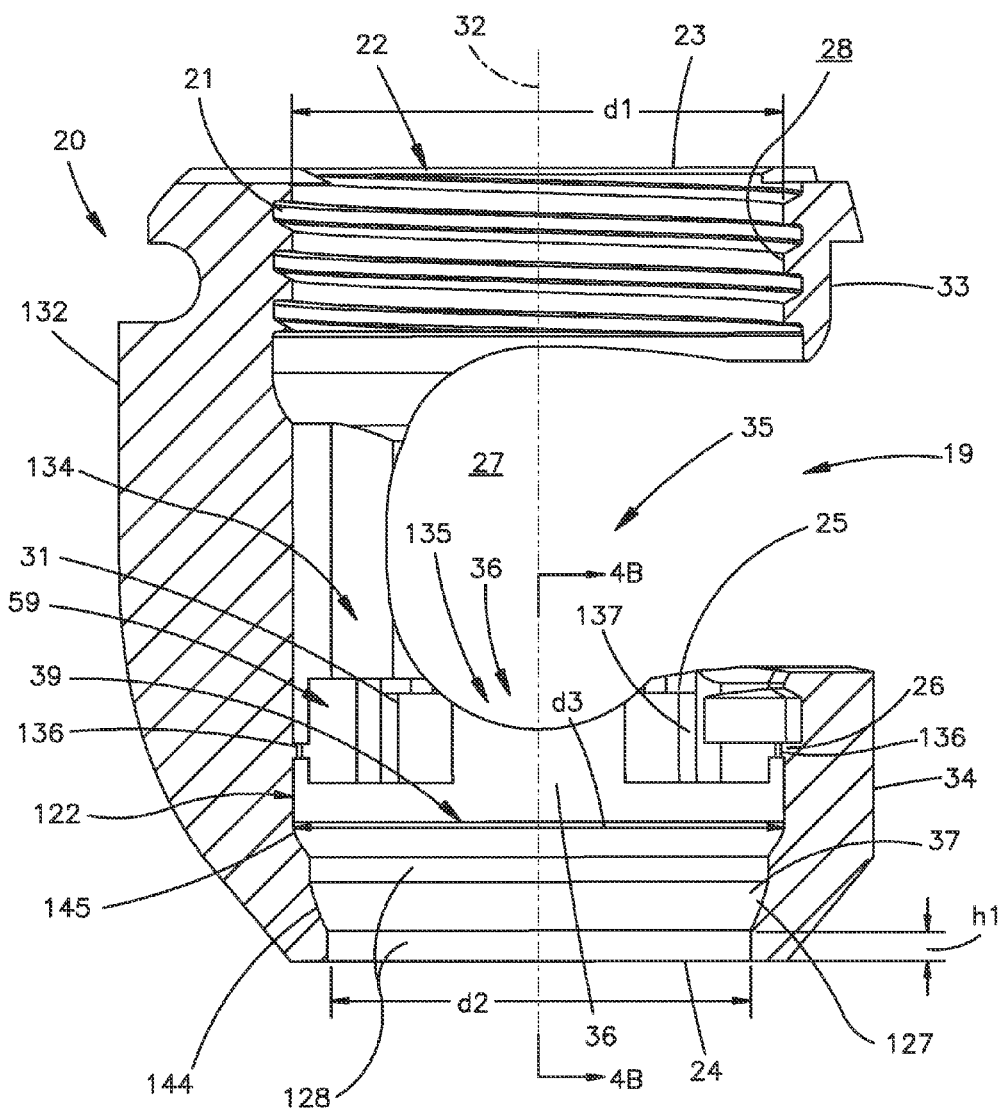
FIG. 4 illustrates a side cross-sectional view of the body element of FIG. 1.

Certain terminology is used in the following description for convenience only and is not limiting. The words "right", "left", "lower", "upper", "below", "above", "top", and "bottom" designate directions in the drawings to which reference is made. The words "inwardly" or "distally" and "outwardly" or "proximally" refer to directions toward and away from, respectively, the geometric center of the bone anchor system and/or assembly, the described instruments and designated parts thereof. The words, "anterior", "posterior", "superior", "inferior", "medial", and "lateral" and related words and/or phrases designate preferred positions and orientations in the human body to which reference is made and are not meant to be limiting. The terminology includes the above-listed words, derivatives thereof and words of similar import.

Certain exemplary embodiments of the invention will now be described with reference to the drawings. In general, such embodiments relate to a preferred bone anchor system including preferred bone anchor assemblies and related instruments by way of non-limiting example for use in spinal fixation which generally includes a rod-receiving channel configured and arranged to receive and secure the position of a spinal rod. Preferably the system may include (1) bone anchor assemblies that have a channel for receiving the spinal rod from the side, referred to as a side-loading bone anchor or side-loading bone anchor assembly, and/or (2) bone anchor assemblies that have a channel for receiving the spinal rod from the top, referred to as a top-loading bone anchor or top-loading bone anchor assembly. Preferably, the top-loading bone anchor assemblies can be used with side-loading bone anchor assemblies in the same system, and for the same spinal rod. The bone anchor assemblies may also include bodies having integral spinal rod elements or the bone anchor assemblies of the present invention may be used with bone anchor assemblies that have integral spinal rod elements.

Referring to FIGS. 1-3, bone anchor or bone fixation assembly 100 generally includes a bone anchor 10 (shown as a bone screw), a body 20, a bushing 40, and a locking cap 92, which includes a saddle 70. As will be described in greater detail below, the anchor assembly 100 preferably enables in-situ assembly of the bone anchor 10 to the body 20. That is, preferably, the bone anchor assembly 100 is configured so that in use, the bone anchor 10 may be secured to a patient's vertebra 200 prior to being received within the body 20. The bone anchor assembly 100 preferably enables a surgeon to implant the bone anchor 10 without the body 20 and bushing 40 pre-assembled to the bone anchor 10. By enabling the surgeon to implant only the bone anchor 10 without the body 20, the anchor assembly 100 maximizes visibility and access around the anchoring site.

Figure 5A:
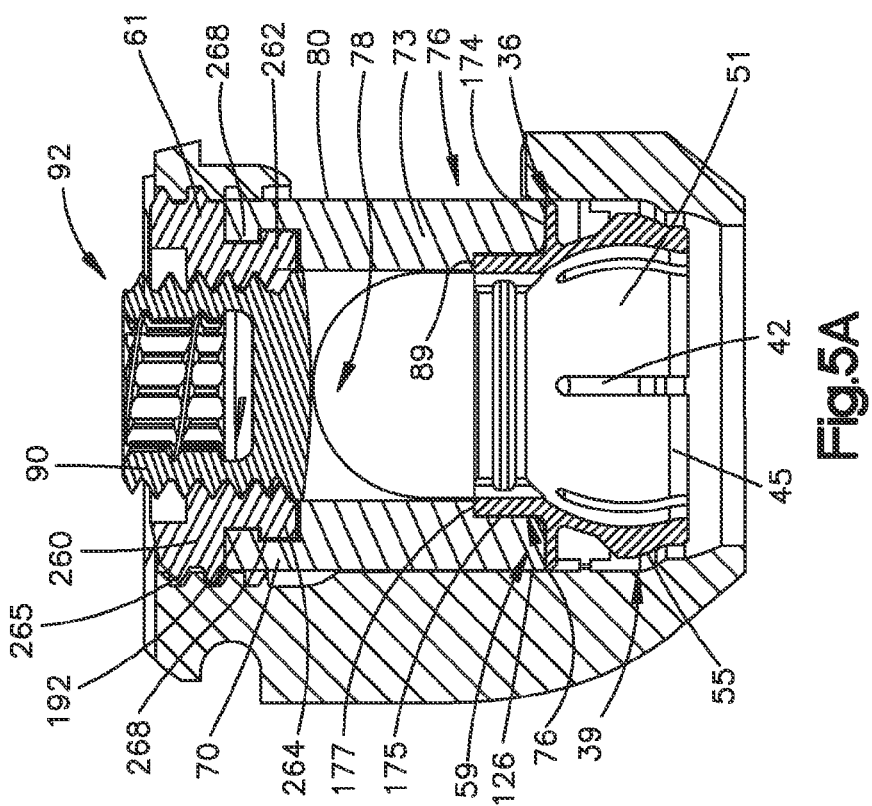
FIG. 5A illustrates a side cross-sectional view of the bushing element captured within the body element of FIG. 5 and a three-piece locking cap.

Once the bone anchor 10 has been secured to the patient's vertebra 200, the body 20 and bushing 40, which is retained in the body 20, may "click-on" to the bone anchor 10. Accordingly, in the preferred anchor assembly 100, the bone anchor 10 enters the body 20 through the lower opening 24 of the body 20. Once the body 20 and bushing 40 have been clicked onto the bone anchor 10, a spinal rod 101 may be inserted into a rod receiving channel 27, 29 formed in the body 20, and the locking cap 92 may be used to secure the position of the rod 101. Alternatively, the bone anchor assembly 100 (e.g., the body 20, bushing 40, and bone anchor 10) may be provided pre-assembled using components identical to or substantially similar to the components described herein. The body 20, and in particular the rod receiving channel 27 may be configured for side-loading as shown in FIGS. 1-1A, or the rod receiving channel 29 may be configured for top-loading as shown in FIG. 2-2A. Additionally, the bushing and body sub-assembly may be popped-off of the bone anchor 10 in-situ by arranging and positioning the bushing 40 in a loading/unloading position relative to the body 20, as shown in FIGS. 5A and 8, and removing the bushing/body sub-assembly from the bone anchor 10, as will be described in greater detail below.

While the anchor assembly 100 will be described as and may generally be used in the spine (for example, in the lumbar, thoracic or cervical regions), and in particular attached to the vertebra 200 as shown in FIG. 3, those skilled in the art will appreciate that the anchor assembly 100 may be used for fixation of other parts of the body such as, for example, joints, long bones, ribs, or bones in the hand, face, feet, toe, extremities, cranium, mandible, etc., and may be used for non-orthopedic applications and non-medical applications.

As shown in FIG. 3, bone-anchoring system 5 may include several anchor assemblies 100 and may be used with one or more spinal rods 101 to secure and interconnect several vertebrae 200. It should be understood that the spinal rod 101 may constitute or include, but is not limited to, a solid rod, a non-solid or hollow rod, a flexible or dynamic rod, etc. It should be understood that bone anchor system 5 is not limited in use to any particular type of spinal rod 101 and any elongated element or support member of any shape and configuration is contemplated.

Referring to FIGS. 1-3, the bone anchor 10 preferably is in the form of a bone screw. Alternatively, however, the bone anchor 10 may be, for example, a hook, pin, blade, nail, tack, stake or other fastener such as, a clamp, an implant, etc.

The bone anchor 10 preferably includes an enlarged, curvate head 14 and an externally threaded shaft portion 15 for engaging the patient's vertebra 200. The specific features of the shaft 15 including, for example, thread pitch, shaft diameter, shaft shape, etc. may be varied, and it would be apparent to one having ordinary skill in the art that the bone screw 10 is not limited to any particular features on or type of shaft 15. The bone screw 10 may or may not be cannulated. The bone screw 10 may also include a reduced diameter neck portion 16 between the head 14 and the shaft portion 15, which facilitates the polyaxial nature of the bone fixation assembly 100. The bone screw 10 may further be cannulated and fenestrated (not shown) such that openings extend outwardly from a central hollow channel 12 in the cannulated screw for a multitude of potential uses, including, but not limited to, urging material out of the screw during injection, drawing fluid into the central hollow channel from the sides of the screw to extract material adjacent the screw, or passing through instruments or implants.

Referring to FIGS. 1A and 2A, the enlarged head 14 preferably has a curvate or semi-spherical shape to facilitate rotation and angulation with respect to the bushing 40 before the bone screw 10 is locked to the body 20, as will be described in greater detail below. The head 14 also preferably includes a drive surface 17 for receiving a corresponding tip formed on a drive tool, such as a screwdriver for rotating the bone screw 10 into engagement with the patient's vertebra 200. The drive surface 17 may have any form now or hereafter known including, but not limited to, an external hexagon, a star drive pattern, a Phillips head pattern, a slot for a screw driver, a threading for a correspondingly threaded post, etc. Preferably, as shown, the drive surface 17 is comprised of a first tool interface 13, but is not so limited and may be comprised of an external drive feature that engages a female-type driver (not shown). The specific shape of the drive surface 17 or first tool interface 13 may be chosen to cooperate with the corresponding drive tool.

As disclosed in International App. No. PCT/US2008/070670, entitled "Polyaxial Bone Fixation Element," filed Jul. 21, 2008, the entire contents of which are incorporated by reference herein, the head 14 may also include a second tool interface or a sleeve interface 18. The second tool interface 18 may include threading (as shown) or other features to interact with instruments, such as a drive instrument.

Referring to FIGS. 1A, 2A and 4-4F, the body 20 may generally be described as a cylindrical tubular body having a rod receiving channel 27, 29, a longitudinal axis 32, an upper end 33 having an upper opening 23, a lower end 34 having a lower opening 24, and an axial bore 22 preferably substantially coaxial with the longitudinal axis 32 of the body 20. The axial bore 22 extends from the upper opening 23 to the lower opening 24 and has a lower chamber 36 proximate the lower end 34. The axial bore 22 at the upper opening 23 has a first diameter d1 and the bore 22 at the lower opening 24 has a second diameter d2, which is preferably smaller than the first diameter d1. The second diameter d2 is preferably sized and configured so that the enlarged head 14 of the bone anchor 10 may be passed through the lower opening 24 of the body 20. The body 20 also includes an outer surface 132 and an inner surface 28. The inner surface 28 of the axial bore 22 preferably includes a plurality of threads 21 in the upper end 33 for engaging the locking cap 92, 190. Alternatively, the body 20 and, in particular, axial bore 22 may have nearly any mounting structure for engaging the locking cap 92, 190 including, but not limited to, external threads, cam-lock, quarter lock, clamps, lugs, bayonets, etc.

In the side-loading bone anchor, a rod-receiving channel 27 is formed in the side of body 20 to receive the spinal rod 101. In the top-loading bone anchor, a rod-receiving channel 29 is formed in the top of the body 20 to receive the spinal rod 101. The rod-receiving channel 27, 29 is generally transverse, preferably perpendicular, to the longitudinal axis 32 of the body 20 and communicates with and connects to the axial bore 22. The rod receiving channel 27, 29 may be sized and constructed to receive a spinal rod 101 of any size or configuration now known or later discovered.

Referring to FIGS. 4-4F, the lower chamber 36 may include an upper portion 122 having a maximum third diameter d3 and a lower portion 127 having the lower opening 24. The lower opening 24 is configured such that second diameter d2 is preferably smaller than the third diameter d3 of the upper portion 122 of the lower chamber 36. The diameter d3 of the upper portion 122 of the lower chamber 36 is preferably larger than the diameter d1 of the axial bore 22. In this manner, the bushing 40 preferably may be inserted through the upper end 33 into the axial bore 22, but is prevented from falling out of the lower opening 24 at the lower end 34 of the body 20. The lower chamber 36 is additionally preferably sized and configured such that the diameter in the lower chamber 36 may be variable depending upon the region or zone between the third diameter d3 and the second diameter d2.

The lower chamber 36 may also preferably include one or more lower chamber surfaces 37 in the lower end 34 of the body portion 20, an interference zone 59, and a rotation zone 39. The lower chamber surfaces 37 of the body preferably include a first curvate or spherical concave surface 144 for accommodating bushing 40 having an outer surface 50. The first spherical surface 144 has a radius of curvature r1 that is preferably centered on the longitudinal axis 32 of the body 20. Preferably, a second spherical surface 145 may be provided. The second spherical surface 145 is positionable adjacent and above the first spherical surface 144 and preferably has a radius of curvature r2 centered on the longitudinal axis 32 of the body 20. The radius of curvature r2 is preferably different than, and preferably larger than, the radius of curvature r1. The diameter of the lower chamber 26 in the region of the second concave surface 145 is preferably larger than the diameter of the lower chamber 36 in the region of the first concave surface 144. The interference zone 59 and rotation zone 39 are preferably located in the upper portion 122 of the lower chamber 36 and will be further discussed below.

Figure 5:
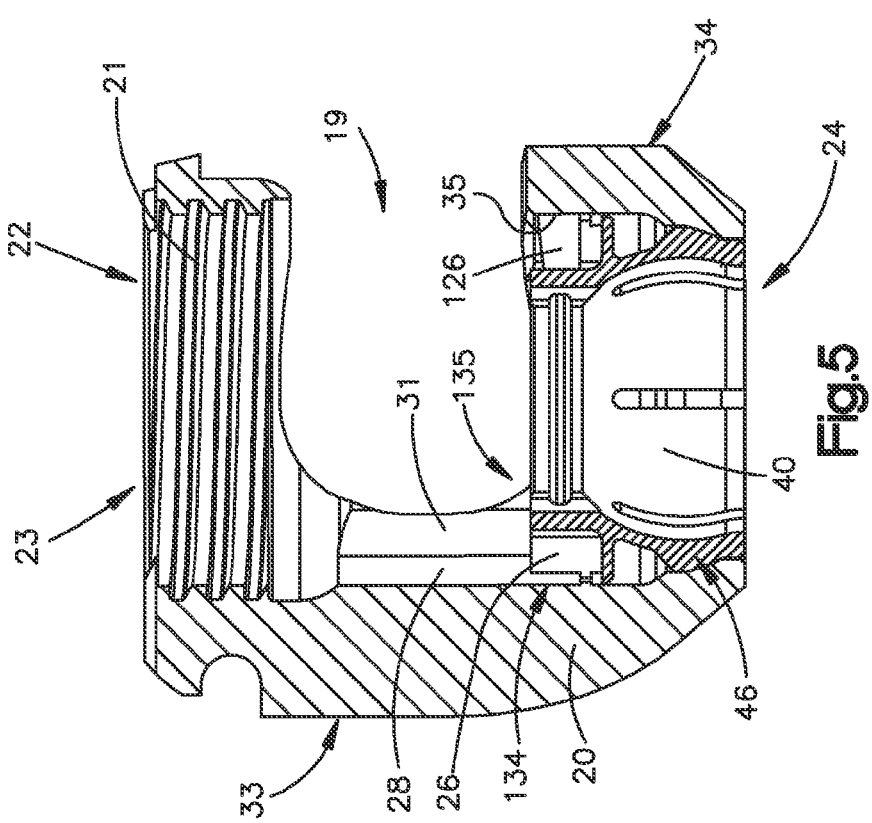
FIG. 5 illustrates a cross-sectional perspective view of a an alternative preferred embodiment of the bushing element captured within a modified body element of FIG. 1A.

Referring to FIGS. 5-5A, the bushing 40 is preferably placed into the lower chamber 36 of the body 20 during manufacture and is permitted to move within a portion of the axial bore 22 formed in the body 20 between a loading/unloading position (FIG. 5A) and a locked position (FIG. 5). That is, the bushing 40 is preferably movably positionable within the body 20 between a position where the bone anchor 10 can be connected to or unconnected from the bushing 40 (loading/unloading/unlocked position), and a position where the bushing 40 is locked with respect to the bone anchor 10 (locked position). However, the bushing 40 is preferably constructed such that it may be inserted into the body 20 through the upper opening 23, but is prevented from exiting through the lower opening 24. Once the bushing 40 is placed and assembled into the body 20, the bushing 40 is preferably retainable within the body 20 such that the bushing 40 is generally prevented from either (1) passing back up through the upper opening 23 formed in the body 20; (2) passing through the lower opening 24 formed in the body 20; or (3) passing through the rod receiving channels 27, 29.

Referring to FIGS. 6-6B and 7-7A, the bushing 40 preferably includes an upper end 47 having an upper opening 54, a lower end portion 46 having a lower opening 142, and a bore 48 that extends from the upper opening 54 to the lower opening 142. A drive tool, such as, for example, a screw driver, can be inserted through the bore 48 of the bushing 40 and into engagement with the bone anchor 10 so that the bone anchor 10 may be rotated into engagement with the patient's vertebra 200. The bushing 40 also includes an exterior surface 55, which may be sized and configured to contact the lower chamber surfaces 37 when the head 14 of the bone anchor 10 is secured within the bushing 40 in a locked position, as will be detailed further below.

The lower end portion 46 of the bushing 40 preferably includes an interior cavity 51 for receiving and securing the head 14 of the bone anchor 10 so that the bone anchor 10 can rotate polyaxially through a range of angles with respect to the bushing 40 and hence with respect to the body 20 when in an unlocked or loading/unloading position. The interior cavity 51 formed in the bushing 40 preferably has a curvate or semi-spherical shape for receiving the curvate or semi-spherical head 14 of the bone anchor 10. The interior cavity 51 formed in the bushing 40 is preferably constructed so that the bone anchor 10 can polyaxially rotate with respect to the bushing 40, when the bushing is in an unlocked position, and hence, with respect to the body 20.

The bushing 40 preferably also includes one or more slots 42 (shown as a plurality of slots, e.g., FIGS. 6-7A) extending from the lower end portion 46 thereof so that at least a portion of the bushing 40 is: (i) radially expandable so that the head 14 of the bone anchor 10 can be inserted through the lower opening 142 in the lower end portion 46 and into the interior cavity 51 of the bushing 40 and (ii) radially compressible to compress or lock against the head 14 of the bone anchor 10 when radial forces are applied thereto. In the preferred embodiment, the slots 42 define a plurality of flexible arms 45. Preferably each flexible arm 45 includes a root end 52 and a terminal end 53. The slots 42 may extend from the lower end 46, the upper end 47 or both ends 46, 47. One slot 42 may extend the length of the bushing 40 creating a compressible spring clip.

Referring to FIGS. 7-7A and 8, in one preferred embodiment, the exterior surface 55 of the flexible arms 45 may form at least a portion of the outer surface 55 of the bushing 40 and is comprised of a curvate or spherical, convex surface 50 having an outer radius of curvature r5 for contacting the lower chamber surfaces 37 of the body 20. The radius of curvature r5 of the bushing 40 is preferably different than the radius of curvature r1 of the first spherical surface 144 of the lower chamber surfaces 37 such that a generally line contact is defined between the first spherical surface 144 and the exterior surface 55 of the bushing 40 when the bushing 40 is positioned proximate the lower end 34 of the body 20 in the locked position. The frusto-spherical convex surface 50 of the bushing 40 preferably facilitates proper alignment of the bushing 40 within the bore 22 of the body 20 to receive the head 14 of the bone anchor 10 without impediment.

Figure 4B:
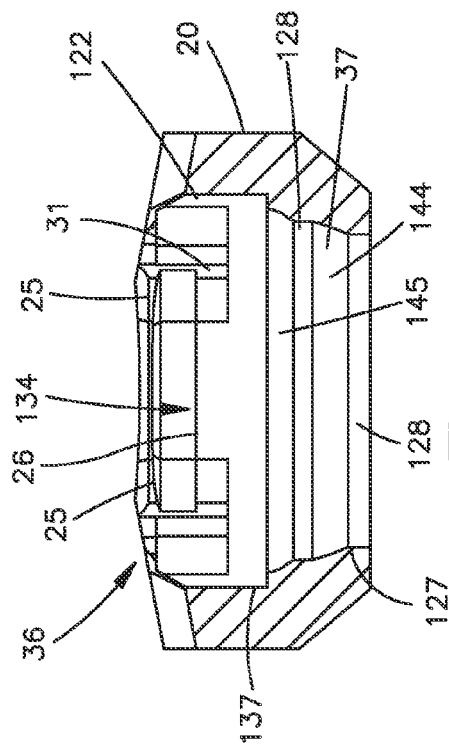
FIG. 4B illustrates a side cross-sectional view of the lower portion of the body element of FIG. 4 along line 4B-4B.

Referring to FIGS. 5, 5A and 6-6A, in an alternative preferred embodiment, the outer surface 55 of the bushing 40 preferably includes the spherical, convex surface 50 and one or more cylindrical zones 43, 44. Referring to FIGS. 4 and 4B, the lower chamber surfaces 37 of the body 20 may also include one or more cylindrical surfaces 128. The one or more cylindrical surfaces 128 are preferably configured and arranged to accommodate the one or more cylindrical zones 43, 44 of the bushing 40. The one or more cylindrical surfaces 128 may be any height h1, but in the embodiment shown, are preferably approximately 1 mm in height and generally are preferably about 0.5 mm to about 2 mm. The cylindrical zones 43, 44 preferably have a height h2 of about 1 mm, and generally may have a height of about 0.5 mm to about 2 mm although other values are contemplated.

Referring to FIGS. 6-7A, the cylindrical zones 43, 44 are provided to prevent the bushing 40 from angulating within the body 20 about an axis that is perpendicular to the axis 32, which may be caused by a surgeon manipulating the body 20 during surgery. That is, the cylindrical zones 43, 44 on the bushing 40 in combination with the cylindrical zone 128 in the body 20 preferably resist the bushing from angulating or toggling in the body so that the longitudinal axis 49 of the bushing preferably remains parallel and co-linear with the axis 32 of the body 20. Such rotation could cause the body 20 to move toward the upper end 33 of the body 20 in the axial bore 22, which may permit the body 20 to click-off the head 14 of the bone anchor 10. The cylindrical zones 43, 44 may also offer further benefits. For example, when axial force is applied downward on the upper end 47 of the bushing 40, the cylindrical zones 43, 44 may inhibit the bushing 40 from protruding from the lower opening 24 of the body 20. In this manner, the cooperating cylindrical surfaces 128 and cylindrical zones 43, 44 may prevent the bushing 40 from jamming and the bushing 40 from becoming deformed and unusable. The cylindrical zones 43, 44 of the bushing 40 may also inhibit and resist the bushing 40 from unlocking or releasing the head 14 of the bone anchor 10 after the body 20 and bushing 40 have been clicked onto the head 14 of the bone anchor 10. That is, the bushing 40 can translate upward in the body 20 without releasing the locking force exerted by the body 20 on the bushing 40 since the bushing arms 45 remain in position and are prevented from expanding while the cylindrical surfaces 128 remain in the cylindrical zones 43, 44.

As discussed, the bushing 40 is preferably placed and retained within the body 20 during the manufacturing process. To place and retain the bushing 40 in the body 20, the bushing 40 preferably may be provided with structures, features, geometry and a configuration that interacts and interfaces with structures, features and geometry of the body 20. In one preferred exemplary embodiment, the bushing 40, as shown in FIG. 6B, may be provided with one or more first wings 41 and one or more second wings 56.

More specifically, as shown in FIG. 6B, the bushing 40 is preferably provided with a pair of first wings 41 extending from the exterior surface 55 of the bushing 40 and having a first wing width or arc length w1. The first wings 41 preferably extend generally perpendicular to the bushing axis 49 and are preferably spaced one hundred eighty degrees (180°) from one another. The bushing 40 preferably is also provided with a pair of second wings 56 having a second wing width or arc length w2, wherein w2 preferably is greater than the first wing width w1. That is, the second wings 56 are generally wider than the first wings 41. The second wings 56 are also disposed on the exterior surface 55 of the bushing 40 and preferably extend generally perpendicular to the bushing bore 48. Each second wing 56 is positioned between and adjacent a first wing 41 and are preferably spaced one hundred eighty degrees (180°) from one another. The first, narrower wings 41 preferably have a wing diameter wd1 that is greater than the second wing diameter wd2 of the second, wider wings 56.

That is, the lip extension 57 of the first wings 41 extends further than the lip extension 58 of the second wings 56. While the bushing 40 has been described and illustrated as having a first pair of wings 41 and a second pair of wings 56, it should be recognized that one or more wings 41 (or no wings 41) and one or more wings 56 (or no wings 56) may be provided in different sizes, shapes, positions and configurations and that the bushing is not limited to the structure and configuration shown and described.

Figure 19A:
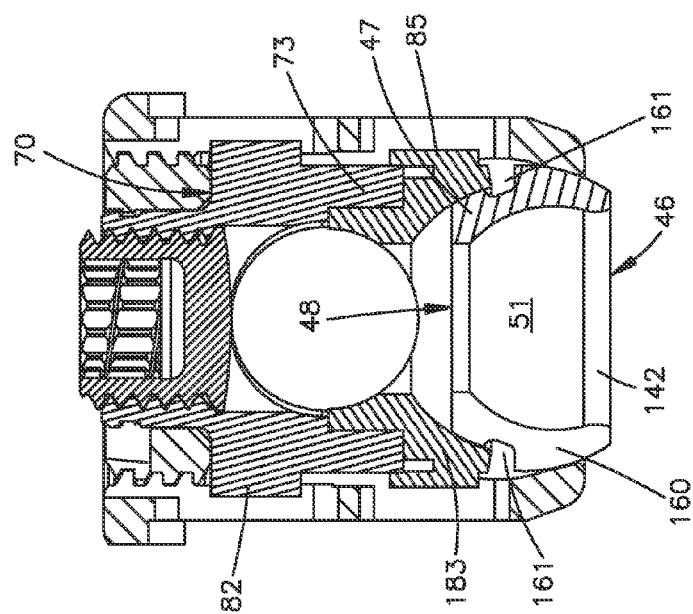
FIG. 19A illustrates a side cross-sectional view of the bone anchor assembly of FIG. 19.
Figure 20:
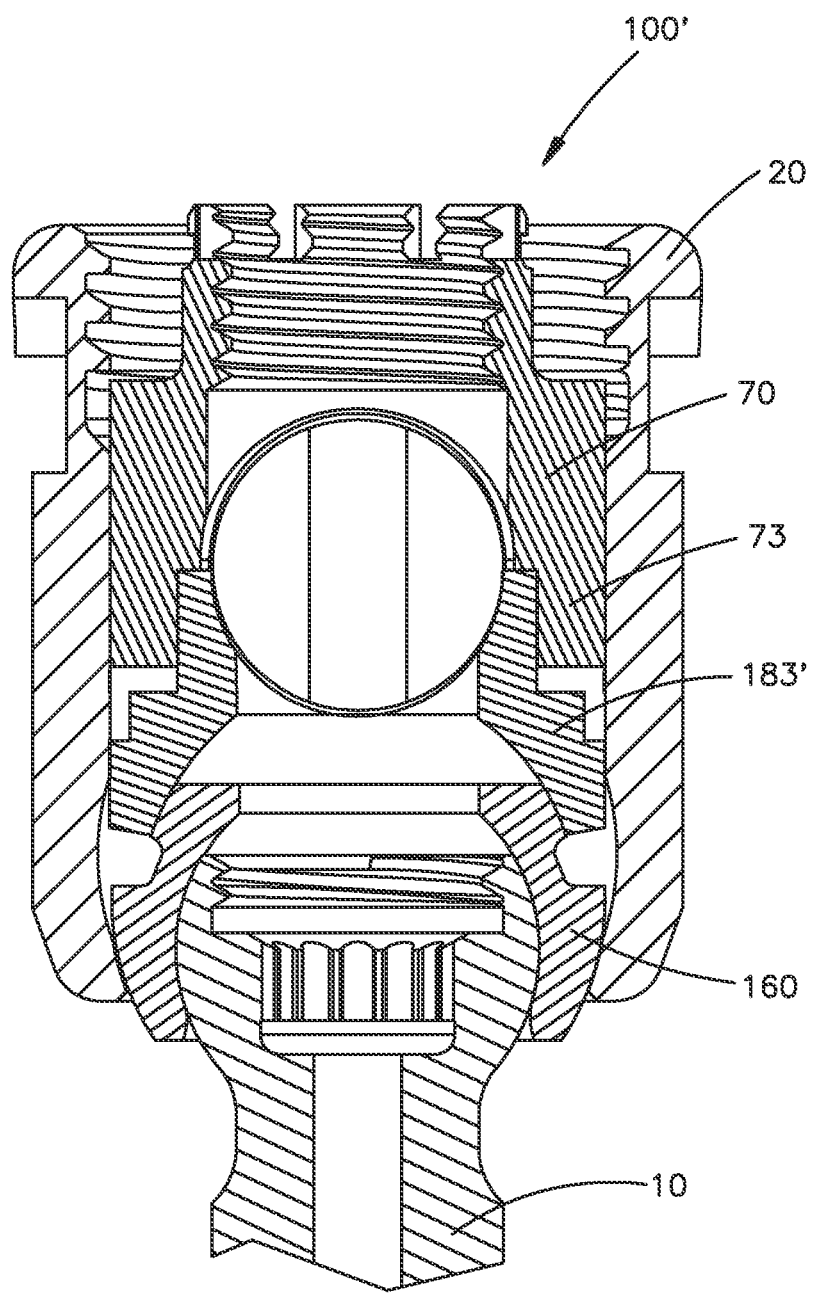
FIG. 20 illustrates a side cross-sectional view of a sixth preferred embodiment of the bone anchor assembly of the present invention.
Figure 23:
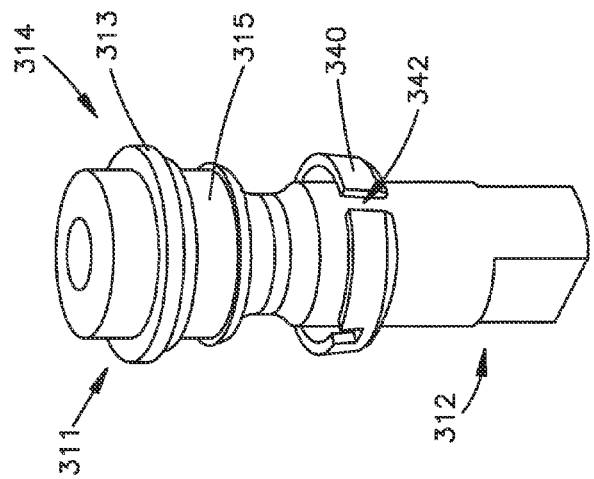
FIG. 23 illustrates a perspective view of a fastener element and bone screw in accordance with the embodiment of the bone anchor assembly of FIG. 22.
Figure 22:
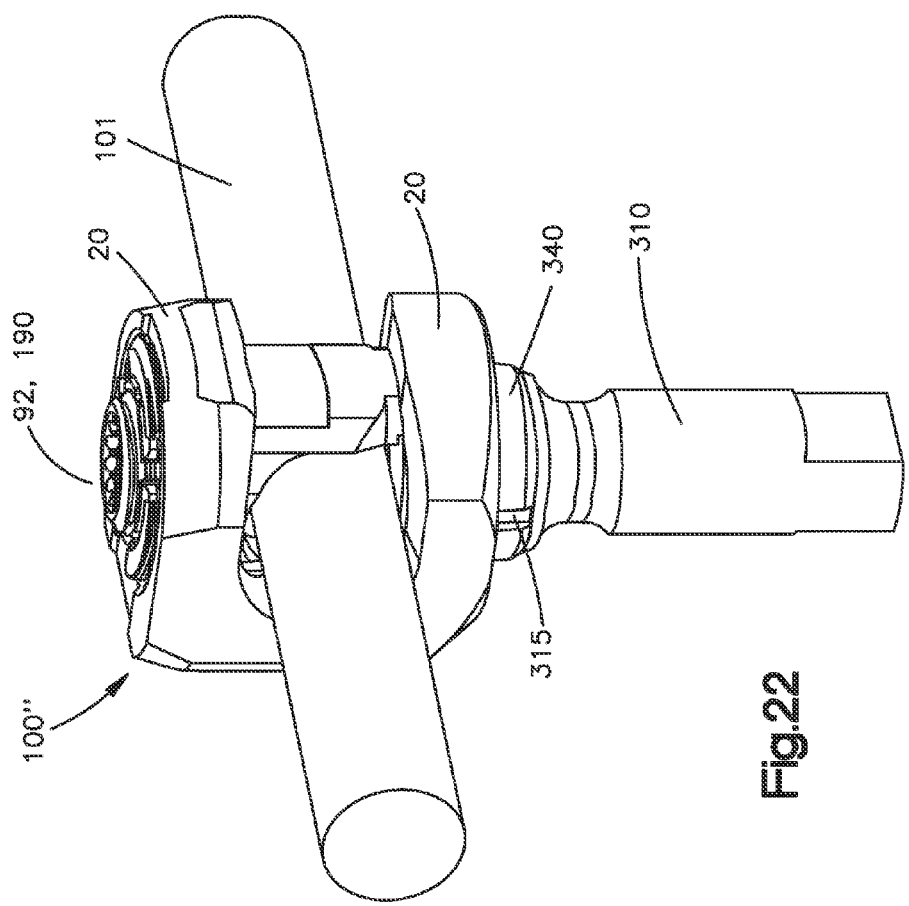
FIG. 22 illustrates a side perspective view of an eighth embodiment of a bone anchor assembly in accordance with the present invention.

While bushing 40 has been illustrated and described in FIGS. 1-7A as being generally one-piece, the bushing may comprise a multi-piece element as described and illustrated in FIGS. 19D and 20, and the bushing 40 is not limited to the structure, features or configuration shown.

With reference to FIG. 4, the body 20 additionally preferably includes a geometry and configuration that interacts and interfaces with the bushing 40 to retain the bushing 40 in the lower chamber 36 of the body 20. The lower chamber 36, and preferably the upper portion 122 of the lower chamber 36, preferably includes an interference zone 59 and a rotation zone 39. The rotation zone 39 is preferably disposed above the first spherical surface 144 and may be located above the second spherical surface 145 or may include the entire second spherical surface 145 or portions thereof. The interference zone 59 preferably is located above the rotation zone 39 and includes major projections 31 and first stops 25 forming channels 134, 135. The interference zone 59 may also optionally include one or more second stops 26.

The major projections 31 preferably extend in the direction of the longitudinal axis 32 of the body 20 and are disposed on the lower chamber surface 37 in the interference zone 59. As will be described in more detail below, the major projections 31 prevent rotation of the bushing 40 when the bushing is located in the interference zone 59. First stops 25 are disposed on the inner surface 37 at the top portion of the interference zone 59 above the major projections 31. The first stops 25 together with the major projection 31 generally resemble a "T-shape" when viewed from the side. The first stops 25, as will be described below, retain the bushing 40 in the body 20 and provides support to the bushing 40 when the bone anchor 10 is being clicked into the body 20.

Figure 4A:
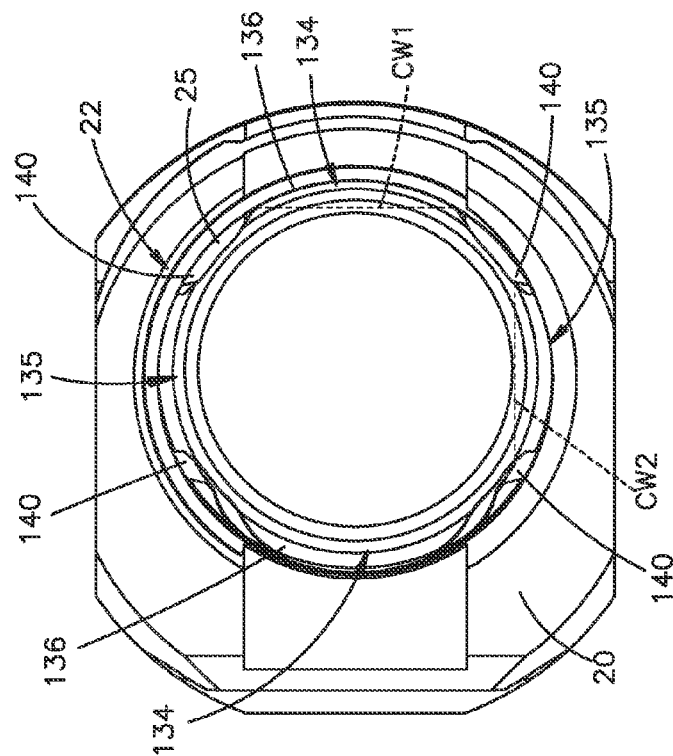
FIG. 4A illustrates a top view of the body element of FIG. 4.

The preferred embodiment, as shown in FIGS. 4A and 4B, has four (4) major projections 31 and four (4) first stops 25 located above the major projections 31. The first stops 25 and the major projections 31 form four (4) channels 134, 135 in the interference zone 59 for receiving the wings 41, 56 of the bushing 40. More specifically, in the embodiment of FIGS. 4, 4A and 4B, the first stops 25 and major projections 31 form a pair of first channels 134 spaced approximately one hundred eighty degrees (180°) apart having a first channel width or arc length $CW_1$. The first stops 25 and major projections 31 form a pair of second channels 135 spaced approximately one hundred eighty degrees (180°) apart having a second channel width or arc length $CW_2$ such that the width CW1 of the first channels 134 are wider than the width $CW_2$ of the second channels 135. The difference in the width $CW_1$ of the first channels 134 as compared to the width $CW_2$ of the second channels 135 preferably is the result of the ends 140 of the first stops 25 extending circumferentially more into the second channels 135 than the first channels 134.

Optionally, one or more second stops 26, as shown in FIG. 4, may be provided in the interference zone 59 below the first stops 25. The second stops 26 preferably constitute projections 136 that extend into the lower chamber 36 in the interference zone 59. In the embodiment of FIGS. 4-4B, projections 136 forming the second stops 26 extend inward from the inner surface 28 in first channels 134 but preferably do not extend inward as much as the first stops 25. The second stops 26 preferably resist the head 14 of the bone anchor 10 from being dislodged from the bushing 40 during adjustment of the bone fixation system and/or assembly as will be described in more detail later.

The bushing 40 is preferably preassembled and retained within the body 20. To assemble the bushing 40 into the body 20, the first wings 41 and the second wings 56 are sized and configured so that the bushing 40 may be inserted through the upper opening 23 of the body 20 and down the axial bore 22. The bushing 40 is further sized and configured such that the first wings 41 may be inserted down second channels 135 in the interference zone 59 while the second wings 56 may be inserted down the first channels 134 in the interference zone 59. Preferably the first wings 41 and second wings 56 of the bushing 40 are pushed down channels 135 and 134 respectively, and past the first stops 25 without interference. In addition, as the bushing 40 is pushed down the axial bore 22, the second wings 56 which have a smaller diameter (wd2) than the first wings 41 (wd1) are moved down the first channels 134 past the optional second stops 26 without interference. The first wings 41 and second wings 56 are alongside the major projections 31 as the bushing 40 is moved down the interference zone 59 to the rotation zone 39. As the bushing 40 is pushed down the interference zone 39, the wings 41, 56 and major projections 31 preferably prevent the bushing 40 from rotating or turning about its axis 49 and the axis 32 of the body 20. Preferably, in order to push the bushing 40 down far enough so that the wings 41, 56 are positioned in the rotation zone 39, the lower end 46 of the bushing 40 is pressed into the lower chamber surfaces 37 of the lower portion 127 of the lower chamber 36 so that the arms 45 of the bushing 40 are compressed inward. Preferably, if the bone anchor 10 is captured in the bushing 40, the bushing 40 cannot be pushed down far enough in the lower chamber 36 to permit the wings 41, 56 to be located within the rotation zone 39.

When the wings 41, 56 are positioned in the rotation zone 39, the bushing 40 may be rotated about axis 32/axis 49 such that first wings 41 are positioned below and aligned with the first channels 134 and the second wings 56 are positioned below and aligned with the second channels 135. In the embodiment of FIGS. 5, 5A and 9, with the wings 41, 56 positioned in the rotation zone 39, the bushing preferably is rotated ninety degrees (90), or two hundred seventy degrees (270) to align the first narrower wings 41 with the first wider channels 134 and the second wider wings 56 with the second narrower channels 135, although in other embodiments the bushing 40 may be rotated different amounts in order to align the wings with the proper channels. With the first wings 41 aligned with the first channels 134, and the second wings 56 aligned with the second channels 135, the bushing 40 may be pushed up so that the wings 41, 56 are positioned in the interference zone 59. With the wings 41, 56 located in the interference zone 59, the arms 45 of the bushing 40 are predominantly located in the rotation zone 39 to permit assembly of the head 14 of the bone anchor 10 into the bushing 40 that is contained within the body 20.

The bushing 40 may be retained in the loading position with the arms 45 of the bushing 40 aligned with and located within the rotation zone 39 by (1) the first stops 25 preventing the bushing from passing through the axial bore 22 and out of the upper opening 23 of the body 20, and (2) the interaction of the arms 45 of the bushing 40 with the lower chamber surfaces 37 of the lower chamber 36 preventing the wings 41, 56 from dropping into the rotation zone 39. Specifically, the bushing 40 may be retained in the loading position because the stops 25 interfere with continued movement of the bushing 40 up the axial bore 22 and out of the upper opening 23 of the body 20. The second wings 56 interact with and abut against the first stops 25 and prevent the bushing from being pushed up the axial bore 22 and out the upper opening 23 of the body 20. More specifically, the edges 139 of the wider second wings 56 interfere with the ends 140 of the first stops 25 preventing further upward motion of the bushing 40 (FIG. 9). The first narrower wings 41 in the wider first channel 135 do not interfere or interact with the first stops 25. The major projections 31 prevent the bushing 40 from rotating while in the interference zone 59. The lower end 53 of the arms 45 of the bushing 40 retain the bushing 40 in the loading position because they abut against the lower chamber surfaces 37 of the lower chamber 36 before the bushing 40 drops far enough down in the interference zone 59 for the wings 41, 56 to be located in the rotation zone 36.

If the optional second stops 26, as shown in FIG. 4, are provided in the first channels 134, the first wings 41 are pushed up past the second stops 26 by elastically deflecting the wings 41 and/or second stops 26 as the bushing 40 is pushed up into the interference zone 59. The optional second stops 26 will interact with the first wings 41 to also prevent the bushing 40 from sliding down into the rotation zone 39 of the lower chamber 36 so that the bushing 40 will be further retained in the body 20. The bushing 40 is thus assembled to preferably position the bushing 40 within the body 20 so that the first and second wings 41, 56 are located in the interference zone 59 between the first stops 25 and the second stops 26 (see FIG. 8). In this manner the bushing 40 may be prevented from detaching from the body 20 because the second stops 26 and the compressing of the bushing 40 inhibit the wings 41, 56 of the bushing 40 from moving back into the rotation zone 39 and rotating to such degree that it might be able to be pushed upwards in the bore 22 and detach from the body 20.

Referring to FIG. 8, to interconnect or attach the bone anchor 10 to the body 20, the body 20 is preferably provided with the bushing 40 pre-assembled and in the loading position with the wings 41, 56 located in the interference zone 59 between the first stop 25 and the second stop 26 so that the bushing arms 45 are predominately located in the rotation zone 39. The head 14 of the bone anchor 10 is inserted into the lower opening 24 of the body 20 and into the interior cavity 51 of the bushing 40. After the head 14 of the bone anchor 10 is inserted into the cavity 51 of the bushing 40 and snapped into the bushing 40, the bushing and bone anchor subassembly is preferably moved down into the lower chamber 36 of the body 20 to prevent the head 14 of the bone anchor 10 from becoming dislodged from bushing 40.

Optional second stops 26 may assist in inhibiting the bone anchor and bushing sub-assembly from moving up into the chamber 36 where the bushing 40 can detach from the bone anchor 10. After the bone anchor 10 is clicked onto the body 20 and captured within the bushing 40, the bushing and bone anchor sub-assembly is preferably pushed down in the lower chamber 36 so that the first wings 41 move pass the second stops 26. An instrument may assist with moving the bushing and bone anchor sub-assembly past the second stops 26 by deflecting one or both of the first wings 41 and second stops 26, and/or providing sufficient force to push the bushing 40 down past the second stop 26. The wings 41, 56 preferably would still be located in the interference zone 59 so that the bushing 40 is prevented from rotating about axis 49/axis 32 in the body 20. The second stops 26 preferably would thereafter prevent the bushing 40 from moving up so that the bushing arms 45 would be positioned into the rotation zone 39 where the bushing arms 45 can expand and release the bone anchor 10. That is, the forces the bone anchor assembly 100 is likely to encounter during the surgery from manipulation and adjustment by the surgeon is unlikely to force the first wings 41 up past the second stops 26. In this manner, the bushing and bone anchor sub-assembly can be positioned so that the first wings 41 are below the second stops 26 so that the arms 45 are not expandable and cannot release the bone anchor 10, but the bone anchor 10 may still be movable and adjustable with respect to the body 20 and the spinal rod 101.

Referring to FIGS. 1A, 2A and 8, once the head 14 of the bone anchor 10 is received into the bushing 40, the bushing 40 may be moved downward toward the lower opening 24 of the body 20 to lock the head 14 of the bone anchor 10. As the bushing 40 moves downwards, the arms 45 of the bushing 40 come into contact with the one or more lower chamber surfaces 37 in the lower chamber 36 of the body 20, which exert a force against the arms 45 of the bushing 40, causing the arms 45 to collapse around the head 14 of the bone anchor 10 into a locking position, thereby locking the position of the bone anchor 10 relative to the body 20. More particularly, as the bushing 40 moves downward, the bushing arms 45 preferably contact the first spherical surface 144 which pushes and preferably elastically deflects the bushing arms 45 radially inward so that the arms collapse about the head 14 of the bone anchor 10. Preferably, a line contact or a contact band of limited width is formed between the bushing 40 and the first spherical surface 144. The locking caps 92, 190 as described below preferably control the locking action of the bushing 40.

Referring to FIGS. 1A, 5A, 10 and 21, the locking cap may preferably be either a three-piece locking cap 92 (FIGS. 1A, 5A and 8) or a two-piece locking cap 190 (FIG. 21). The locking cap 92, 190 is movable from an unlocked to a locked position to lock the bone anchor 10 and the rod 101 in place. The three-piece locking cap 92 preferably permits separate locking of the adjustability of the bone anchor 10 and the rod 101, whereas the two-piece locking cap 190 permits locking of the adjustability of the bone anchor 10 and the rod 101 in one step.

The locking cap 92, 190 includes a saddle 70 and a means for engaging the body 20. The means for engaging the body 20 may include, but is not limited to, an externally threaded cap, an internally threaded cap, a quarter-turn or partial-turn locking cap, cam-lock, bayonet and lug, two-piece set screw, etc. The saddle 70 of the locking cap 92, 190 in the preferred embodiments includes a bore 170 and two saddle arms 73 defining an inverse U-shaped channel 78. The saddle 70 preferably is inserted into and extends down the axial bore 22 of the body 20. With the saddle inserted into the axial bore 22, the U-shaped channel 78 is sized and configured to fit at least partially over the spinal rod 101. The saddle arms 73 are preferably of sufficient length to extend into and be received by the lower end 34 of the body 20, as will be later discussed, to secure the position of the spinal rod 101. In an alternative embodiment, the saddle 70 may have shorter saddle arms 73 that extend partially over and around the spinal rod 101 (FIGS. 19A and 20).

Figure 12:
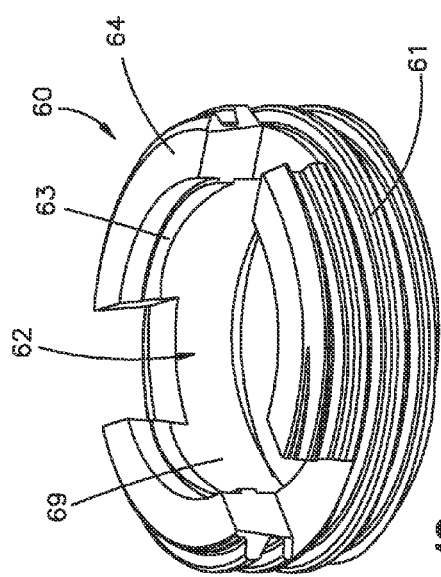
FIG. 12 illustrates a perspective view of a threaded ring element in accordance with the present invention.

Referring to FIGS. 1A, 2A, 5A, 8 and 10, a three-piece locking cap 92 is provided, having the saddle 70, a setscrew element, such as a setscrew 90, and a threaded ring 60. The three-piece locking cap 92 may assume various configurations. In one configuration, as shown in FIGS. 1A, 2A, 8 and 10, the setscrew 90 is received within the saddle 70 while in another configuration, shown in FIG. 5A, the setscrew 70 is received in the threaded ring 60. In both of these configurations the saddle 70 is interconnected to and its operation (movement) is controlled by the threaded ring 60. The saddle 70 may be interconnected to the threaded ring 60 in many different ways and the threaded ring 60 is preferably independently rotatable with respect to the saddle 70. In the three-piece locking cap embodiment of FIGS. 1A, 2A, and 8 where the setscrew 90 is received in the saddle, the threaded ring 60 as shown in FIG. 12 includes a bore 62, one or more ledges 63, and exterior threads 61. The one or more ledges 63 of the threaded ring 60 are formed on the inner surface 69 of the threaded ring 60. The threaded ring 60 in this embodiment does not include interior threads in the bore 62. The exterior threads 61 of the threaded ring 60 are threadably engagable with the interior threads 21 of the body 20. The saddle 70 is provided with a ledge 87 disposed proximate the upper end 88 of the saddle 70 that extends outward and is preferably capable of interlocking with the ledge 63 of the threaded ring 60 to interconnect the threaded ring 60 to the saddle 70. The saddle 70 additionally has internal threads 71 in the bore 170. The setscrew 90 includes external threads 93 capable of threadably engaging the internal threads 71 of the saddle 70. The threaded ring 60, saddle 70 and setscrew 90 are preferably preassembled as a unit for use during the implantation of the anchor assembly 100. Alternatively the threaded ring 60, saddle 70 or set screw 90 may be supplied and assembled during the surgical implantation of the bone anchor assembly 100, or supplied as sub-assemblies where the set screw 90 is supplied connected to the saddle 70, or the saddle 70 is supplied connected to the threaded ring 60, or other alternative sub-assemblies.

With reference to FIGS. 1A, 2A and 8, to lock the adjustability of the bone anchor 10, once the rod 101 is placed into the rod receiving channel 27, 29, the three-piece locking cap 92 may be placed into the upper opening 23 of the body 20 with the U-shaped channel 78 created by the saddle arms 73 placed over the spinal rod 101. The threaded ring 60 may then be threadably engaged with the threads 21 of the body 20 to connect the locking cap 92 to the body 20. By engaging the locking cap 92 with the body 20 the rod-receiving channel 27, 29 is closed and the spinal rod 101 is captured and retained in the bone anchor assembly 100 but is still moveable with respect to the body 20 and can angulate and slide in the body 20. To lock the movement of the spinal rod 101 and the bone anchor 10 with respect to the body 20, the threaded ring is tightened and moves downward in the body 20, from an unlocked position to a locked position. As the threaded ring 60 is moved further downward in the body 20, from an unlocked to a locked position, the threaded ring 60 pushes down on the saddle 70 which in turn pushes down on the bushing 40, causing the arms 45 of the bushing 40 to collapse around the head 14 of the bone anchor 10, thereby moving the bushing 40 to a locked position and securing the position of the bone anchor 10 with respect to the body 20. Thus, the threaded ring 60 controls the locking of the bone anchor 10. To lock the rod 101 in place, the setscrew 90 is tightened and as the setscrew 90 moves down the bore 170 of the saddle, the bottom surface 95 of the setscrew 90 pushes down on the rod 101, thereby securing the position of the rod 101. This configuration provides the benefit of the anchor assembly 100 having a low profile when assembled. Other benefits include stable guidance of the saddle, a permanent preloaded saddle which may promote stability, and in the top-loading embodiments, tightening of the set-screw should result in little to no splaying.

In the alternative embodiment where the threaded ring 60, saddle 70 and set screw 90 are provided as separate elements to be assembled during implantation of the bone anchor assembly 100, the saddle 70 may be placed into the upper opening 23 of the body 20 over the rod 101. The threaded ring 60 may then be placed over the saddle 70 and threadably engaged with the threads of the body 20. As the threaded ring 60 is rotated and moved downward into the body 20 it both pushes down on the saddle and receives the upper end 88 of the saddle 70 into the bore 62 of the threaded ring. As the threaded ring 60 moves into the locked position, the adjustability and movement of the bone anchor 10 with respect to the body 20 is locked, and the ledge 63 of the threaded ring is also clipped into the ledge 87 of the saddle 70, attaching the threaded ring 60 to the saddle 70. To lock the rod 101 in place, the setscrew 90 is placed into the bore 170 of the saddle 70 and the external threads 93 of setscrew 90 are placed into engagement with the interior threads 71 of the saddle 70. The setscrew 90 is then tightened to lock the rod in place as described above.

Figure 12A:
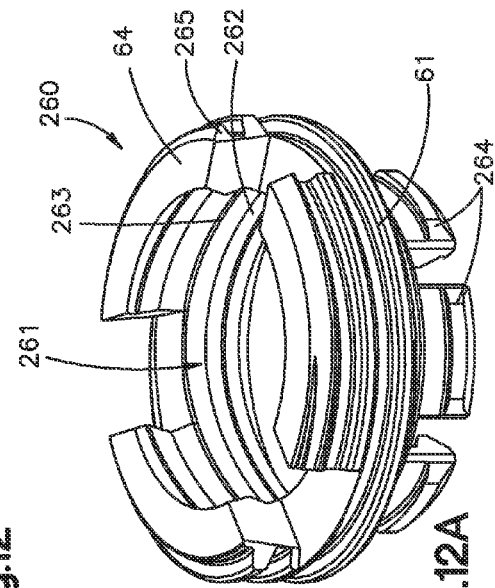
FIG. 12A illustrates a perspective view of an alternative embodiment of a threaded ring element in accordance with the present invention.

With reference to FIG. 5A, in an alternative configuration of the three-piece locking cap 92, the setscrew 90 is positioned within a threaded ring 260 (FIG. 12A), wherein the threaded ring 260 engages and interconnects with the saddle 70. The threaded ring 260 includes an upper end 265, a lower end 264, a bore 261, interior threads 263 in the bore 261, and exterior threads 61, which mate with threads on the body 20. The threaded ring 260 includes one or more ledges 262 forming one or more grooves 268 are disposed on its exterior surface proximate the lower end 264 of the threaded ring 260. The saddle 70 is provided with an internal recess 171 formed in the inner surface of the bore 170 of the saddle 70 proximate the upper end 88 of the saddle 70 which has a projection 172 that extends inward toward the center of bore 170. The projection 172 in the recess 171 preferably is capable of interlocking with the one or more ledges 262 and grooves 268 of the threaded ring 260 to interconnect the saddle 70 to the threaded ring 60. The interior threads 263 of the threaded ring 260 are capable of threadably engaging the external threads 93 of the setscrew 90. The threaded ring 60, saddle 70 and setscrew 90 are preferably preassembled as a unit for use during the implantation of the anchor assembly 100. Alternatively, the threaded ring 60, saddle 70 or set screw 90 may be supplied and assembled during the surgical implantation of the bone anchor assembly 100, or supplied as sub-assemblies where the setscrew 90 is supplied connected to the threaded ring 60, or the saddle 70 is supplied connected to the threaded ring 60, or other alternative sub-assemblies.

With reference to FIG. 5A, to lock the adjustability of the bone anchor 10, once the rod 101 is placed into the rod receiving channel 27, 29, the three-piece locking cap 92 may be placed into the upper opening 23 of the body 20 over the rod 101. The threaded ring 260 may then be threadably engaged with the threads 21 of the body 20 to connect the locking cap 92 to the body 20. By engaging the locking cap 92 with the body 20 the rod-receiving channel 27,29 is closed and the rod 101 is retained in the body 20 but is still moveable with respect to the body 20 and can angulate and slide in the rod-receiving channel 27, 29. In addition the bone anchor 10 can still angulate and move with respect to the body 20. To lock the movement of the rod and the bone anchor with respect to the body 20, the threaded ring 260 is tightened and moves downward in the body 20, from an unlocked to a locked position, and pushes down on the saddle 70. The saddle 70 in turn pushes down on the bushing 40, causing the arms 45 of the bushing 40 to collapse around the head 14 of the bone anchor 10, thereby moving the bushing to a locked position and securing the position of the bone anchor 10 with respect to the body 20. To lock the rod 101 in place, the setscrew 90 is tightened which moves the setscrew 90 down the bore 261 of the threaded ring 260 so that the bottom surface 95 of the setscrew 90 pushes down on the rod 101, thereby securing the position of the rod 101. One of the advantages of having the setscrew 90 threaded into the threaded ring 60 is that releasing the locking cap 92 by untightening the threaded ring 60 unlocks both the rod and the bone anchor in one operation.

As described above in connection with the three-piece locking cap 92 of FIGS. 1A, 2A and 8, the pieces of locking cap 92 shown in FIG. 5A may be individually assembled into the body 20 during implantation of the bone anchor assembly 100 and the procedure is substantially similar to the procedure described above but the setscrew 90 will be inserted into the threaded bore of the threaded ring 60 rather than the threaded bore of the saddle 70.

Figures 11, 13:
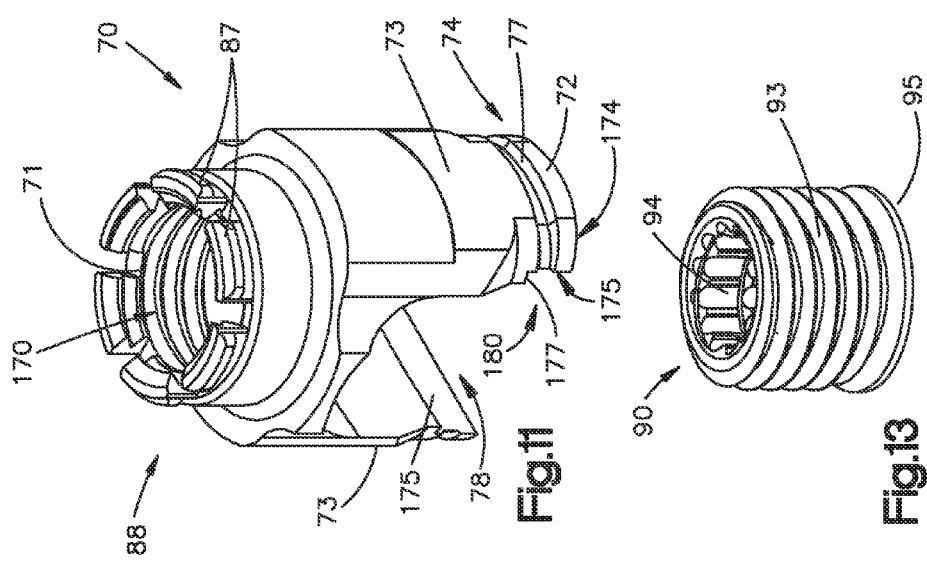
FIG. 11 illustrates a perspective view of the saddle element of the locking cap of FIG. 10.
FIG. 13 illustrates a perspective view of a set screw element in accordance with the present invention.

Referring to FIG. 12-13, the threaded ring 60, 260 and set screw 90 also preferably include drive surfaces 64, 94 (FIGS. 12-13) for engaging corresponding drive tools for securing (e.g., threading) the threaded ring 60 onto the body 20. The drive surfaces 64, 94 may take on any form now or hereafter developed for such purpose, including, but not limited to, an external hexagon, a star drive pattern, a Phillips head pattern, a slot for a screw driver, a threading for a correspondingly threaded post, etc. The drive surfaces 64, 94 may be one or more internal recesses. The specific shape of the internal recess may be chosen to cooperate with the corresponding drive tool. The drive surfaces 64, 94 may also be configured to include the first and second tool interfaces as were described above in connection with bone anchor 10.

Figure 27:
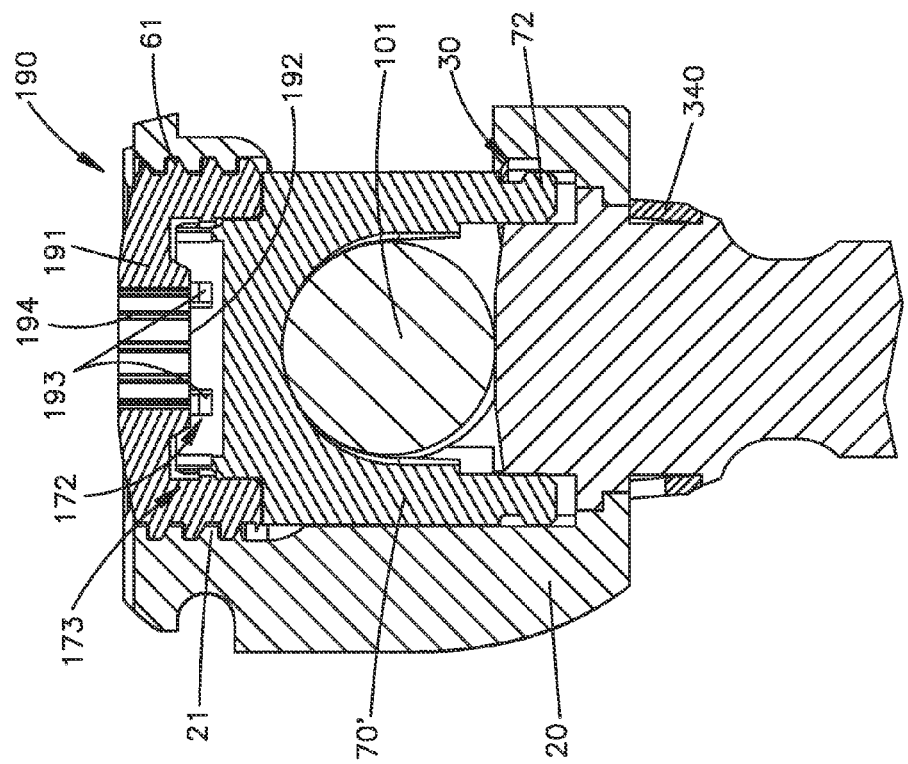
FIG. 27 illustrates a cross-sectional view of the bone anchor assembly of FIG. 22 with a two-piece locking cap.

Alternatively, with reference to FIG. 27, a two-piece locking cap 190 may be provided. The two-piece locking cap 190 includes saddle 70' and a means for engaging the body 20. The means for engaging the body 20 may include, but is not limited to, an externally threaded cap, an internally threaded cap, a quarter-turn or partial-turn locking cap, cam-lock, bayonet and lug, two-piece set screw, etc. In FIG. 21 the means for engaging the body includes locking element 191. The locking element 191 is substantially cylindrical shaped and includes a bottom surface 192 and external threads 61 which are engagable with the internal threads 21 of the body 20. While a threaded connection between the locking element 191 and the body 20 is illustrated and described, any structure for engaging the locking element 191 to the body 20 may be provided, including, but not limited to, external threads, cam-lock, quarter lock, clamps, lugs, bayonets, etc. The locking element 191 also preferably includes one or more projections 193. Saddle 70' has a rod-receiving channel 78 and saddle anus 73. Saddle 70' interconnects with the locking element 191 and preferably has a top portion 173 having one or more top recesses 172 constructed and arranged to receive or engage the one or more projections 193 of the locking element 191 to connect the saddle 70' to the locking element 191. The saddle 70' may be connected to the locking element 191 is a number of ways including snap lock, corresponding grooves and projections, etc. Preferably, the saddle 70' is independently rotatable with respect to the locking element 191. The two-piece locking cap 190 may likewise include drive surfaces 194 for engaging corresponding drive tools for securing (e.g., threading) the locking cap 190 onto the body 20.

Two-piece locking cap 190 preferably permits both locking of the rod and the adjustability of the bone anchor 10 in one step. Once the spinal rod 101 is placed into the rod-receiving channel 27, 29, the locking cap 190 may be placed into the upper opening 23 of the body 20 over the spinal rod 101 to close the rod-receiving channel 27, 29. The locking element 191 is then threaded into the body 20, so that the rod 101 is moveably retained in the rod-receiving channel 27, 29 and the bone anchor 10 can angularly adjust relative to the body 20. Once the rod 101 has been inserted and loosely closed in by the locking cap 190, the bushing 40 preferably can no longer be pushed back into the loaded position during manipulation by a surgeon to orient the system in the patient's spine. The body 20 is loosely but securely connected with the bone anchor and the bone anchor preferably can no longer accidentally pop off during manipulation of the spinal rod 101 or the bone anchor assemblies 100 or other parts of the system 5. To lock the bone anchor assembly 100, the locking element 191 is moved downward in the bore 22 of the body 20, so that the bottom surface 192 of the locking element 191 pushes down on the saddle 70, which in turn pushes down on the rod 101 and the bushing 40, thereby securing the position of both the bone anchor 10 and the rod 101.

When the locking cap 92, 190 is locked, the body 20 and the saddle 70 may splay or twist due to the forces and moments required to lock spinal rod 101, bone anchor 10, and locking cap 92, 190. Each of the side loading bone anchor assemblies, shown for example in FIGS. 1, 1A, and the top-loading bone anchor assemblies, shown for example in FIGS. 2, 2A, have potential splaying problems due to their inherent geometry. In the top-loading embodiment, because the rod-receiving channel 29 forms two upright members that are unconnected at the top, when the spinal rod 101 and bone anchor 10 are locked by tightening the locking cap 92, 190 without the benefit of counter torque on the body, the upright members are prone to separating and twisting. In the side loading bone anchor assemblies because the rod-receiving channel 27 comes in from the side, the body 20 forms an enclosed ring at the top portion supported by a single stanchion or upright member connected to the closed ring. As a result, tightening of the locking cap exerts eccentric forces, moments and tends to twist and splay the closed ring about the single stanchion and upright member. Various features may be incorporated into the anchor assembly 100 to resist or prevent the body 20 and saddle 70 from splaying or twisting.

Preferably in the side-loading bone anchor assembly 100, to resist splaying of the body and saddle, the body 20 may include one or more arm recesses 126 for receiving the lower portion 74 of the saddle arms 73. The arms 73 of the saddle 70, as shown in FIGS. 1A, 2A and 5A, preferably are sized and configured so that they are of sufficient length to extend into the arm recesses 126 when the saddle 70 is placed in the bore 22 of the body 20. Preferably, the lower portion 74 of the saddle arms 73 fit into the recesses 126. In this manner, the lower end 74 of the saddle arm 73 that extends past the side opening 143 of the rod receiving channel 27 is positioned between the bushing and the body and may be at least partially enveloped or "locked in" by one of the arm recesses 126 to hold the arm 73 in the body 20 and prevent or resist the aims 73 of the saddle 70 from splaying when the locking cap 92, 190 is locked. This feature of the saddle arms 36 extending into a recess formed in the body 20 may be applied to the top-loading bone anchor assemblies as well.

The extension of the saddle arms 73 into the lower chamber 36 of the body 20 may take many forms. In one example, as shown in FIGS. 5, 5A, the inner surface 28 of the body 20 forming the recess 126 in the lower end 34 of the body 20 that contacts the lower portion 74 of one of the saddle arms 73 may be relatively smooth, curved wall surface 35 having substantially no projections or channels. Also, as shown in FIGS. 1A and 5A, the lower portions 74 of the saddle arms 73 that are received into the recesses 126 preferably are provided with perpendicular bushing interface surfaces 76 that contacts the exterior surface 55 of the bushing 40. The perpendicular bushing interface surface 76 is disposed at the lower portion 74 of the arms 73 of the saddle 70. The perpendicular bushing interface surface 76 preferably includes a substantially flat horizontal bottom surface 174, a substantially vertical side surface 175 and a substantially flat planar horizontal surface 177, forming a notch 180. When the saddle 70 is placed into the bore 22 of the body 20, the bottom surface 174 may contact the wings 41 of the bushing 40, the side surface 175 may contact the exterior surface 55 of the bushing 40 proximate the upper end 47 and the horizontal surface 177 may contact the top surface 89 of the bushing 40. Depending upon the strength of the wings 41, the primary force exerted on the bushing 40 by the saddle arms 73 is preferably on the top surface 89 of the bushing 40. In this manner the saddle arms 73 interface with and apply force to the bushing 40 primarily through perpendicular surfaces.

Referring to FIG. 2A, the saddle 70 may alternatively be provided with an oblique bushing interface surface 75. The oblique bushing interface surface 75 is disposed at the lower portion 74 of the arms 73 of the saddle 70. The oblique bushing interface surface 75 preferably includes substantially flat bottom surface 174 and an oblique side surface 176. The bottom surface 174 of the saddle 70 is substantially flat and may contact the wings 41 of the bushing 40. The oblique surface 176 contacts the exterior surface 55 of the bushing 40 proximate the upper end 47. The bushing 40 may be provided with an oblique surface 86 that interacts with the oblique bushing interface surface 75. The lower portion 74 of the saddle arms 73 may additionally be supplied with a substantially flat horizontal planar surface 177 forming a notch 180 that may contact the top surface 89 of the bushing as the saddle arms 73 move down into the lower chamber 36 of the body 20. The oblique shape of the oblique bushing interface surface 75 may facilitate easier aligning of the saddle 70 within the bore 22 of the body 20 than the perpendicular bushing interface surface 76. Again, depending upon the strength and flexibility of the wings 41, preferably the primary force applied to the bushing by the saddle arms 73 is to the top portion of the bushing 40 rather than through the wings 41.

Figure 16A:
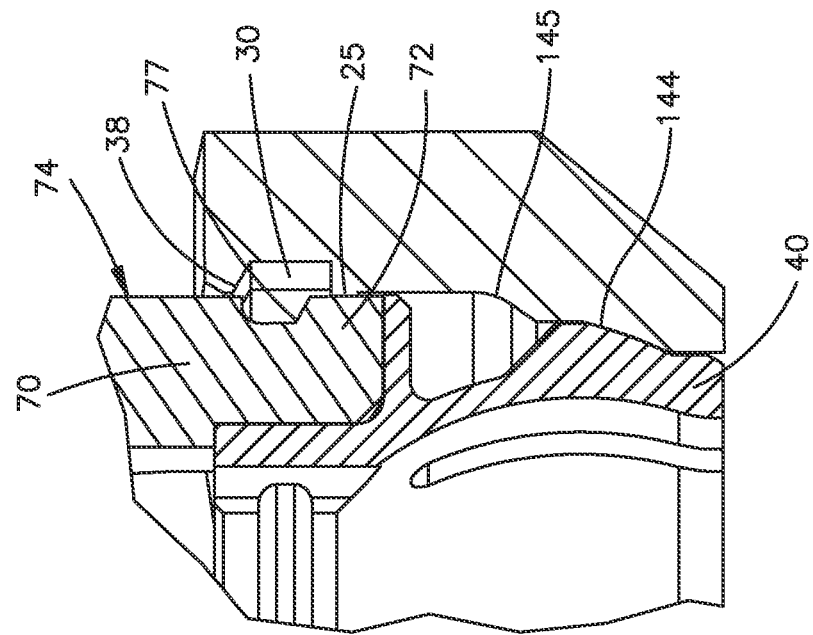
FIG. 16A illustrates a magnified view of a portion of the bone anchor assembly of FIG. 16.
Figure 16:
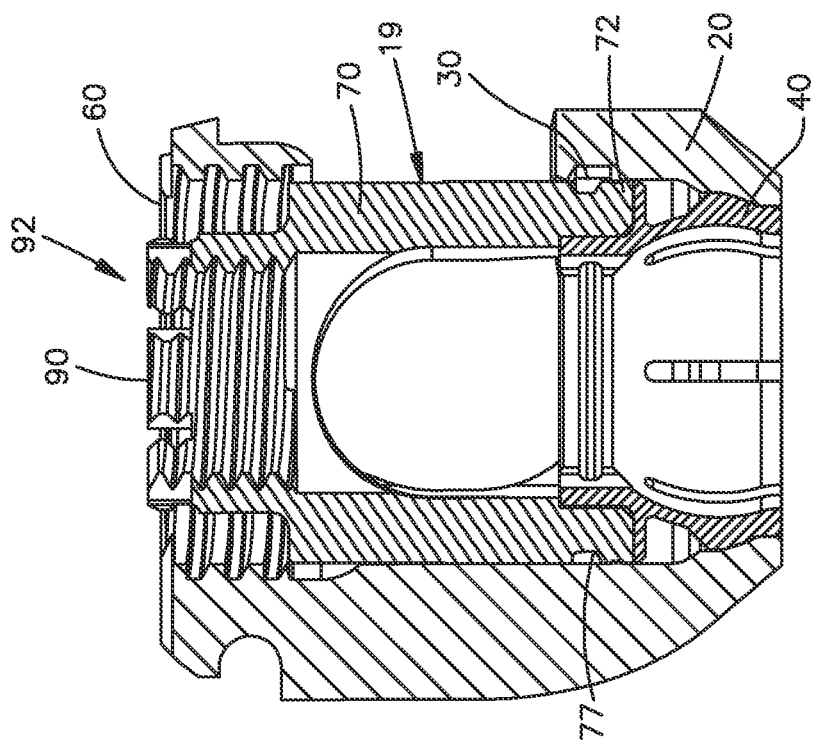
FIG. 16 illustrates a cross-sectional view of a third preferred embodiment of an anchor assembly in a locked state in accordance with the present invention.

Side-loading bone anchor assemblies 100 are also prone to splaying because of their inherent geometry creates an eccentric line of action for the forces. Referring to FIGS. 1A and 16-16A especially when utilizing a body 20 with a side-loading rod receiving channel 27, the body 20 preferably includes a recess 30 to prevent splaying of the saddle 70 and/or body 20. The recess 30 is preferably provided on the inner surface 28 at the lower end 34 of the body 20. The lower end 34 of the body additionally may be provided with inclined surface 38. The saddle 70 may additionally be provided with a protrusion 72 at the lower portion 74 of one of the saddle arms 73 configured to engage the recess 30 in the body 20. The saddle arm 73 may further be configured to include inclined surface 77 to interact with inclined surface 33 in the body 20.

When the setscrew 90 is tightened to lock the spinal rod 101, the saddle 70 has a tendency to rotate due to friction between the threads of the saddle 70 and the setscrew 90. Rotation of the saddle 70 is prevented by the rod, but the body 20, and in particular the top portion 33 of the body 20 above the opening 19 and side rod-receiving channel 27, tends to splay and move away from the lower portion 34 of the body 20. In addition, the saddle arm 73 where the side opening 19 is provided tends to move up and splay. As the saddle arm 73 starts to move up, outward and away (the saddle arm 73 has a tendency to move in path similar to an arc), the protrusion 72 on the saddle arm 73 moves into the recess 30 and the inclined surfaces 38, 77 interlock to prevent further splaying of the body 20 and the saddle arm 73. The recess 30 in the body 20 may be provided above the protrusion 72 when the saddle 70 is locked in the body 20 and the setscrew 90 has not yet been tightened. In one exemplary embodiment, the recess 30 may be about one to about two millimeters (about 1-2 mm) above the protrusion 72 when the saddle 70 locks the bushing 40 and bone anchor 10 in the body 20.

The engagement of the protrusion 74 with the recess 30 minimizes any splaying of the saddle arms 73 caused by an axial force generated when the setscrew 90 is rotatably tightened whereby forces act on the saddle 70, pushing the arms 73 of the saddle 70 outward with respect to the bore 22. While the protrusion 72 has been shown and described with inclined surface 77, and recess 30 has been shown and illustrated with inclined surface 38, the protrusion 72 and recess 30 may be provided with perpendicular interacting surfaces, or other interacting and interfacing surfaces and configurations.

In top-loading bone anchor assemblies 100 (e.g., FIG. 2-2A), splaying of the arms 73 of the saddle 70 from an axial force being applied to the saddle 70 when the locking cap 92, 190 is placed in the locked position may be prevented and/or at least inhibited because both arms 73 of the saddle 70 are supported along their length by the body 20, and by the arms extending into the recess 126 formed in the body 20. When the setscrew is twisted in the saddle 70, the saddle 70 has a tendency to twist and rotate due to friction from the threads. Rotation of the saddle however is prevented by the spinal rod, but the spinal rod and the rotation forces have a tendency to splay the saddle arms 73. Splaying of the saddle 70 is resisted because the saddle arms 73 extend into the recesses 126 which hold the ends of the arms 73 in position in the lower portion 34 of the body 20.

Referring to FIGS. 14-15, in another preferred embodiment, to prevent or minimize the splaying of the saddle arms 73 or splaying or twisting of the body 20, particularly in top-loading bone anchor assemblies, the saddle 70 may be constructed and arranged to be form-fitted to the size and shape of the body 20. That is, the saddle 70 includes an exterior surface 81 that maximizes contact between exterior surface 81 of the saddle 70 and the inner surface 28 of the body 20 when the saddle 70 is placed into the bore 22 of the body 20 and locked in place by the locking cap 92, 190. Usually, when the locking cap 92, 190 is tightened, the friction between the threads of the body 20 and locking cap 92, 190 may cause the body 20 to rotate or twist. The geometry of this "form fitted" saddle 70 controls and mitigates this rotation or twisting because it better integrates the body 20 and locking cap 92, 190, thereby permitting less movement of each individual component (e.g., the body 20 or the saddle 70). That is, the saddle 70, and particularly the saddle aims 73 are form-fit to the geometry of the bore 22 in the body 20. The force tending to twist the body 20 is transmitted to and resisted by the saddle arms 73 and the inverse U-shaped channel 78 of the saddle 70. The force tending to twist the body 20 is transmitted to the saddle arms 73 which because of their form-fit and integration into the body 20 creates a stronger construct. The saddle 70 is held in position by the rod 101 and the bushing 40 such that the saddle 70 supports the body through the form-fit and extra mass and strength of the saddle arms 73 which resists twisting of the body 20.

To maximize the effectiveness of the saddle 70 with the form-fitted exterior surface 81, the exterior surface 81 of the saddle arms 73 preferably fill any recess and space formed in the axial bone 22 in order to provide more mass and material to better support the body 20 by creating a more solid form. In addition, to maximize the effectiveness of the form-fitted exterior surface 81, the exterior surface 81 of the saddle arms 73 preferably contacts the inner surface 28 at substantially right angles. That is, the exterior surface 81 of the saddle 70 may be arranged and configured to have a side surface 83 that is substantially perpendicular to the back surface 84 of the saddle arms so that the cross-section of the arms 73 are substantially square or rectangular shaped, as shown in FIG. 14. The body 20 is likewise formed with perpendicular surfaces to correlate and match surfaces 83, 84 and so that the saddle and body are close-fitting. Such a shape optimally prevents twisting of the body 20 and saddle 70. That is, as the locking cap 92, 190 is tightened which tends to twist the body, the body 20 transfers the force to the saddle 70. Since the saddle 70 is form-fitted very little to no twisting of the body 20 occurs before the force is transmitted to the saddle 70 whereby the saddle 70 helps to resist the twisting. Alternatively, the exterior surface 81 of the saddle 70 may be arranged and configured to have a substantially oblong or oval shape, as shown in FIG. 11, or other non-symmetrical or keyed shapes, which because of the form-fit between the body 20 and the saddle 70 resists splaying of the upright members of the top loading body 20. Other shapes and configurations of the saddle 70 and the interfacing shape of the inner surface 28 of the body 20 are contemplated and the saddle arm shapes are not limited to the shapes shown and described. The form-fitting of the saddle 70 and body 20 can also be applied to side-loading bone anchor assemblies.

Figure 17:
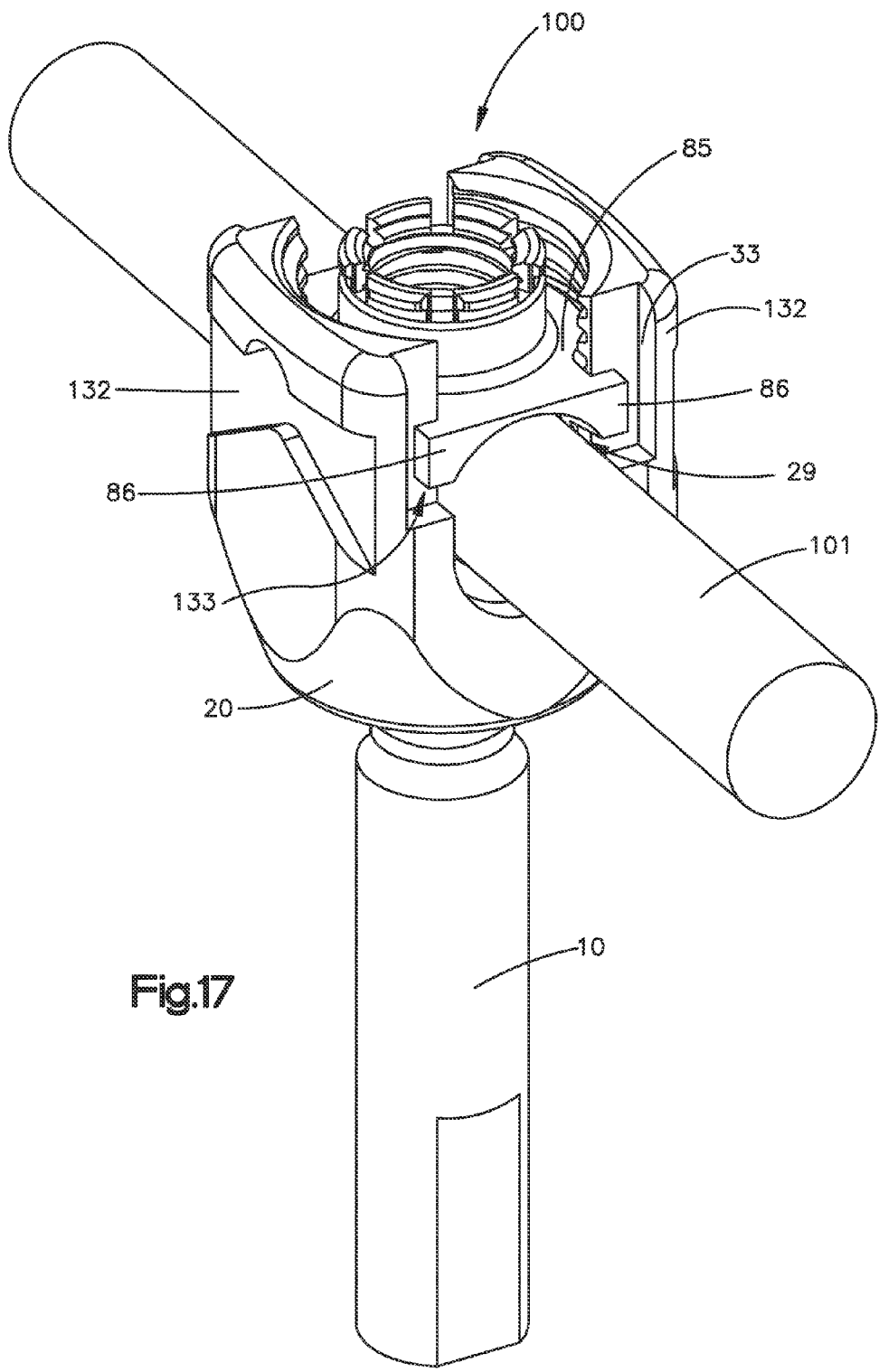
FIG. 17 illustrates a perspective view of a fourth preferred embodiment of the bone anchor assembly of the present invention.

An alternative top-loading bone anchor assembly 100 with features to resist and prevent splaying is shown in FIGS. 17 and 18. The body 20 in the embodiment of FIGS. 17 and 18 may be provided with an exterior recess 133 disposed on the outer surface 132 at the upper end 33 of the body 20, proximate the rod-receiving channel 29. The saddle 70 preferably includes one or more wings 86, preferably positioned adjacent the arms 73 of the saddle 70. As best shown in FIG. 17, the one or more wings 86 may have a generally T-shape and extend from the saddle 70. After the rod 101 is placed into the rod-receiving channel 29, the saddle 70 may be lowered into the bore 22 of the body 20. As the saddle 70 is lowered the one or more wings 86 are placed into engagement with the exterior recess 133. The engagement of the one or more wings 86 with the exterior recess 133 provides for a more integral link between the saddle 70 and the body 20, and may thus help minimize any splaying of the body 20 or saddle 70.

Figure 19:
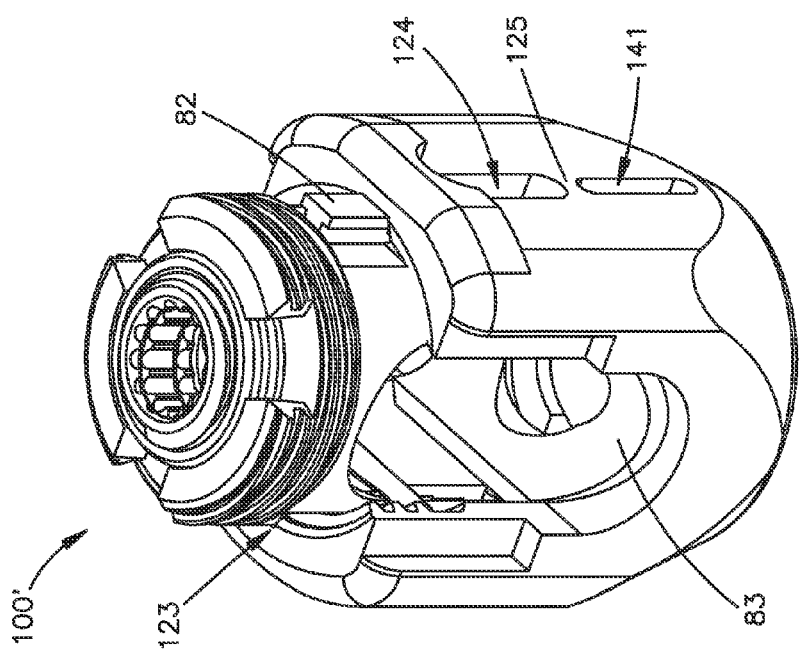
FIG. 19 illustrates a perspective view of an fifth preferred embodiment of the bone anchor assembly of the present invention.

Referring to FIGS. 19-19D, in another preferred embodiment, the body 20 of the bone anchor assembly 100' may be provided with one or more wing guides 123, one or more wide guide locks 124, one or more narrow guide locks 141, and one or more guide stops 125. The wing guides 123 are preferably recesses formed on the inner surface 28 of the body 20. The wing guides 123 preferably run in the direction of the longitudinal axis 32 of the bore 22. The guide locks 124, 141 are preferably openings formed in the sides of the body 20. The guide locks 124 preferably may be wider than guide locks 141 and are preferably positioned above the narrow guide locks 141. Each guide stop 125 is positioned between one of the narrow guide locks 141 and the wide guide locks 124, separating each guide lock 141 and guide lock 124.

Referring to FIGS. 19, 19C, the saddle 70 additionally may include wings 82 to guide the saddle 70 down the bore 22 of the body 20 via the wing guides 123. The wings 82 may be protrusions of any shape or size formed on the saddle 70. The wing guides 23 may be a straight sided channel as shown in FIG. 19B or wing guides 123 can be T-shaped to interlock with the T-shaped wings 82 shown in FIGS. 19 and 19C. The wing guides 123 on the body 20 and the wings 82 on the saddle 70 may be configured and arranged to interlock the saddle 70 with the body. For example, the wing guides 123 and wings 82 may form a dove-tail sliding joint or T-shaped joint to interlock the pieces. The wings 82 preferably are sized and arranged to snap into the wide guide locks 124 in the body 20.

Referring to FIGS. 19A, 19D a bushing assembly 162 is preferably provided in bone anchor assembly 100'. The bushing assembly 162 preferably is a two-piece assembly including a bushing 160 and a sleeve 183. The bushing 160 may include one or more slots 42 extending from the lower end portion 46 thereof so that at least a portion of the bushing 40 is: (i) radially expandable so that the head 14 of the bone anchor 10 can be inserted through the lower opening 142 in the lower end portion 46 and into the interior cavity 51 of the bushing 160 and (ii) radially compressible to compress or lock against the head 14 of the bone anchor 10 when radial forces are applied thereto. In the preferred embodiment, the slots 42 define a plurality of flexible arms 45. In another preferred embodiment, a single slot 42 defining an expandable and compressible C-type bushing element or spring-clip like element may be provided. The bushing 160 may include a groove or recess 161 disposed proximate the upper end 47 of the bushing 160 and the sleeve 183 may be preferably configured and arranged to fit over and snap into the recess 161. The sleeve 183 preferably can rotate about longitudinal bushing assembly axis 49. The sleeve 183 preferably has a generally U-shaped channel for receiving the spinal rod, and is constructed and arranged to fit within the bore 22. The bushing assembly 160 is preferably inserted into axial bore 22 preferably from top opening 23 as described for bushing 60. The sleeve 183 may also preferably be provided with one or more wings 85, preferably two wings 85, to guide the sleeve 183 down the bore 22 of the body 20 via the wing guides 123. The wings 85 may be protrusions of any shape or size, but are preferably narrower than the wings 82 formed on the saddle 70. The wings 85 are preferably sized and arranged to slide down the narrower guide locks 141 in the body 20 and preferably provide rotational stability to the bushing assembly 182 and the sleeve 183. To this end, the wings 85 may be arranged to bend slightly outwards with respect to the sleeve 183 such that the wings 85 may be snapped into the narrow guide locks 141. In an alternate embodiment, the sleeve 183 and the bushing 40 may be constructed as a single, integral component.

The bushing 160 and the sleeve 183 are preferably preassembled and installed into the body 20 together in production. To do so, the bushing 160 is inserted through the upper opening 23 of the body 20. The wings 85 of the sleeve 183 may then preferably be aligned with the wing guides 123 and inserted through the upper opening 23. Once the narrow wings 85 are moved past the guide stops 125, the narrow wings 85 may preferably snap into the narrow guide locks 141. In this configuration, the sleeve 183 facilitates proper alignment of the bushing 160 within the body 20 so that the body 20, bushing 160, and sleeve 183 subassembly may pop-on over the head 14 of the bone anchor 10. The wings 85 on the sleeve 183 contained within the narrow guide locks 141 permits vertical movement of the sleeve 183, prevents or resists rotation of the sleeve 183 about axis 32 of the body so that the U-shaped channel of the sleeve 183 remains properly aligned in the body, and preferably, with guide stops 125, prevents the bushing assembly 182 from detaching from the body 20. The guide stops 125 preferably also prevent the sleeve 183 from slipping back during click-on of the bone anchor head.

Once the body 20, bushing 160, and sleeve 183 are connected to the bone anchor 10, the rod 101 may be inserted into the rod-receiving channel 29. The saddle 70 with wings 82 may then be installed. To do so, the wings 82 of the saddle 70 are aligned with the wing guides 123 and the saddle 70 is moved downwards in the bore 22 of the body 20 and placed over the rod 101 and into contact with the sleeve 183. The lower portion 74 of the saddle arms 73 may be configured with notched surfaces, recesses, grooves and projections so that the saddle arms 73 overlap, envelope or interlock with the top portion of the sleeve 183 to better contain the spinal rod 101. The engagement of the saddle arms 73 with the sleeve 183 is preferably rotationally stable so that twisting of the saddle 70 and body 20 is resisted. That is the connection between the sleeve 183 and saddle 70 is preferably rotationally stable. The engaging surfaces between the sleeve 183 and the saddle 70 preferably assist or provide the rotationally stable connection between the two parts. The locking cap 92, 190 may then be threadably engaged with the body 20 and moved into a locked position. The locking of the locking cap 92, 190, urges the saddle 70 down into the sleeve 183, and hence moves the bushing assembly 162 downwards. This causes the arms 45 of the bushing 160 to collapse over the head 14 of the bone anchor 10, thereby securing the position of the bone anchor 10 with respect to the body 20.

An alternative embodiment of bushing 40 is provided in FIG. 20. The top loading bone anchor assembly 100' of FIG. 20 includes a two-piece bushing assembly 162 having a bushing 160 to capture the head of the bone anchor and a sleeve 183' that attaches to bushing 40 and interacts with saddle 70. Sleeve 183' operates similar to sleeve 83 but does not include wings 85. In both embodiments of two-piece bushing assembly 182, the body has an enlarged chamber portion whereby the bushing is expandable to permit the head of the bone anchor to be received within the cavity 51 of the bushing 160. Preferably a stop mechanism, such as for example, guide stops 125, resist or prevent the bushing assembly 182 from being detached from the body and aligns the expandable portion of the bushing with the enlarged portion of the chamber so that the bushing can expand. The body also preferably would contain a chamber position that will compress the bushing to facilitate locking of the bone anchor.

The use of bone anchoring system 5, and in particular the use of bone anchor assembly 100, 100' is generally as follows. First, the shaft 15 of the bone anchor 10, preferably is inserted into a patient's bone, preferably the pedicle of the vertebral body 200 or the sacrum, using an instrument such as a driver or power tool that interfaces with the drive surface 17 at the proximal end of the bone anchor 10. A second bone anchor 10 may be implanted at a second site. As many bone anchors 10 as needed may be implanted at any appropriate point during the course of the surgery. The bushing 40 preferably is positioned in the loading position within the lower chamber 36 of the body 20 during manufacture. In an embodiment including a bushing assembly 162, the bushing 160 and sleeve 183 may be inserted into the body 20 during manufacture. The position of the bushing 40, 160 preferably enables the flexible arms 45 of the bushing 40, 160 to radially expand within the axial bore 22 of the body 20 so that the head 14 of the bone anchor 10 can be inserted through the lower opening 24 of the body 20 and into the interior cavity 51 of the bushing 40. The body 20 with bushing 40 retained therein is then snapped over the head 14 of the bone anchor 10 as the arms 45 of the bushing 40 expand to accept the head 14 of the bone anchor 10.

After the body 20 with the bushing 40, or bushing assembly 162, is snapped over the head 14 of the bone anchor 10, the body 20 may still angulate with respect to the bone anchor. Another anchor assembly 100 or a second bone fixation element with a rod-receiving channel may be assembled at a second site to receive the rod 101. One end of the rod portion 101 may then be inserted either from the top (in the top-loading bone anchor assembly) or the side (in the side-loading bone anchor assembly) into the rod-receiving channel 27, 29 of one of the bone anchor sub-assemblies. The locking cap 92, 190 may then be inserted into the bore 22 of the body 20 over at least a portion of the rod 101 to capture the rod 101.

To allow the surgeon to adjust the orientation of the anchor assemblies 100, the rod portion 101 may be movably retained in the rod-receiving channel 27, 29 of the body 20 and the bone anchor can polyaxially rotate with respect to the body 20. To do so, the saddle 70 may be placed into the bore 22 of the body 20 and the locking cap 92, 190 may be provisionally or lightly threaded into the body 20 to capture to spinal rod 101. The provisional threading of the locking cap 92, 190 may cause the bushing 40 to move toward the lower chamber surfaces 37 and out of the loading position, thus preventing the body 20 with the bushing 40 from popping off the head 14 of the bone anchor 10. The surgeon may apply adjustments as required before locking the bone anchor 10 or rod 101 into the anchor assembly 100 or locking the second anchor assembly 100. Once the desired orientation of the anchor assembly 100 is achieved, the locking cap 92 or the two piece locking cap 190 may be operated to place the bone anchor 10 and rod 101 into a locked position. The surgeon may lock the anchor assembly 100 and second anchor assembly 100 in any desired sequence.

To lock the anchor assembly 100, once the rod 101 is positioned in the rod receiving channel 27, 29, the threaded ring 60, 260 is tightened causing the threaded ring 60, 260 to move downwards in the bore 22 of the body 20, causing it to push down upon the saddle 70, which in turns pushes down upon the bushing 40, causing the bushing 40 to move downwards in the lower chamber 36 of the body 20. As the bushing 40 is moved further down relative to the body 20, the bushing 40 contacts the lower chamber surfaces 37, which apply a radial inward force to the flexible arms 45, which in turn causes the flexible arms 45 to compress against the head 14 of the bone anchor 10, thereby securing the position of the bone anchor 10 with respect to the bushing 40 and hence with respect to the body 20. The lower chamber surface 37 and the outer surface 55 of the bushing 40 preferably form a generally line contact as described in International App. No. PCT/US2008/070670 the entire contents of which are incorporated herein by reference. To secure the rod 101, the setscrew 90 is tightened which moves the setscrew 90 downward in the bore 22 of the body 20. The bottom surface 95 of the setscrew 90 (FIG. 1A) pushes down on the rod 101, securing the rod 101 in place.

In an embodiment utilizing a two-piece locking cap 190 the exterior threads 61 of the locking element 191 are placed into engagement with the internal threads 21 of the body 20, moving the locking element 191 downward in the axial bore 22 of the body 20. As the locking element 191 moves downward, the locking element 191 exerts a force upon the saddle 70, causing the saddle 70 to push down upon the rod 101, and/or bushing 40, locking the position of the rod 101 and causing the bushing 40 to move downwards in the lower chamber 36 of the body 20, securing the position of the bone anchor 10 with respect to the bushing 40, and hence, with respect to the body 20, as described above. The same process may be applied to a second anchor assembly 100, 100' to secure the other end of the rod 101.

If desirable, a surgeon may pop-off the body 20 from the bone anchor 10, in situ, after the anchor assembly 100 is engaged in the locked configuration. Specifically, the locking cap 92, 190 of the anchor assembly 100 may be removed from the body 20 and the rod 101 may be disengaged and extracted from the rod-receiving channel 27, 29 of the anchor assembly 100 and the second anchor assembly 100. These steps may be executed in any desired sequence. A tool (not shown) engages the bushing 40 and the body 20 and applies a force to the bushing 40 to move the body 20 downwardly toward the bone anchor 10. The generally line contact between the body 20 and the bushing 40 is released and the bushing 40 is urged upward with respect to the body 20 so that the bushing 40 is in the loading position. Enough force may be applied to the assembly to move the wings 41 up past the optional second stops 26, if provided in the body 20, so that the bushing 40 is moved to the loading/unloading position. In the loading position, the flexible aims 45 can flex outwardly within the lower chamber 36 of the body 20 to permit popping-off of the body 20 and bushing 40 from the head 14 of the bone anchor 10. While the bushing 40 and body 20 may be removed from the bone anchor 10 as described, their release from the bone anchor 10 preferably is non-destructive. The bushing 40 and body 20 may be reapplied to the bone anchor 10 if desired.

With reference to FIGS. 21-34, bone anchor system 5 may also preferably be used in conjunction with a monorotational bone anchor assemblies 100", which may include bone anchors 210, 310, 410, 510, 610 rather than polyaxial bone anchor 10. The bone anchor 210, 310 may be preassembled in the body or a bone anchor 410, 510, 610 may be provided that permits the surgeon to "click-on" the body in-situ. These monorotational bone anchor assemblies generally include the locking caps 92, 190 as described above for use in conjunction with bone anchor 10 and include a variation of body 20 modified to operatively associate with or connect to the various bone anchors 210, 310, 410, 510 and 610. The monorotational bone anchor assemblies generally do not include bushing 40 or bushing assembly 162. The monorotational bone anchor assemblies may include a side loading body 20' having a side loading channel 27, or a top loading body 20' having a top loading rod-receiving channel 29.

With reference to FIGS. 21 and 21A, in a preferred embodiment utilizing a monorotational bone anchor, the anchor assembly 100 includes a bone anchor 210, a fastener element 240, a body 20', and a locking cap 92, 190 (not shown). The bone anchor 210 includes an upper portion 211 and a lower portion 212. The upper portion 211 includes the head 214 of the bone anchor 210, a fastener engagement element 215, and one or more head engagement elements 213. Each head engagement 213 may assume the form of a recess, protrusion or combination of both around the head 214 of the bone anchor 210 without deviating from the scope of the present invention. The fastener engagement element 215 is preferably a recess or groove formed in the head 214 and is configured and arranged to receive the fastener element 240. The fastener element 240 may be substantially C-shaped with an opening that is configured to receive the bone anchor 210, e.g., a C-clip. The body 20 may be formed with a shoulder, groove, ledge, projection or a combination to prevent the head 214 from passing through the lower opening 24, and preferably engages the head 214.

To assemble the anchor assembly 100, the bone anchor 210 is placed into the bore 22 of the body 20 through the top opening 23 or the rod-receiving channel 27, 29. The lower portion 212 of the bone anchor 210 exits the body 20 through the lower opening 24. The head engagement elements 213 contact the lower chamber surfaces 37 causing the head 214 to be retained within the lower chamber 36. The fastener element 240 may then be clipped onto the fastener engagement element 215 around the head 214 to prevent the bone anchor 210 from moving back upwards in the bore 22 of the body 20. Once the bone anchor/body subassembly is complete, the bone anchor/body subassembly may be implanted into a patient's bone. The fastener element 213 retains the bone anchor 210 in the body 20 and permits the body 20 to rotate about vertical axis 32 so that the rod-receiving channel 27, 29 can be oriented in a desirable direction. A spinal rod 101 may then be placed into the rod receiving channel 27, 29 of the body 20 and the locking cap 92, 190 engaged to secure the position of the rod 101, and preferably the orientation of the body 20 with respect to the bone anchor 210.

Referring to FIGS. 22-27, anchor assembly 100" includes a bone anchor 310 with an upper portion 311 and a lower portion 312, a fastener element 340, body 20, and locking cap 92, 190. The upper portion 311 includes the head 314 of the bone anchor 310, a fastener engagement element 315, and one or more head engagement elements 313. Each head engagement element 313 may assume the form of a recess, protrusion or combination of both around the head 314 of the bone anchor 310 without deviating from the scope of the present invention. The fastener engagement element 315 may be a recess formed in the head 314, which is constructed and arranged to receive the fastener element 340. The fastener element 340 may be substantially ring shaped and may be provided with one or more partial of full length slots 342 to allow the fastener element 340, e.g., a spring clip, to compress and expand so that it can slide and lock onto fastener engagement element 315. The body 20 may be formed with a shoulder, groove, ledge, projection or a combination to prevent the head 314 from passing through lower opening 24, and preferably engages the head 314.

Figure 25:
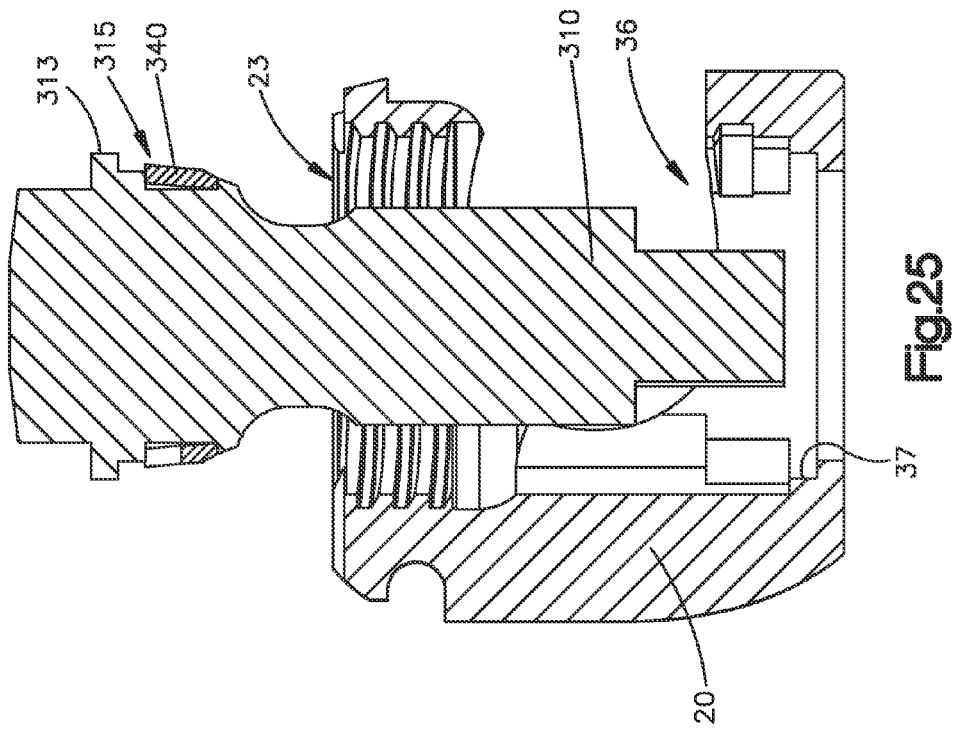
FIG. 25 illustrates a side cross-sectional view of a fastener element in a second state with a screw captured therein being inserted into the body element in accordance with the bone anchor assembly of FIG. 22.
Figure 24:
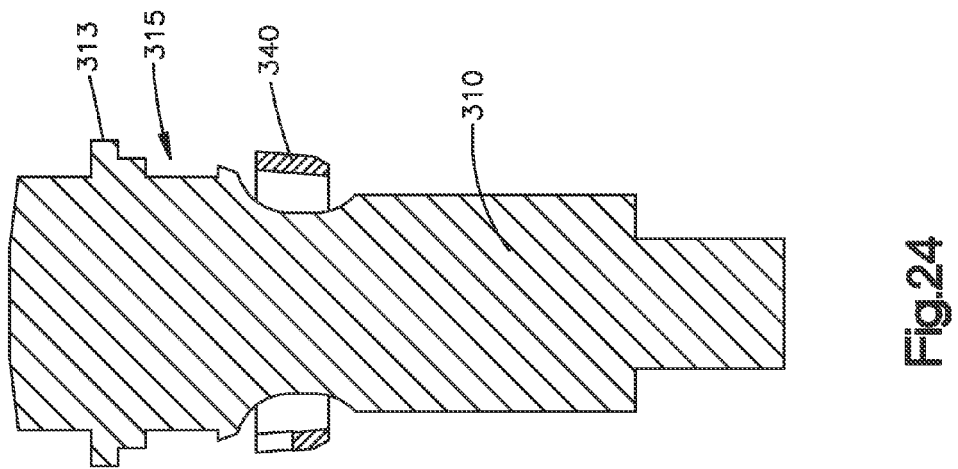
FIG. 24 illustrates a side cross-sectional view of a fastener element in a first state with a bone screw captured therein in accordance with the bone anchor assembly of FIG. 22.
Figure 26:
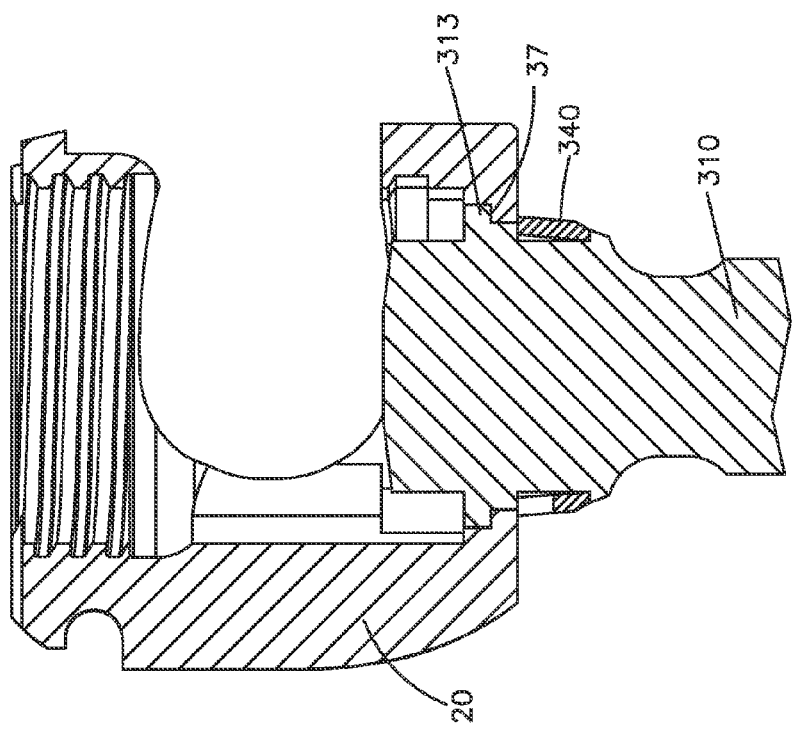
FIG. 26 illustrates a side cross-sectional view of the bone anchor assembly of FIG. 25 in a locked position within the body element.

To assemble the anchor assembly 100, the bone anchor 310 is placed through the fastener element 340 and the fastener element 340 is pushed up the bone anchor 310 (FIG. 24) until it reaches the fastener engagement element 315, where it locks into place around the fastener engagement element 315. The bone anchor/fastener element assembly is then inserted into the bore 22 of the body 20 through the upper opening 23 of the body 20 as shown in FIG. 25. The lower portion 312 of the bone anchor 310 exits the body 20 through the lower opening 24. The head engagement elements 313 contact the lower chamber surfaces 37 causing the head 314 to be retained within the lower chamber 36. The fastener element 340 contracts to exit the bore 22 of the body 20 through the lower opening 24 and expands once the fastener element 340 has traveled beneath the body 20 to a size (diameter) larger than lower opening 24 to prevent the bone anchor 310 from moving back up through the bore 22 of the body 20 (FIG. 26). Once the bone anchor/body subassembly is complete, the anchor/body subassembly may be implanted into a patient's bone. After implantation of the bone anchor/body subassembly, the body 20 is rotatable about the bone anchor 310 so that the orientation of the rod-receiving channel 27, 29 can be adjustable by a user. A spinal rod 101 may then be placed into the rod-receiving channel 27, 29 of the body 20 and the locking cap 92, 190 engaged with the body 20 to capture the rod 101. The locking cap 92, 190 may then be tightened to lock the position of the spinal rod 101, and preferably the orientation of the body with respect to the bone anchor 310 (FIG. 27).

Referring to FIGS. 28-29, in a further preferred embodiment of the monorotational bone anchor assembly, the anchor assembly 100" includes a bone anchor 410 with an upper portion 411 and a lower portion 412, a fastener element 440, a body 20, and locking cap 92, 190 (not shown). The upper portion 411 includes the head 414 of the bone anchor 410, a fastener engagement element 415, and one or more head engagement elements 413. Each head engagement 413 may assume the form of a recess, groove, or preferably a protrusion or projection, or a combination of grooves/recesses and protrusions/projections disposed around the head 414 of the bone anchor 410. The fastener engagement element 415 may be a recess formed in the head 414, which is configured and arranged to receive the fastener element 440. The fastener element 440 may be substantially C-shaped ring with an opening 450 that is configured to expand to clip onto the bone anchor 410 from the side, e.g., a C-clip. The fastener element 440 may include a first oblique side surface 441 that is inclined and a side surface 448. The fastener element attaches to the fastener engagement element to form a protrusion on the head 414 of the bone anchor 410.

To attach the fastener element 440 to the bone anchor 410 the opening 450 is expanded and the clip is inserted into the recess 415. To stabilize the fastener element 440 in the recess 415 that forms the fastener engagement element, the fastener element 440 may be distorted to friction fit the fastener element 440 in the recess 415. In one embodiment, the fastener element 440 is twisted about axis 402 so it is deformed so that it is slightly helically shaped so that it is friction fit in the recess 415. It is believed that friction-fitting the fastener element 440 to take up or resist any free play, "slop" or movement (lateral) may reduce jamming of the fastener element 440 in the body 20. The fastener element 440 may further include an optional inclined bottom surface 442. The body 20 is preferably provided with a recess 421 (FIG. 29) on the inner surface 28 of the lower chamber 36 to receive the oblique protrusion formed by the fastener element 440 connected to the bone anchor 410.

The head 414 of the bone anchor 410 is received into the body 20, and the protrusion formed by the fastener element 440 engages the recess 421 to connect the bone anchor 410 to the body 20 and prevent the bone anchor 410 from falling out of the body 20 once the head 414 is captured within the body 20. The head 414 of the bone anchor 410 is inserted through the lower opening 24 and the oblique surface 441 and side surface 448 contacts the body surrounding the lower opening 24 which compresses the fastener element 440 so that the fastener element 440 can pass through the opening 24. As the bone anchor 410 with fastener element 440 progresses up the body 20 and the side surface aligns with the recess 421 the fastener element 440 expands into the recess 421. A shoulder 408 on the bone anchor 410 larger than bottom opening 24 prevents the bone anchor 410 from passing through the opening 24. The expansion of fastener element 440 and its bottom surface 442 abutting against the bottom wall of the recess 421 prevents the bone anchor 410 from being detached from the body 20. The recess 421 may also include an optional inclined surface 438 to cooperate with inclined surface 442 to further resist the bone anchor 410 from being detached from the body 20 by being pulled back out of the opening 24.

Referring to FIGS. 30-31, in another preferred embodiment of the monorotational bone anchor assembly 100"', the fastener element 540 may be substantially ring shaped and configured to slide over the head 514 of the bone anchor 510 onto the fastener engagement element 515, which is preferably a recess disposed on the head 514 of the bone anchor 510 configured to receive fastener element 540. The fastener element 540 includes an oblique side surface 541 that preferably forms an oblique protrusion on the head 514 of the bone anchor 510 when clipped onto the fastener engagement element 515. The body 20 is preferably provided with a recess 521 (FIG. 31) on the inner surface 28 of the lower chamber 36 to receive the oblique protrusion formed by the fastener element 540 connected to the head 514 of the bone anchor 510. The head 514 of the bone anchor 510 is received into the body 20, and the protrusion formed by the fastener element 540 engages the recess 521 to prevent the bone anchor from falling out of the body 20 once the head 514 is clipped into place within the body 20.

In operation the fastener element 440 is clipped into the fastener engagement element 415 of the bone anchor 410. Alternatively, the fastener element 540 is slid over the bone anchor 510 and onto the fastener engagement element 515. The surgeon may then implant the bone anchor 410, 510 into a patient's bone. The surgeon may then pop on the body 20 over the head 414, 514 of the bone anchor 410, 510. The head 414, 514 of the bone anchor 410, 510 is received into the body 20 through the lower opening 24 and is moved up through the lower chamber 36 until the fastener element 440, 540 passes the recess 421, 521 in the lower chamber 36. When the bone anchor 410, 510, and hence the head 414, 514, is moved upward to engage the recess 421, 521 with the fastener element 440, 540, the bone anchor 410, 510 is clipped into place. The body 20 may still rotate with respect to the bone anchor 410, 510 so that the rod receiving channel 27, 29 can be oriented by a user. The rod 101 may then be placed into the rod-receiving channel 27, 29 of the body 20 and the locking cap 92, 190 is engaged with the body 20 to secure the position of the rod 101, and preferably the body 20 with respect to the bone anchor 410, 510.

With reference to FIGS. 32-34, in a still further preferred embodiment, the anchor assembly 100" includes a bone anchor 610, a body 20, a fastener element 640, and a locking cap (not shown). The bone anchor 610 includes an upper end 611 and a lower end 612. The upper end 611 includes the head 614 of the bone anchor 610, which is sized and configured to be received within the body 20 and may also include a flange 615 disposed on the head 614 of the bone anchor 610 forming a shoulder or ledge which will interact with the fastener element 640. An oblique or inclined surface 609 is also formed on the head 614.

The fastener element 640 is preferably in the form of a bushing and includes a bore 648 and a lower end portion 646 sized and configured to capture at least a portion of the head 614 of the bone anchor 610. The bore 648 extends from an upper opening 649 at the upper end 647 to the lower end 646 so that, for example, a drive tool, such as, for example, a screw driver, can be inserted through the fastener element 640 and into engagement with the bone anchor 610 so that the bone anchor 610 may be rotated into engagement with the patient's vertebra 200. The lower end portion 646 of the fastener element 640 preferably includes an interior cavity 651 for receiving and securing the head 614 of the bone anchor 610 to secure the position of the bone anchor 610 with respect to the body 20. The fastener element 640 also includes one or more slots 642 extending toward the lower end 646, wherein the slots 642 define a plurality of flexible arms 645.

The fastener element 640 may also include a recess 653 on its outer surface 652 formed by flanges 654 on the flexible arms 645 and a ledge portion 655 formed on the upper portion of the fastener element 640. The fastener element 640 is additionally sized and configured to fit within the lower chamber 36 of the body 20. The lower chamber surfaces 37 of the body 20 are preferably constructed and arranged to receive the fastener element 640 and may additionally include a protrusion 621 on the inner surface 28 at the lower chamber 36 of the body 20 forming a shoulder 625.

The fastener element 640 is inserted from the top opening 23 or the rod-receiving channel 27, 29 into the lower chamber 36 of the body so that the ledge portion 655 of the fastener element 640 rests on the protrusion 621 formed on the inner surface 28 of the lower chamber 36 of the body 20. As the fastener element 640 is inserted into the chamber 36, the oblique or chamfered surface 656 of the flanges 654 of the arms 645 contact the protrusion 621 and the arms 645 are compressed and deflected inward until the flanges 654 move below the protrusion 621 at which time the arms 645 expand beyond the protrusion 621 so that the fastener element 640 is captured in the body 20. The ledge portion 655 formed on the fastener element 640 abuts against the protrusion 621 to prevent the fastener element 640 from further downward movement in the body 20. Below the protrusion 621 is an expanded chamber portion 636 that permits the arms 645 of the fastener element 640 to expand while in the body 20 to capture the head 614 of the bone anchor 610 as will be described below.

In operation, bone anchor 610 is implanted in the patient's bone. The fastener element 640 is prevented from falling out of the body 20 through the lower opening 24 of the body 20 by the ledge portion 655 engaging the protrusion 621. The fastener element 640 is also prevented from moving back up the bore 22 of the body 20, by flanges 654 engaging the protrusion 621. Preferably there is a predetermined amount of free play to permit the fastener element 640 to move a limited longitudinal distance within the lower chamber 36. The body/fastener element subassembly may then be popped over the bone anchor 610. As the bone anchor 610 is inserted into the lower opening 24 of the body 20 the bone anchor 610 moves the fastener element 640 up into the body 20 so that the flanges 654 of the fastener element 640 contacts and abuts against the protrusion 621. Continued movement of the bone anchor 610 up into the body causes oblique surface 609 to expand the arms 645 of the fastener element 645 in the enlarged chamber portion 636 of the body so that head 614 is received in the cavity 651 of the fastener element 640. After flange 615 of the bone anchor 610 pushes up into the cavity 651 the arms 645 move inward until the surface 650 is below flange 615 of the bone anchor to capture the bone anchor 610 in the fastener element 640.

The rod 101 may then be inserted into the rod receiving channel 27, 29 and the locking cap 92, 190 engaged with the body 20 to capture the rod 101 and bone anchor 610 with respect to the body 20. To lock the spinal rod and fastener element 640 with respect to the bone anchor 610, the locking cap 92, 190 is advanced downward through the bore 22 in the body 20. As the locking cap 92, 190 applies pressure to the fastener element 640, the fastener element 640 advances downward or is held in the lower chamber 36, placing the outer surface 652 of the arms 645 into contact with the lower chamber surfaces 37 of the lower chamber 36. The lower chamber surfaces 37 of the lower chamber 36 may be configured to exert a radial force on the arms 645, causing the arms 645 to collapse around the head 614 of the bone anchor 610, thereby locking the position of the bone anchor 610 with respect to the body 20, or the lower chamber surfaces 37 may be configured to prevent the arms 645 from expanding (e.g., surfaces 37 will not exert force on arms 645 unless the arms 645 expand to a larger size) in order to lock the spinal rod in the fastener element 640. Where a two-piece locking cap 190 is utilized, this also secures the position of the rod 101. Where a three-piece locking cap 92 is employed, the rod 101 may be separately locked into position by the setscrew 90, as previously described.

The fastener element 640 and body 60 may further be configured to take up lateral movements and moments of the bone anchor relative to the body which may occur during implantation as well as after implantation of the bone anchor system within the patient. In this regard, the fastener element 640 may optionally have one or more substantially cylindrical zones 657, 659, while the body 20 as shown in FIGS. 33 and 34 may optionally include one or more corresponding substantially cylindrical bands 637, 639. When the fastener element 640 is locked, the cylindrical zones 657, 659 preferably are directly opposite cylindrical bands 637, 639 so that any lateral movements or moment forces are taken-up and resisted by the cylindrical zones and cylindrical bands preferably providing stability to the bone anchor assembly.

In the bone anchor assembly 100" of FIG. 34, a flange 603 may optionally be provided on the bone anchor to resist lateral moment forces that may occur when the bone anchor is being clicked onto the fastener element 640 or the fastener element is pushed up so that the aims 645 are aligned with the enlarged chamber 636, referred to as the fastener element click on position. Any lateral moment applied to the bone anchor 640 will cause the bone anchor to angulate in the body 20. The lateral moment when the fastener element 640 is in the click-on position will be resisted by the cylindrical zones 657 bearing on the cylindrical band 637, but since the fastener element is upward in the body bore the cylindrical zone 659 will no longer bear on the cylindrical band 639. To better resist lateral moments when the fastener element 640 is in the click-on position, bone anchor 610 may be provided with flange 603 which optionally has bearing surfaces 604 which will bear against cylindrical bands 639 to resist angulating of the bone anchor 640 caused by lateral moments.

The anchor assemblies may form a single level construct, such that a multitude of anchor assemblies and/or second bone fixation elements are arranged in parallel posteriorly between a pair of vertebral bodies 200, e.g., to assist with a fusion procedure, or alternately, the bone anchor assembly may couple to a more complex construct, such as, for example, a multi-level construct. The bone anchor assembly may also couple transversely to a complex construct, such as in serving as a trans-iliac or trans-sacral extension.

Rather than a second bone anchor assembly 100, 100', 100", any of the anchor assemblies 100, 100', 100" may be used in conjunction with a bone anchor assembly of any other type, such as a bone anchor assembly preassembled with a bone anchor during manufacture or any other type of anchoring assembly that is capable of receiving spinal rod 101. The second bone anchor assembly can further be a monoaxial, monorotational or a polyaxial pedicle screw assembly or can be a lamina hook with a rod-receiving portion.

As will be appreciated by those skilled in the art, any or all of the components described herein may be provided in sets or kits so that the surgeon may select various combinations of components to perform a bone fixation or stability procedures and create a system which is configured specifically for the particular needs and anatomy of a patient. It should be noted that one or more of each component may be provided in a kit or set. In some kits or sets, the same device may be provided in different shapes and/or sizes.

The anchor assembly is preferably provided to the user in a kit including (1) bone anchors, (2) locking caps, (3) pre-assembled bushing/body subassemblies, bushing/sleeve/body subassemblies, or fastener element/body subassemblies, and (4) spinal rods. The pre-assembled bushing/body subassemblies, bushing/sleeve/body subassemblies or fastener element/body subassemblies are preferably assembled during manufacture by inserting the bushing 40, or bushing assembly 162, or fastener element into the axial bore 22 formed in the body 20 through the upper opening 23 formed in the body 20 until the bushing 40, bushing assembly 162 or fastener element is captured and retained in the body.

The kit is preferably delivered to the user for use preferably in spinal surgery. During surgery, the surgeon preferably identifies a level of the spine where the surgery will take place, makes an incision to expose the selected area and implants one or more bone anchors into the desired vertebrae 200 (FIG. 3). The subassembly (body and bushing; body, bushing and sleeve; or body and fastener element) is preferably popped-on to the bone anchor by urging the head through the lower opening 24 in the body 20. Accordingly, the body subassembly may be engaged with the head 14 of the bone anchor 10 in situ.

The anchor assembly including the bone anchor 10, 210, 310, 410, 510, 610; the bushing 40 or bushing assembly 162; the body 20; and the locking cap 92, 190 may be made from any biocompatible material now or hereafter known including, but not limited to, metals such as, for example, titanium, titanium alloys, stainless steel, cobalt chromium, Nitinol, etc. Other materials such as, for example, composites, polymers, ceramics, and any other material now known or hereafter discovered may be used for the anchor assembly, its component parts, and spinal rods.

While the foregoing description and drawings represent the preferred embodiment of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed embodiments are, therefore, to be considered in all respects as illustrative and not restrictive, the scope of the invention being indicated by the appended claims and not limited to the foregoing description.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention, as defined by the appended claims.

The invention claimed is:

1. An anchor assembly configured to couple a bone anchor to a spinal rod for stabilizing bones or bone fragments, the bone anchor including a head portion, the spinal rod elongate along a central axis, the anchor assembly comprising:
   a body having a longitudinal axis, an upper end with an upper opening, and a lower end spaced from the upper end along the longitudinal axis, the lower end having a lower opening, the body defining a bore that extends substantially between the upper opening and the lower opening, and a first rod receiving channel configured and arranged to receive the spinal rod, wherein the first rod-receiving channel is open to the upper opening and extends from the upper end of the body toward the lower end of the body along the longitudinal axis so as to define a top-loading rod receiving channel, and wherein the body defines at least one external recess disposed proximate the first rod receiving channel;
   an insert member disposed at least partially in the bore of the body, the insert member including a first end, a second end spaced from the first end along the longitudinal axis, the second end defining a lower insert member opening, the insert member further including an interior cavity configured to receive at least a portion of the head portion of the bone anchor, and at least one slot that extends from the second end toward the first end, the at least one slot configured to permit at least a portion of the insert member to expand and collapse, the insert member being moveable within the bore of the body; and a locking cap assembly configured to be at least partially received within the bore of the body to retain the spinal rod in the first rod receiving channel, the locking cap assembly including a saddle that includes at least one wing that extends outward from the saddle, wherein the at least one wing is configured to be received by the at least one external recess of the body, the saddle defining a curved surface, a first saddle arm, and a second saddle arm, the curved surface being shaped to conform to a complementary curved surface of the spinal rod such that the curved surface, the first saddle arm, and the second saddle arm at least partially define a second rod receiving channel, and such that the first and second saddle arms extend toward the lower end of the body to at least the central axis of the spinal rod when 1) the locking cap assembly is at least partially received in the bore, and 2) the spinal rod is received in the first and second rod receiving channels, wherein the locking cap assembly is movable within the bore such that, as the locking cap assembly moves, a distal portion of at least one of the first and second saddle arms urges the insert member to move within the bore from an unlocked position to a locked position, wherein, in the unlocked position, the bone anchor is poly-axially rotatable with respect to the body and in the locked position, the insert member secures a position of the bone anchor with respect to the body.

2. The anchor assembly of claim 1, wherein: the insert member is a bushing that defines an outside surface, the outside surface further including a frusto-spherical portion.

3. The anchor assembly of claim 2, wherein the outside surface of the bushing further has at least one cylindrical portion where the surface in the cylindrical portion has a substantially constant diameter when the bushing is not in an undeflected state, and wherein the lower end of the body has a chamber having a substantially cylindrical surface, wherein the bushing is positionable so that the at least one cylindrical portion faces the cylindrical surface of the body so as to inhibit the bushing from angulating in the body.

4. The anchor assembly of claim 1, wherein as the locking cap assembly moves, the distal portion of the at least one of the first and second saddle arms abuts the insert member so as to cause the insert member to move within the bore from the unlocked position to the locked position.

5. The anchor assembly of claim 4, wherein:
the insert member comprises a lower insert member for receiving the head portion of the bone anchor, and a sleeve member interconnected to the lower insert member; and
as the locking cap assembly moves, the distal portion of the at least one of the first and second saddle arms abuts the sleeve member so as to cause the insert member to move within the bore from the unlocked position to the locked position.

6. The anchor assembly of claim 1, wherein the bone anchor is poly-axially rotatable with respect to the body when the locking cap assembly is in the unlocked position.

7. The anchor assembly of claim 1 wherein each of at least one of the saddle arms defines an arm distal end, the arm distal end defining a first interface surface, and the insert member defines a second interface surface that is configured to contact the first interface surface when the at least a portion of the locking assembly is in the locked position, wherein the first and second interface surfaces are inclined.

8. The anchor assembly of claim 1, wherein each of the first and second saddle arms defines an arm distal end and a side surface, the arm distal end defining a first interface surface that is substantially perpendicular to the side surface, and the insert member has a second interface that is configured and arranged to contact the first interface surface of the a respective first and second saddle arms when the locking assembly is in the locked position.

9. The anchor assembly of claim 1 wherein the insert member comprises: a lower insert member for receiving the head portion of the bone anchor, the lower insert member having an outer surface at least a portion of which is frusto-spherical and further having at least one slot and being expandable and compressible, and a sleeve member interconnected to the lower insert member, the sleeve member having a rod-receiving channel.

10. The anchor assembly of claim 1, wherein the insert member defines an outer surface, and at least a portion of the outer surface is curved with respect to the longitudinal axis.

11. The anchor assembly of claim 1, wherein the first and second saddles arms extend to the second end of the insert member when the locking cap assembly is in the locked position.

12. The anchor assembly of claim 1, wherein the first end of the insert defines a proximal-most portion that is farther away from the second end of the insert along the longitudinal axis than any other portion of the insert member, wherein the first and second saddle arms contact a proximal most portion of the insert when the locking cap assembly is in the locked position.

13. The anchor assembly of claim 1, wherein the locking cap assembly is configured such that a position of the rod is securable after securing the position of the bone anchor.

* * * * *